US011597771B2

(12) United States Patent
Iffland et al.

(10) Patent No.: US 11,597,771 B2
(45) Date of Patent: Mar. 7, 2023

(54) MONOCLONAL ANTIBODY DIRECTED TO FGFR1

(71) Applicant: MERCK PATENT GMBH, Darmstadt (DE)

(72) Inventors: Christel Iffland, Arlington, MA (US); Christina Esdar, Darmstadt (DE); Xinyan Zhao, Bedford, MA (US); Qi An, Nashua, NH (US); Johannes Yeh, Billerica, MA (US); Gang Hao, Belmont, MA (US); Lars Toleikis, Kleinniedesheim (DE); Vanita Sood, Somerville, MA (US); David Nannemann, Woburn, MA (US); Robin Lytle, Acton, MA (US); Bjoern Hock, Maintal (DE)

(*) Notice: Subject to any disclaimer, the term of this patent is extended or adjusted under 35 U.S.C. 154(b) by 747 days.

(21) Appl. No.: 16/462,961

(22) PCT Filed: Nov. 21, 2017

(86) PCT No.: PCT/EP2017/079976
§ 371 (c)(1),
(2) Date: May 22, 2019

(87) PCT Pub. No.: WO2018/095932
PCT Pub. Date: May 31, 2018

(65) Prior Publication Data
US 2019/0367620 A1 Dec. 5, 2019

Related U.S. Application Data

(60) Provisional application No. 62/425,325, filed on Nov. 22, 2016.

(30) Foreign Application Priority Data

Nov. 23, 2016 (EP) .................................... 16200304
Apr. 13, 2017 (EP) .................................... 17166540

(51) Int. Cl.
C12N 15/13 (2006.01)
C07K 16/28 (2006.01)
A61P 35/00 (2006.01)
A61K 39/00 (2006.01)

(52) U.S. Cl.
CPC .......... *C07K 16/2863* (2013.01); *A61P 35/00* (2018.01); *A61K 2039/505* (2013.01); *C07K 2317/21* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2014/0105821 A1  4/2014 Tymofeev

FOREIGN PATENT DOCUMENTS

| AU | 2014271291 | 1/2015 |
| EP | 2 450 055 | 5/2012 |
| WO | WO 2012/125124 | 9/2012 |
| WO | WO 2014/093908 | 6/2014 |

OTHER PUBLICATIONS

Written Opinion in International Application No. PCT/EP2017/079976, dated Jan. 30, 2018, pp. 1-9.
Du, J. et al. "Molecular Basis of Recognition of Human Osteopontin by 23C3, a Potential Therapeutic Antibody for Treatment of Rheumatoid Arthritis" *Journal of Molecular Biology*, Jul. 31, 2008 pp. 835-842, vol. 382, No. 4.
Caldas, C. et al. "Humanization of the anti-CD18 antibody 6.7: an unexpected effect of a framework residue in binding to antigen" *Molecular Immunology*, 2003, pp. 941-952, vol. 39, No. 15.
Kunik, V. et al. "Structural Consensus among Antibodies Defines the Antigen Binding Site" *PLoS Computational Biology*, Feb. 23, 2012, pp. 1-12, vol. 8, Issue 2, e1002388.
Casadevall, A. et al. "Immunoglobulin isotype influences affinity and specificity" *PNAS*, Jul. 31, 2012, pp. 12272-12273, vol. 109, No. 31.

*Primary Examiner* — Michael D Pak
(74) *Attorney, Agent, or Firm* — Saliwanchik, Lloyd & Eisenschenk

(57) ABSTRACT

The present invention relates to antibodies with specificity for FGFR1. More particularly, the invention relates to monoclonal antibodies that bind specifically to and neutralize human, macaque and mouse forms of FGFR1 with high affinity. The invention also relates to nucleic acids encoding said antibodies, vectors for expression of these nucleic acids, and host cells for producing said antibodies. Further, the invention relates to the use of said antibodies in the diagnosis and/or treatment of cancers.

15 Claims, 8 Drawing Sheets

Specification includes a Sequence Listing.

RPSPTLPEQDALPSSEDDDDDDDSSSEEKETDNTKPNPVAPYWTSPEKMEKKLHAVPAAKTVKFKCPSSG

TPNPTLRWLKNGKEFKPDHRIGGYKVRYATWSIIMDSVVPSDKGNYTCIVENEYGSINHTYQLDVVERSP

HRPILQAGLPANKTVALGSN*VEFMCKVYSDPQPHIQWLKHIEVNGSKIGPDNLPYVQILKTAGVNTTDKE*

*MEVLHLRNVSFEDAGEYTCLA*GNSIGLSHHSAWLTVLEALEERPAVMTSPLYLEHHHHHH

SEQUENCE LISTING

```
<160> NUMBER OF SEQ ID NOS: 113

<210> SEQ ID NO 1
<211> LENGTH: 116
<212> TYPE: PRT
<213> ORGANISM: Artificial sequence
<220> FEATURE:
<223> OTHER INFORMATION: Variable heavy chain of antibody #A08 hit

<400> SEQUENCE: 1

Glu Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Ser Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Asn Ser Val Thr Ala Ala Asp Thr Ala Val Tyr Tyr Cys
                85                  90                  95

Ala Arg Gly Thr Asp Trp Phe Asp Pro Trp Gly Gln Gly Thr Leu Val
            100                 105                 110

Thr Val Ser Ser
        115

<210> SEQ ID NO 2
<211> LENGTH: 108
<212> TYPE: PRT
<213> ORGANISM: Artificial sequence
<220> FEATURE:
<223> OTHER INFORMATION: Variable light chain of antibody #A08 hit

<400> SEQUENCE: 2

Gln Ala Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Glu Ser Val
            20                  25                  30

His Trp Tyr Gln Gln Lys Pro Gly Gln Ala Pro Val Leu Val Val Tyr
```

-continued

```
                35                  40                  45
Asp Asp Ser Asp Arg Pro Ser Gly Ile Pro Glu Arg Phe Gly Ser
        50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Ser Thr Ser Asp His
                85                  90                  95
Arg Val Phe Gly Gly Gly Thr Lys Leu Thr Val Leu
            100                 105
```

<210> SEQ ID NO 3
<211> LENGTH: 9
<212> TYPE: PRT
<213> ORGANISM: Artificial sequence
<220> FEATURE:
<223> OTHER INFORMATION: CDR-1 of the heavy chain of antibody #A08 hit
      and lead

<400> SEQUENCE: 3

```
Gly Gly Ser Ile Ser Ser Asn Asn Trp
1               5
```

<210> SEQ ID NO 4
<211> LENGTH: 7
<212> TYPE: PRT
<213> ORGANISM: Artificial sequence
<220> FEATURE:
<223> OTHER INFORMATION: CDR-2 of the heavy chain of antibody #A08 hit
      and lead

<400> SEQUENCE: 4

```
Ile Tyr His Ser Gly Ser Thr
1               5
```

<210> SEQ ID NO 5
<211> LENGTH: 9
<212> TYPE: PRT
<213> ORGANISM: Artificial sequence
<220> FEATURE:
<223> OTHER INFORMATION: CDR-3 of the heavy chain of antibody #A08 hit
      and lead

<400> SEQUENCE: 5

```
Ala Arg Gly Thr Asp Trp Phe Asp Pro
1               5
```

<210> SEQ ID NO 6
<211> LENGTH: 9
<212> TYPE: PRT
<213> ORGANISM: Artificial sequence
<220> FEATURE:
<223> OTHER INFORMATION: alternative CDR-1 of the heavy chain of
      antibody #A08 hit

<400> SEQUENCE: 6

```
Gly Gly Ser Ile Ser Gly Asn Asn Trp
1               5
```

<210> SEQ ID NO 7
<211> LENGTH: 9
<212> TYPE: PRT
<213> ORGANISM: Artificial sequence
<220> FEATURE:
<223> OTHER INFORMATION: alternative CDR-1 of the heavy chain of
      antibody #A08 hit

```
<400> SEQUENCE: 7

Gly Gly Ser Ile Asn Ser Asn His Trp
1               5

<210> SEQ ID NO 8
<211> LENGTH: 7
<212> TYPE: PRT
<213> ORGANISM: Artificial sequence
<220> FEATURE:
<223> OTHER INFORMATION: alternative CDR-2 of the heavy chain of
      antibody #A08 hit

<400> SEQUENCE: 8

Ile Tyr His Ser Gly Ser Val
1               5

<210> SEQ ID NO 9
<211> LENGTH: 9
<212> TYPE: PRT
<213> ORGANISM: Artificial sequence
<220> FEATURE:
<223> OTHER INFORMATION: alternative CDR-3 of the heavy chain of
      antibody #A08 hit
<220> FEATURE:
<221> NAME/KEY: MISC_FEATURE
<222> LOCATION: (9)..(9)
<223> OTHER INFORMATION: X being any residues selected from the group
      consisting of proline (P), glutamine (Q), alanine (A), leucine
      (L), histidine (H), serine (S) or threonine (T)

<400> SEQUENCE: 9

Ala Arg Ala Thr Asp Trp Phe Asp Xaa
1               5

<210> SEQ ID NO 10
<211> LENGTH: 9
<212> TYPE: PRT
<213> ORGANISM: Artificial sequence
<220> FEATURE:
<223> OTHER INFORMATION: alternative CDR-3 of the heavy chain of
      antibody #A08 hit

<400> SEQUENCE: 10

Ala Arg Gly Thr Asp Trp Tyr Asp Pro
1               5

<210> SEQ ID NO 11
<211> LENGTH: 9
<212> TYPE: PRT
<213> ORGANISM: Artificial sequence
<220> FEATURE:
<223> OTHER INFORMATION: alternative CDR-3 of the heavy chain of
      antibody #A08 hit

<400> SEQUENCE: 11

Ala Arg Gly Thr Asp Trp Ile Asp Thr
1               5

<210> SEQ ID NO 12
<211> LENGTH: 9
<212> TYPE: PRT
<213> ORGANISM: Artificial sequence
<220> FEATURE:
<223> OTHER INFORMATION: alternative CDR-3 of the heavy chain of
      antibody #A08 hit

<400> SEQUENCE: 12

Ala Arg Ser Thr Asp Trp Phe Asp Pro
```

```
<210> SEQ ID NO 13
<211> LENGTH: 9
<212> TYPE: PRT
<213> ORGANISM: Artificial sequence
<220> FEATURE:
<223> OTHER INFORMATION: alternative CDR-3 of the heavy chain of
      antibody #A08 hit

<400> SEQUENCE: 13

Ala Arg Gly Thr Asp Trp Tyr Asp Ala
1               5

<210> SEQ ID NO 14
<211> LENGTH: 9
<212> TYPE: PRT
<213> ORGANISM: Artificial sequence
<220> FEATURE:
<223> OTHER INFORMATION: alternative CDR-3 of the heavy chain of
      antibody #A08 hit

<400> SEQUENCE: 14

Ala Arg Gly Thr Asp Trp Tyr Asp Leu
1               5

<210> SEQ ID NO 15
<211> LENGTH: 9
<212> TYPE: PRT
<213> ORGANISM: Artificial sequence
<220> FEATURE:
<223> OTHER INFORMATION: alternative CDR-3 of the heavy chain of
      antibody #A08 hit
<220> FEATURE:
<221> NAME/KEY: MISC_FEATURE
<222> LOCATION: (3)..(3)
<223> OTHER INFORMATION: X being any residues selected from the group
      consisting of S serine (S) or valine (V)

<400> SEQUENCE: 15

Ala Arg Xaa Thr Asp Trp Phe Asp Pro
1               5

<210> SEQ ID NO 16
<211> LENGTH: 9
<212> TYPE: PRT
<213> ORGANISM: Artificial sequence
<220> FEATURE:
<223> OTHER INFORMATION: alternative CDR-3 of the heavy chain of
      antibody #A08 hit

<400> SEQUENCE: 16

Ala Arg Ala Lys Asp Trp Phe Asp Ala
1               5

<210> SEQ ID NO 17
<211> LENGTH: 9
<212> TYPE: PRT
<213> ORGANISM: Artificial sequence
<220> FEATURE:
<223> OTHER INFORMATION: alternative CDR-3 of the heavy chain of
      antibody #A08 hit

<400> SEQUENCE: 17

Ala Arg Ala Thr Asp Trp Tyr Asp Pro
1               5

<210> SEQ ID NO 18
```

```
<211> LENGTH: 6
<212> TYPE: PRT
<213> ORGANISM: Artificial sequence
<220> FEATURE:
<223> OTHER INFORMATION: CDR-1 of the light chain of antibody #A08 hit
      and lead

<400> SEQUENCE: 18

Asn Ile Gly Ser Glu Ser
1               5

<210> SEQ ID NO 19
<211> LENGTH: 3
<212> TYPE: PRT
<213> ORGANISM: Artificial sequence
<220> FEATURE:
<223> OTHER INFORMATION: CDR-2 of the light chain of antibody #A08 hit
      and lead

<400> SEQUENCE: 19

Asp Asp Ser
1

<210> SEQ ID NO 20
<211> LENGTH: 11
<212> TYPE: PRT
<213> ORGANISM: Artificial sequence
<220> FEATURE:
<223> OTHER INFORMATION: CDR-3 of the light chain of antibody #A08 hit
      and lead

<400> SEQUENCE: 20

Gln Val Trp Asp Ser Thr Ser Asp His Arg Val
1               5                   10

<210> SEQ ID NO 21
<211> LENGTH: 6
<212> TYPE: PRT
<213> ORGANISM: Artificial sequence
<220> FEATURE:
<223> OTHER INFORMATION: alternative CDR-1 of the light chain of
      antibody #A08 hit

<400> SEQUENCE: 21

Asn Ile Gly Asp Glu Thr
1               5

<210> SEQ ID NO 22
<211> LENGTH: 11
<212> TYPE: PRT
<213> ORGANISM: Artificial sequence
<220> FEATURE:
<223> OTHER INFORMATION: alternative CDR-3 of the light chain of
      antibody #A08 hit

<400> SEQUENCE: 22

Gln Val Trp Asp Ser Ser Val Asp Gln Ala Val
1               5                   10

<210> SEQ ID NO 23
<211> LENGTH: 11
<212> TYPE: PRT
<213> ORGANISM: Artificial sequence
<220> FEATURE:
<223> OTHER INFORMATION: alternative CDR-3 of the light chain of
      antibody #A08 hit

<400> SEQUENCE: 23
```

Gln Val Trp Asp Ser Ser Ser Asp His Arg Val
1               5                   10

<210> SEQ ID NO 24
<211> LENGTH: 116
<212> TYPE: PRT
<213> ORGANISM: Artificial sequence
<220> FEATURE:
<223> OTHER INFORMATION: Variable heavy chain of antibody #A08 lead

<400> SEQUENCE: 24

Glu Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Thr Asp Trp Phe Asp Pro Trp Gly Gln Gly Thr Leu Val
            100                 105                 110

Thr Val Ser Ser
        115

<210> SEQ ID NO 25
<211> LENGTH: 108
<212> TYPE: PRT
<213> ORGANISM: Artificial sequence
<220> FEATURE:
<223> OTHER INFORMATION: Variable light chain of antibody #A08 lead

<400> SEQUENCE: 25

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Glu Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Thr Ser Asp His
                85                  90                  95

Arg Val Phe Gly Gly Gly Thr Lys Leu Thr Val Leu
            100                 105

<210> SEQ ID NO 26
<211> LENGTH: 128
<212> TYPE: PRT
<213> ORGANISM: Artificial sequence
<220> FEATURE:
<223> OTHER INFORMATION: Variable heavy chain of antibody #A05 hit

<400> SEQUENCE: 26

Gln Met Gln Leu Val Gln Ser Gly Ala Glu Val Lys Lys Pro Gly Ala

```
               1               5                  10                 15
           Ser Val Lys Val Ser Cys Lys Ala Ser Gly His Thr Phe Thr Gly Tyr
                       20                  25                 30

Tyr Met His Trp Val Arg Gln Ala Pro Gly Gln Gly Leu Glu Trp Met
                       35                  40                 45

Gly Trp Ile Asn Pro Asn Ser Gly Gly Thr Asn Tyr Ala Gln Lys Phe
                       50                  55                 60

Gln Gly Arg Val Thr Met Thr Arg Asp Thr Ser Ile Ser Thr Ala Tyr
            65                  70                  75                 80

Met Glu Leu Ser Arg Leu Arg Ser Asp Asp Thr Ala Val Tyr Tyr Cys
                       85                  90                 95

Ala Arg Asp Leu Phe Trp Ser Leu Ser Ser Gly Trp Ser Ile His Pro
                       100                 105                110

Tyr Tyr Phe Asp Tyr Trp Gly Gln Gly Thr Leu Val Thr Val Ser Ser
                       115                 120                125

<210> SEQ ID NO 27
           <211> LENGTH: 128
           <212> TYPE: PRT
           <213> ORGANISM: Artificial sequence
           <220> FEATURE:
           <223> OTHER INFORMATION: Variable heavy chain of antibody #A05 lead

<400> SEQUENCE: 27

Glu Val Gln Leu Val Gln Ser Gly Ala Glu Val Lys Lys Pro Gly Ala
            1               5                  10                 15

Ser Val Lys Val Ser Cys Lys Ala Ser Gly His Thr Phe Thr Gly Tyr
                       20                  25                 30

Tyr Met His Trp Val Arg Gln Ala Pro Gly Gln Gly Leu Glu Trp Met
                       35                  40                 45

Gly Trp Ile Asn Pro Asn Ser Gly Gly Thr Asn Tyr Ala Gln Lys Phe
                       50                  55                 60

Gln Gly Arg Val Thr Met Thr Arg Asp Thr Ser Ile Ser Thr Ala Tyr
            65                  70                  75                 80

Met Glu Leu Ser Arg Leu Arg Ser Asp Asp Thr Ala Val Tyr Tyr Cys
                       85                  90                 95

Ala Arg Asp Leu Phe Trp Ser Leu Ser Ser Gly Trp Ser Ile His Pro
                       100                 105                110

Tyr Tyr Phe Asp Tyr Trp Gly Gln Gly Thr Leu Val Thr Val Ser Ser
                       115                 120                125

<210> SEQ ID NO 28
           <211> LENGTH: 109
           <212> TYPE: PRT
           <213> ORGANISM: Artificial sequence
           <220> FEATURE:
           <223> OTHER INFORMATION: Variable light chain of antibody #A05 hit

<400> SEQUENCE: 28

Gln Ser Ala Leu Thr Gln Pro Ala Ser Val Ser Gly Ser Pro Gly Gln
            1               5                  10                 15

Ser Ile Thr Ile Ser Cys Thr Gly Thr Ser Ser Asp Val Gly Ser Tyr
                       20                  25                 30

Asn Leu Val Ser Trp Tyr Gln Gln His Pro Gly Lys Ala Pro Lys Leu
                       35                  40                 45

Met Ile Tyr Gly Gly Ser Lys Arg Pro Ser Gly Val Pro Asp Arg Phe
                       50                  55                 60
```

```
Ser Gly Ser Lys Ser Asp Thr Ser Ala Ser Leu Thr Ile Ser Gly Leu
 65                  70                  75                  80

Gln Ala Glu Asp Glu Ala Asp Tyr Tyr Cys Cys Ser Tyr Thr Tyr Asn
                 85                  90                  95

Gly Asp Val Phe Gly Thr Gly Thr Lys Val Thr Val Leu
            100                 105

<210> SEQ ID NO 29
<211> LENGTH: 109
<212> TYPE: PRT
<213> ORGANISM: Artificial sequence
<220> FEATURE:
<223> OTHER INFORMATION: Variable light chain of antibody #A05 lead

<400> SEQUENCE: 29

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Gly Gly Ser Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Tyr Ser
                 85                  90                  95

Gly Asp Val Phe Gly Thr Gly Thr Lys Val Thr Val Leu
            100                 105

<210> SEQ ID NO 30
<211> LENGTH: 25
<212> TYPE: PRT
<213> ORGANISM: Artificial sequence
<220> FEATURE:
<223> OTHER INFORMATION: FR-1 of the heavy chain of antibody #A08 family
<220> FEATURE:
<221> NAME/KEY: MISC_FEATURE
<222> LOCATION: (1)..(1)
<223> OTHER INFORMATION: X being any residues selected from the group
      consisting of Glutamine (Q) and Gluamic acid (E)

<400> SEQUENCE: 30

Xaa Val Gln Leu Gln Glu Ser Gly Pro Gly Leu Val Lys Pro Ser Gly
1               5                   10                  15

Thr Leu Ser Leu Thr Cys Ala Val Ser
            20                  25

<210> SEQ ID NO 31
<211> LENGTH: 17
<212> TYPE: PRT
<213> ORGANISM: Artificial sequence
<220> FEATURE:
<223> OTHER INFORMATION: FR-2 of the heavy chain of antibody #A08 family

<400> SEQUENCE: 31

Trp Ser Trp Val Arg Gln Pro Pro Gly Lys Gly Leu Glu Trp Ile Gly
1               5                   10                  15

Glu

<210> SEQ ID NO 32
<211> LENGTH: 38
```

```
<212> TYPE: PRT
<213> ORGANISM: Artificial sequence
<220> FEATURE:
<223> OTHER INFORMATION: FR-3 of the heavy chain of antibody #A08 family
<220> FEATURE:
<221> NAME/KEY: MISC_FEATURE
<222> LOCATION: (26)..(26)
<223> OTHER INFORMATION: X being any residues selected from the group
      consisting of Serine (S) or Asparagine (N)

<400> SEQUENCE: 32

Ser Tyr Asn Pro Ser Leu Lys Ser Arg Val Thr Ile Ser Val Asp Lys
1               5                   10                  15

Ser Lys Asn Gln Phe Ser Leu Lys Leu Xaa Ser Val Thr Ala Ala Asp
            20                  25                  30

Thr Ala Val Tyr Tyr Cys
        35

<210> SEQ ID NO 33
<211> LENGTH: 11
<212> TYPE: PRT
<213> ORGANISM: Artificial sequence
<220> FEATURE:
<223> OTHER INFORMATION: FR-4 of the heavy chain of antibody #A08 family

<400> SEQUENCE: 33

Trp Gly Gln Gly Thr Leu Val Thr Val Ser Ser
1               5                   10

<210> SEQ ID NO 34
<211> LENGTH: 25
<212> TYPE: PRT
<213> ORGANISM: Artificial sequence
<220> FEATURE:
<223> OTHER INFORMATION: FR-1 of the light chain of antibody #A08 family
<220> FEATURE:
<221> NAME/KEY: MISC_FEATURE
<222> LOCATION: (1)..(1)
<223> OTHER INFORMATION: X in position 1 being any residues selected
      from the group consisting of Glutamine (Q) and Serine (S)
<220> FEATURE:
<221> NAME/KEY: MISC_FEATURE
<222> LOCATION: (2)..(2)
<223> OTHER INFORMATION: X in position 2 being any residues selected
      from the group consisting of Alanine (A), Serine (S) and Tyrosine
      (Y)

<400> SEQUENCE: 34

Xaa Xaa Val Leu Thr Gln Pro Pro Ser Val Ser Val Ala Pro Gly Gln
1               5                   10                  15

Thr Ala Arg Ile Thr Cys Gly Gly Asn
            20                  25

<210> SEQ ID NO 35
<211> LENGTH: 17
<212> TYPE: PRT
<213> ORGANISM: Artificial sequence
<220> FEATURE:
<223> OTHER INFORMATION: FR-2 of the light chain of antibody #A08 family

<400> SEQUENCE: 35

Val His Trp Tyr Gln Gln Lys Pro Gly Gln Ala Pro Val Leu Val Val
1               5                   10                  15

Tyr

<210> SEQ ID NO 36
<211> LENGTH: 36
```

```
<212> TYPE: PRT
<213> ORGANISM: Artificial sequence
<220> FEATURE:
<223> OTHER INFORMATION: FR-3 of the light chain of antibody #A08 family

<400> SEQUENCE: 36

Asp Arg Pro Ser Gly Ile Pro Glu Arg Phe Ser Gly Ser Asn Ser Gly
1               5                   10                  15

Asn Thr Ala Thr Leu Thr Ile Ser Arg Val Glu Ala Gly Asp Glu Ala
            20                  25                  30

Asp Tyr Tyr Cys
            35

<210> SEQ ID NO 37
<211> LENGTH: 10
<212> TYPE: PRT
<213> ORGANISM: Artificial sequence
<220> FEATURE:
<223> OTHER INFORMATION: FR-4 of the light chain of antibody #A08 family

<400> SEQUENCE: 37

Phe Gly Gly Gly Thr Lys Leu Thr Val Leu
1               5                   10

<210> SEQ ID NO 38
<211> LENGTH: 329
<212> TYPE: PRT
<213> ORGANISM: Artificial sequence
<220> FEATURE:
<223> OTHER INFORMATION: heavy chain constant region ? human IgG1
      allotype G1m3

<400> SEQUENCE: 38

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
        210             215                 220

Gln Pro Arg Glu Pro Gln Val Tyr Thr Leu Pro Pro Ser Arg Glu Glu
225             230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305             310                 315                 320

Gln Lys Ser Leu Ser Leu Ser Pro Gly
                325
```

<210> SEQ ID NO 39
<211> LENGTH: 328
<212> TYPE: PRT
<213> ORGANISM: Artificial sequence
<220> FEATURE:
<223> OTHER INFORMATION: heavy chain constant region ? human IgG2 allotype G2h

<400> SEQUENCE: 39

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Pro Lys Ser Ser Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Ala Gln Ser Thr Phe Arg Val Val Ser Val Leu Thr Val Val His
            180                 185                 190

Gln Asp Trp Leu Asn Gly Lys Glu Tyr Lys Cys Ala Val Ser Asn Lys
        195                 200                 205

Gly Leu Pro Ala Pro Ile Glu Lys Thr Ile Ser Lys Thr Lys Gly Gln
    210                 215                 220

Pro Arg Glu Pro Gln Val Tyr Thr Leu Pro Pro Ser Arg Glu Glu Met
225                 230                 235                 240
```

```
Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Met Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly
                325
```

<210> SEQ ID NO 40
<211> LENGTH: 332
<212> TYPE: PRT
<213> ORGANISM: Artificial sequence
<220> FEATURE:
<223> OTHER INFORMATION: heavy chain constant region CH1-hinge-CH2-CH3 ?
      SEED(AG)

<400> SEQUENCE: 40

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Phe Arg Pro Glu Val His Leu Leu Pro Ser Arg Glu Glu
225                 230                 235                 240

Met Thr Lys Asn Gln Val Ser Leu Thr Cys Leu Ala Arg Gly Phe Tyr
                245                 250                 255

Pro Lys Asp Ile Ala Val Glu Trp Glu Ser Asn Gly Gln Pro Glu Asn
```

```
                    260                 265                 270
Asn Tyr Lys Thr Thr Pro Ser Arg Gln Glu Pro Ser Gln Gly Thr Thr
                275                 280                 285

Thr Phe Ala Val Thr Ser Lys Leu Thr Val Asp Lys Ser Arg Trp Gln
            290                 295                 300

Gln Gly Asn Val Phe Ser Cys Ser Val Met His Glu Ala Leu His Asn
305                 310                 315                 320

His Tyr Thr Gln Lys Thr Ile Ser Leu Ser Pro Gly
                325                 330

<210> SEQ ID NO 41
<211> LENGTH: 234
<212> TYPE: PRT
<213> ORGANISM: Artificial sequence
<220> FEATURE:
<223> OTHER INFORMATION: heavy chain constant region hinge-CH2-CH3 ?
      SEED(GA)

<400> SEQUENCE: 41

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Glu Glu Leu Ala
    130                 135                 140

Leu Asn Glu Leu Val Thr Leu Thr Cys Leu Val Lys Gly Phe Tyr Pro
145                 150                 155                 160

Ser Asp Ile Ala Val Glu Trp Leu Gln Gly Ser Gln Glu Leu Pro Arg
                165                 170                 175

Glu Lys Tyr Leu Thr Trp Ala Pro Val Leu Asp Ser Asp Gly Ser Phe
            180                 185                 190

Phe Leu Tyr Ser Ile Leu Arg Val Ala Ala Glu Asp Trp Lys Lys Gly
        195                 200                 205

Asp Thr Phe Ser Cys Ser Val Met His Glu Ala Leu His Asn His Tyr
    210                 215                 220

Thr Gln Lys Ser Leu Asp Arg Ser Pro Gly
225                 230

<210> SEQ ID NO 42
<211> LENGTH: 332
<212> TYPE: PRT
<213> ORGANISM: Artificial sequence
<220> FEATURE:
<223> OTHER INFORMATION: heavy chain constant region CH1-hinge-CH2-CH3 ?
      SEED(GA)
```

<400> SEQUENCE: 42

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Ser Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Glu Glu
225                 230                 235                 240

Leu Ala Leu Asn Glu Leu Val Thr Leu Thr Cys Leu Val Lys Gly Phe
                245                 250                 255

Tyr Pro Ser Asp Ile Ala Val Glu Trp Leu Gln Gly Ser Gln Glu Leu
            260                 265                 270

Pro Arg Glu Lys Tyr Leu Thr Trp Ala Pro Val Leu Asp Ser Asp Gly
        275                 280                 285

Ser Phe Phe Leu Tyr Ser Ile Leu Arg Val Ala Ala Glu Asp Trp Lys
    290                 295                 300

Lys Gly Asp Thr Phe Ser Cys Ser Val Met His Glu Ala Leu His Asn
305                 310                 315                 320

His Tyr Thr Gln Lys Ser Leu Asp Arg Ser Pro Gly
                325                 330
```

<210> SEQ ID NO 43
<211> LENGTH: 234
<212> TYPE: PRT
<213> ORGANISM: Artificial sequence
<220> FEATURE:
<223> OTHER INFORMATION: heavy chain constant region hinge-CH2-CH3 ?
      SEED(AG)

<400> SEQUENCE: 43

```
Glu Pro Lys Ser Cys Asp Lys Thr His Thr Cys Pro Pro Cys Pro Ala
1               5                   10                  15
```

Pro Glu Leu Leu Gly Gly Pro Ser Val Phe Leu Phe Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Phe Arg Pro Glu Val His Leu Leu Pro Pro Ser Arg Glu Glu Met Thr
    130                 135                 140

Lys Asn Gln Val Ser Leu Thr Cys Leu Ala Arg Gly Phe Tyr Pro Lys
145                 150                 155                 160

Asp Ile Ala Val Glu Trp Glu Ser Asn Gly Gln Pro Glu Asn Asn Tyr
                165                 170                 175

Lys Thr Thr Pro Ser Arg Gln Glu Pro Ser Gln Gly Thr Thr Thr Phe
            180                 185                 190

Ala Val Thr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
210                 215                 220

Thr Gln Lys Thr Ile Ser Leu Ser Pro Gly
225                 230

<210> SEQ ID NO 44
<211> LENGTH: 106
<212> TYPE: PRT
<213> ORGANISM: Artificial sequence
<220> FEATURE:
<223> OTHER INFORMATION: light chain constant region (lambda)

<400> SEQUENCE: 44

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 45
<211> LENGTH: 445
<212> TYPE: PRT
<213> ORGANISM: Artificial sequence
<220> FEATURE:

<223> OTHER INFORMATION: heavy chain for #A08 lead-IgG1m3 antibody

<400> SEQUENCE: 45

```
Glu Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Thr Asp Trp Phe Asp Pro Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400
```

```
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly
        435                 440                 445

<210> SEQ ID NO 46
<211> LENGTH: 448
<212> TYPE: PRT
<213> ORGANISM: Artificial sequence
<220> FEATURE:
<223> OTHER INFORMATION: heavy chain for #A08 lead-SEED(AG) antibody

<400> SEQUENCE: 46

Glu Val Gln Leu Gln Glu Ser Gly Pro Gly Leu Val Lys Pro Ser Gly
1               5                   10                  15
Thr Leu Ser Leu Thr Cys Ala Val Ser Gly Gly Ser Ile Ser Ser Asn
            20                  25                  30
Asn Trp Trp Ser Trp Val Arg Gln Pro Pro Gly Lys Gly Leu Glu Trp
        35                  40                  45
Ile Gly Glu Ile Tyr His Ser Gly Ser Thr Ser Tyr Asn Pro Ser Leu
    50                  55                  60
Lys Ser Arg Val Thr Ile Ser Val Asp Lys Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Gly Thr Asp Trp Phe Asp Pro Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Arg Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
```

Lys Val Ser Asn Lys Ala Leu Pro Ala Pro Ile Glu Lys Thr Ile Ser
            325                 330                 335

Lys Ala Lys Gly Gln Pro Phe Arg Pro Glu Val His Leu Leu Pro Pro
        340                 345                 350

Ser Arg Glu Glu Met Thr Lys Asn Gln Val Ser Leu Thr Cys Leu Ala
        355                 360                 365

Arg Gly Phe Tyr Pro Lys Asp Ile Ala Val Glu Trp Glu Ser Asn Gly
        370                 375                 380

Gln Pro Glu Asn Asn Tyr Lys Thr Thr Pro Ser Arg Gln Glu Pro Ser
385                 390                 395                 400

Gln Gly Thr Thr Thr Phe Ala Val Thr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Thr Ile Ser Leu Ser Pro Gly
        435                 440                 445

<210> SEQ ID NO 47
<211> LENGTH: 448
<212> TYPE: PRT
<213> ORGANISM: Artificial sequence
<220> FEATURE:
<223> OTHER INFORMATION: heavy chain for #A08 lead-SEED(GA) antibody

<400> SEQUENCE: 47

Glu Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Thr Asp Trp Phe Asp Pro Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Ser Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Pro Ser Glu Glu Leu Ala Leu Asn Glu Leu Val Thr Leu Thr Cys Leu
        355                 360                 365

Val Lys Gly Phe Tyr Pro Ser Asp Ile Ala Val Glu Trp Leu Gln Gly
    370                 375                 380

Ser Gln Glu Leu Pro Arg Glu Lys Tyr Leu Thr Trp Ala Pro Val Leu
385                 390                 395                 400

Asp Ser Asp Gly Ser Phe Phe Leu Tyr Ser Ile Leu Arg Val Ala Ala
                405                 410                 415

Glu Asp Trp Lys Lys Gly Asp Thr Phe Ser Cys Ser Val Met His Glu
            420                 425                 430

Ala Leu His Asn His Tyr Thr Gln Lys Ser Leu Asp Arg Ser Pro Gly
        435                 440                 445

<210> SEQ ID NO 48
<211> LENGTH: 460
<212> TYPE: PRT
<213> ORGANISM: Artificial sequence
<220> FEATURE:
<223> OTHER INFORMATION: heavy chain for #A05 lead-SEED(AG) antibody

<400> SEQUENCE: 48

Glu Val Gln Leu Val Gln Ser Gly Ala Glu Val Lys Lys Pro Gly Ala
1               5                   10                  15

Ser Val Lys Val Ser Cys Lys Ala Ser Gly His Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Phe Trp Ser Leu Ser Ser Gly Trp Ser Ile His Pro
            100                 105                 110

Tyr Tyr Phe Asp Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Phe Arg Pro Glu Val His Leu Leu Pro Pro Ser Arg Glu Glu
        355                 360                 365

Met Thr Lys Asn Gln Val Ser Leu Thr Cys Leu Ala Arg Gly Phe Tyr
    370                 375                 380

Pro Lys Asp Ile Ala Val Glu Trp Glu Ser Asn Gly Gln Pro Glu Asn
385                 390                 395                 400

Asn Tyr Lys Thr Thr Pro Ser Arg Gln Glu Pro Ser Gln Gly Thr Thr
                405                 410                 415

Thr Phe Ala Val Thr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Thr Ile Ser Leu Ser Pro Gly
    450                 455                 460

<210> SEQ ID NO 49
<211> LENGTH: 460
<212> TYPE: PRT
<213> ORGANISM: Artificial sequence
<220> FEATURE:
<223> OTHER INFORMATION: heavy chain for #A05 lead-SEED(GA) antibody

<400> SEQUENCE: 49

Glu Val Gln Leu Val Gln Ser Gly Ala Glu Val Lys Lys Pro Gly Ala
1               5                   10                  15

Ser Val Lys Val Ser Cys Lys Ala Ser Gly His Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Asp Leu Phe Trp Ser Leu Ser Ser Gly Trp Ser Ile His Pro
            100                 105                 110

Tyr Tyr Phe Asp Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Arg Val Glu Pro Lys Ser Ser Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Glu Glu
        355                 360                 365

Leu Ala Leu Asn Glu Leu Val Thr Leu Thr Cys Leu Val Lys Gly Phe
    370                 375                 380

Tyr Pro Ser Asp Ile Ala Val Glu Trp Leu Gln Gly Ser Gln Glu Leu
385                 390                 395                 400

Pro Arg Glu Lys Tyr Leu Thr Trp Ala Pro Val Leu Asp Ser Asp Gly
                405                 410                 415

Ser Phe Phe Leu Tyr Ser Ile Leu Arg Val Ala Ala Glu Asp Trp Lys
            420                 425                 430

Lys Gly Asp Thr Phe Ser Cys Ser Val Met His Glu Ala Leu His Asn
        435                 440                 445

His Tyr Thr Gln Lys Ser Leu Asp Arg Ser Pro Gly
    450                 455                 460

<210> SEQ ID NO 50
<211> LENGTH: 214
<212> TYPE: PRT

<213> ORGANISM: Artificial sequence
<220> FEATURE:
<223> OTHER INFORMATION: Light chain for #A08 lead

<400> SEQUENCE: 50

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Glu Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Arg Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Lys Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 51
<211> LENGTH: 215
<212> TYPE: PRT
<213> ORGANISM: Artificial sequence
<220> FEATURE:
<223> OTHER INFORMATION: Light chain for #A05 lead

<400> SEQUENCE: 51

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Gly Gly Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Tyr Ser
                85                  90                  95

Gly Asp Val Phe Gly Thr Gly Thr Lys Val Thr Val Leu Gly Gln Pro
                100                 105                 110
```

```
Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Lys
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 52
<211> LENGTH: 348
<212> TYPE: DNA
<213> ORGANISM: Artificial sequence
<220> FEATURE:
<223> OTHER INFORMATION: Variable heavy chain of antibody #A08 hit

<400> SEQUENCE: 52
gaggtgcagc tgcaggagtc gggcccagga ctggtgaagc cttcggggac cctgtccctc      60
acctgcgctg tctctggtgg ctccatcagc agtaataact ggtggagttg ggtccgccag     120
cccccaggga aggggctgga gtggattggg gaaatctatc atagtgggag caccagctac     180
aacccgtccc tcaagagtcg agtcaccata tcagtagaca gtccaagaa ccagttctcc      240 ctgaagctga actctgtgac cgccgcggac acggccgtgt attactgtgc gagaggcacc     300
gactggttcg acccctgggg ccagggaacc ctggtcaccg tctcctca                  348

<210> SEQ ID NO 53
<211> LENGTH: 324
<212> TYPE: DNA
<213> ORGANISM: Artificial sequence
<220> FEATURE:
<223> OTHER INFORMATION: Variable light chain of antibody #A08 hit

<400> SEQUENCE: 53
caggctgtgc tgactcagcc accctcggtg tcagtggccc caggacagac ggccaggatt      60
acctgtgggg aaacaacat tggaagtgaa agtgtgcact ggtaccaaca gaagccaggc     120
caggcccctg tgctggtcgt ctatgatgat agcgaccggc cctcagggat ccctgagcga     180
ttctctggct ccaactctgg gaacacggcc accctgacca tcagcagggt cgaagccggg     240
gatgaggccg actattactg tcaggtgtgg gatagtacta gtgatcatcg ggtattcggc     300
ggagggacca agctcaccgt ccta                                            324

<210> SEQ ID NO 54
<211> LENGTH: 348
<212> TYPE: DNA
<213> ORGANISM: Artificial sequence
<220> FEATURE:
<223> OTHER INFORMATION: Variable heavy chain of antibody #A08 lead

<400> SEQUENCE: 54
gaggtgcagc tgcaggagtc gggcccagga ctggtgaagc cttcggggac cctgtccctc      60
acctgcgctg tctctggtgg ctccatcagc agtaataact ggtggagttg ggtccgccag     120
```

```
cccccaggga aggggctgga gtggattggg gaaatctatc atagtgggag caccagctac    180
aacccgtccc tcaagagtcg agtcaccata tcagtagaca agtccaagaa ccagttctcc    240
ctgaagctgt cctctgtgac cgccgcggac acggccgtgt attactgtgc gagaggcacc    300
gactggttcg acccctgggg ccagggaacc ctggtcaccg tctcctca                 348
```

```
<210> SEQ ID NO 55
<211> LENGTH: 324
<212> TYPE: DNA
<213> ORGANISM: Artificial sequence
<220> FEATURE:
<223> OTHER INFORMATION: Variable light chain of antibody #A08 lead

<400> SEQUENCE: 55
tcctacgtgc tgactcagcc accctcggtg tcagtggccc caggacagac ggccaggatt    60
acctgtgggg gaaacaacat tggaagtgaa agtgtgcact ggtaccaaca gaagccaggc    120
caggcccctg tgctggtcgt ctatgatgat agcgaccggc cctcagggat ccctgagcga    180
ttctctggct ccaactctgg gaacacggcc accctgacca tcagcagggt cgaagccggg    240
gatgaggccg actattactg tcaggtgtgg gatagtacta gtgatcatcg ggtattcggc    300
ggagggacca gctcaccgt ccta                                            324
```

```
<210> SEQ ID NO 56
<211> LENGTH: 384
<212> TYPE: DNA
<213> ORGANISM: Artificial sequence
<220> FEATURE:
<223> OTHER INFORMATION: Variable heavy chain of antibody #A05 hit

<400> SEQUENCE: 56
caaatgcagc tggtacaatc tggggctgag gtgaagaagc ctggggcctc agtgaaggtc    60
tcctgcaagg cttctggaca caccttcacc ggctactata tgcactgggt gcgacaggcc    120
cctggacaag gcttgagtg gatgggatgg atcaacccta acagtggtgg cacaaactat    180
gcacagaagt ttcagggcag ggtcaccatg accagggaca cgtccatcag cacagcctac    240
atggagctga gcaggctgag atctgacgac acggccgtgt attactgtgc gagagatctt    300
ttctggtcct tgagcagtgg ctggtctatc catccgtact actttgacta ctggggccag    360
ggaaccctgg tcaccgtctc ctca                                           384
```

```
<210> SEQ ID NO 57
<211> LENGTH: 384
<212> TYPE: DNA
<213> ORGANISM: Artificial sequence
<220> FEATURE:
<223> OTHER INFORMATION: Variable heavy chain of antibody #A05 lead

<400> SEQUENCE: 57
gaggtgcagc tggtacaatc tggggctgag gtgaagaagc ctggggcctc agtgaaggtc    60
tcctgcaagg cttctggaca caccttcacc ggctactata tgcactgggt gcgacaggcc    120
cctggacaag gcttgagtg gatgggatgg atcaacccta acagtggtgg cacaaactat    180
gcacagaagt ttcagggcag ggtcaccatg accagggaca cgtccatcag cacagcctac    240
atggagctga gcaggctgag atctgacgac acggccgtgt attactgtgc gagagatctt    300
ttctggtcct tgagcagtgg ctggtctatc catccgtact actttgacta ctggggccag    360
ggaaccctgg tcaccgtctc ctca                                           384
```

```
<210> SEQ ID NO 58
<211> LENGTH: 327
<212> TYPE: DNA
<213> ORGANISM: Artificial sequence
<220> FEATURE:
<223> OTHER INFORMATION: Variable light chain of antibody #A05 hit

<400> SEQUENCE: 58
cagtctgccc tgactcagcc tgcctccgtg tctgggtctc ctggacagtc gatcaccatc      60
tcctgcactg gaaccagcag tgatgttggg agttataacc ttgtctcctg gtaccaacag     120
cacccaggca agccccccaa actcatgatt tatgggggca gtaagcggcc ctcaggggtc     180
cctgaccgat tctctggctc caagtctgac acctcagcct ccctgaccat ctctgggctc     240
caggctgagg acgaggctga ttattactgc tgctcatata catacaatgg ggatgtcttc     300
ggaactggga ccaaggtcac cgtccta                                         327

<210> SEQ ID NO 59
<211> LENGTH: 327
<212> TYPE: DNA
<213> ORGANISM: Artificial sequence
<220> FEATURE:
<223> OTHER INFORMATION: Variable light chain of antibody #A05 lead

<400> SEQUENCE: 59
cagtctgccc tgactcagcc tgcctccgtg tctgggtctc ctggacagtc gatcaccatc      60
tcctgcactg gaaccagcag tgatgttggg agttataacc ttgtctcctg gtaccaacag     120
cacccaggca agccccccaa actcatgatt tatgggggca gtaagcggcc ctcaggggtc     180
cctgaccgat tctctggctc caagtctggc aacaccgcct ccctgaccat ctctgggctc     240
caggctgagg acgaggctga ttattactgc agctcatata catacagcgg ggatgtcttc     300
ggaactggga ccaaggtcac cgtccta                                         327

<210> SEQ ID NO 60
<211> LENGTH: 8
<212> TYPE: PRT
<213> ORGANISM: Artificial sequence
<220> FEATURE:
<223> OTHER INFORMATION: CDR-1 of the heavy chain of antibodies #A05 hit
      and lead

<400> SEQUENCE: 60

Gly His Thr Phe Thr Gly Tyr Tyr
1               5

<210> SEQ ID NO 61
<211> LENGTH: 8
<212> TYPE: PRT
<213> ORGANISM: Artificial sequence
<220> FEATURE:
<223> OTHER INFORMATION: CDR-2 of the heavy chain of antibodies #A05 hit
      and lead

<400> SEQUENCE: 61

Ile Asn Pro Asn Ser Gly Gly Thr
1               5

<210> SEQ ID NO 62
<211> LENGTH: 21
<212> TYPE: PRT
<213> ORGANISM: Artificial sequence
<220> FEATURE:
<223> OTHER INFORMATION: CDR-3 of the heavy chain of antibodies #A05 hit
      and lead
```

<400> SEQUENCE: 62

Ala Arg Asp Leu Phe Trp Ser Leu Ser Ser Gly Trp Ser Ile His Pro
1               5                   10                  15

Tyr Tyr Phe Asp Tyr
            20

<210> SEQ ID NO 63
<211> LENGTH: 9
<212> TYPE: PRT
<213> ORGANISM: Artificial sequence
<220> FEATURE:
<223> OTHER INFORMATION: CDR-1 of the light chain of antibodies #A05 hit
      and lead

<400> SEQUENCE: 63

Ser Ser Asp Val Gly Ser Tyr Asn Leu
1               5

<210> SEQ ID NO 64
<211> LENGTH: 3
<212> TYPE: PRT
<213> ORGANISM: Artificial sequence
<220> FEATURE:
<223> OTHER INFORMATION: CDR-2 of the light chain of antibodies #A05 hit
      and lead

<400> SEQUENCE: 64

Gly Gly Ser
1

<210> SEQ ID NO 65
<211> LENGTH: 9
<212> TYPE: PRT
<213> ORGANISM: Artificial sequence
<220> FEATURE:
<223> OTHER INFORMATION: CDR-3 of the light chain of antibody #A05 hit

<400> SEQUENCE: 65

Cys Ser Tyr Thr Tyr Asn Gly Asp Val
1               5

<210> SEQ ID NO 66
<211> LENGTH: 9
<212> TYPE: PRT
<213> ORGANISM: Artificial sequence
<220> FEATURE:
<223> OTHER INFORMATION: CDR-3 of the light chain of antibody #A05 lead

<400> SEQUENCE: 66

Ser Ser Tyr Thr Tyr Ser Gly Asp Val
1               5

<210> SEQ ID NO 67
<211> LENGTH: 25
<212> TYPE: PRT
<213> ORGANISM: Artificial sequence
<220> FEATURE:
<223> OTHER INFORMATION: FR-1 of the heavy chain of antibody #A05 family
<220> FEATURE:
<221> NAME/KEY: MISC_FEATURE
<222> LOCATION: (1)..(1)
<223> OTHER INFORMATION: X in position 1 being any residues selected
      from the group consisting of Q and E
<220> FEATURE:
<221> NAME/KEY: MISC_FEATURE
<222> LOCATION: (2)..(2)
<223> OTHER INFORMATION: X in position 2 being any residues selected from the group consisting of Methionine (M) and V

<400> SEQUENCE: 67

Xaa Xaa Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 68
<211> LENGTH: 17
<212> TYPE: PRT
<213> ORGANISM: Artificial sequence
<220> FEATURE:
<223> OTHER INFORMATION: FR-2 of the heavy chain of antibody #A05 family

<400> SEQUENCE: 68

Met His Trp Val Arg Gln Ala Pro Gly Gln Gly Leu Glu Trp Met Gly
1               5                   10                  15

Trp

<210> SEQ ID NO 69
<211> LENGTH: 38
<212> TYPE: PRT
<213> ORGANISM: Artificial sequence
<220> FEATURE:
<223> OTHER INFORMATION: FR-3 of the heavy chain of antibody #A05 family

<400> SEQUENCE: 69

Asn Tyr Ala Gln Lys Phe Gln Gly Arg Val Thr Met Thr Arg Asp Thr
1               5                   10                  15

Ser Ile Ser Thr Ala Tyr Met Glu Leu Ser Arg Leu Arg Ser Asp Asp
            20                  25                  30

Thr Ala Val Tyr Tyr Cys
        35

<210> SEQ ID NO 70
<211> LENGTH: 11
<212> TYPE: PRT
<213> ORGANISM: Artificial sequence
<220> FEATURE:
<223> OTHER INFORMATION: FR-4 of the heavy chain of antibody #A05 family

<400> SEQUENCE: 70

Trp Gly Gln Gly Thr Leu Val Thr Val Ser Ser
1               5                   10

<210> SEQ ID NO 71
<211> LENGTH: 25
<212> TYPE: PRT
<213> ORGANISM: Artificial sequence
<220> FEATURE:
<223> OTHER INFORMATION: FR-1 of the light chain of antibody #A05 family

<400> SEQUENCE: 71

Gln Ser Ala Leu Thr Gln Pro Ala Ser Val Ser Gly Ser Pro Gly Gln
1               5                   10                  15

Ser Ile Thr Ile Ser Cys Thr Gly Thr
            20                  25

<210> SEQ ID NO 72
<211> LENGTH: 17
<212> TYPE: PRT
<213> ORGANISM: Artificial sequence
<220> FEATURE:

-continued

<223> OTHER INFORMATION: FR-2 of the light chain of antibody #A05 family

<400> SEQUENCE: 72

Val Ser Trp Tyr Gln Gln His Pro Gly Lys Ala Pro Lys Leu Met Ile
1               5                   10                  15
Tyr

<210> SEQ ID NO 73
<211> LENGTH: 36
<212> TYPE: PRT
<213> ORGANISM: Artificial sequence
<220> FEATURE:
<223> OTHER INFORMATION: FR-3 of the light chain of antibody #A05 family
<220> FEATURE:
<221> NAME/KEY: MISC_FEATURE
<222> LOCATION: (16)..(16)
<223> OTHER INFORMATION: X in position 16 being any residues selected
      from the group consisting of Aspartic acid (D) and Glycine (G)
<220> FEATURE:
<221> NAME/KEY: MISC_FEATURE
<222> LOCATION: (17)..(17)
<223> OTHER INFORMATION: X in position 17 being any residues selected
      from the group consisting of T and N
<220> FEATURE:
<221> NAME/KEY: MISC_FEATURE
<222> LOCATION: (18)..(18)
<223> OTHER INFORMATION: X in position 18 being any residues selected
      from the group consisting of S and T

<400> SEQUENCE: 73

Lys Arg Pro Ser Gly Val Pro Asp Arg Phe Ser Gly Ser Lys Ser Xaa
1               5                   10                  15
Xaa Xaa Ala Ser Leu Thr Ile Ser Gly Leu Gln Ala Glu Asp Glu Ala
            20                  25                  30
Asp Tyr Tyr Cys
        35

<210> SEQ ID NO 74
<211> LENGTH: 10
<212> TYPE: PRT
<213> ORGANISM: Artificial sequence
<220> FEATURE:
<223> OTHER INFORMATION: FR-4 of the light chain of antibody #A05 family

<400> SEQUENCE: 74

Phe Gly Thr Gly Thr Lys Val Thr Val Leu
1               5                   10

<210> SEQ ID NO 75
<211> LENGTH: 318
<212> TYPE: DNA
<213> ORGANISM: Artificial sequence
<220> FEATURE:
<223> OTHER INFORMATION: light chain constant region (lambda)

<400> SEQUENCE: 75
ggacagccca aggctgcccc ctcggtcact ctgttcccgc cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac acctccaaa     180 caaagcaaca caagtacgc ggccagcagc tacctgagcc tgacgcctga gcagtggaag     240
tcccacaaaa gctacagctg ccaggtcacg catgaaggga gcaccgtgga agacagtg      300 gcccctacag aatgttca                                                   318

```
<210> SEQ ID NO 76
<211> LENGTH: 987
<212> TYPE: DNA
<213> ORGANISM: Artificial sequence
<220> FEATURE:
<223> OTHER INFORMATION: heavy chain constant region ? human IgG1
      allotype G1m3

<400> SEQUENCE: 76
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctggggggga    360 ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc acgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc cccgggt                                         987

<210> SEQ ID NO 77
<211> LENGTH: 984
<212> TYPE: DNA
<213> ORGANISM: Artificial sequence
<220> FEATURE:
<223> OTHER INFORMATION: heavy chain constant region ? human IgG2
      allotype G2h

<400> SEQUENCE: 77
gctagcacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagccc     300
aaatcttctg acaaaactca cacatgccca ccgtgcccag caccacctgt ggcaggaccg     360
tcagtcttcc tcttcccccc aaaacccaag gacaccctca tgatctcccg gacccctgag     420
gtcacgtgcg tggtggtgga cgtgagccac gaagaccccg aggtccagtt caactggtac     480
gtggacggcg tggaggtgca taatgccaag acaaagccac gggaggagca gcccagagc      540 acgttccgtg tggtcagcgt cctcaccgtt gtgcaccagg actggctgaa cggcaaggag     600
tacaagtgcg ctgtctccaa caaaggcctc ccagccccca tcgagaaaac catctccaaa     660
accaaagggc agccccgaga accacaggtg tacaccctgc cccatcacg ggaggagatg      720
```

| | |
|---|---|
| accaagaacc aggtcagcct gacctgcctg gtcaaaggct tctaccccag cgacatcgcc | 780 |
| gtggagtggg agagcaatgg gcagccggag aacaactaca agaccacacc tcccatgctg | 840 |
| gactccgacg gctccttctt cctctacagc aagctcaccg tggacaagag caggtggcag | 900 |
| caggggaacg tcttctcatg ctccgtgatg catgaggctc tgcacaacca ctacacacag | 960 |
| aagagcctct ccctgtcccc gggt | 984 |

<210> SEQ ID NO 78
<211> LENGTH: 996
<212> TYPE: DNA
<213> ORGANISM: Artificial sequence
<220> FEATURE:
<223> OTHER INFORMATION: heavy chain constant region ? SEED(AG)

<400> SEQUENCE: 78

| | |
|---|---|
| gctagcacca agggcccatc ggtcttcccc ctggcaccct cctccaagag cacctctggg | 60 |
| ggcacagcgg ccctgggctg cctggtcaag gactacttcc ccgaaccggt gacggtgtcg | 120 |
| tggaactcag gcgccctgac cagcggcgtg cacaccttcc cggctgtcct acagtcctca | 180 |
| ggactctact ccctcagcag cgtggtgacc gtgccctcca gcagcttggg cacccagacc | 240 |
| tacatctgca acgtgaatca caagcccagc aacaccaagg tggacaagag agttgagccc | 300 |
| aaatcttgtg acaaaactca cacatgccca ccgtgcccag cacctgaact cctgggggga | 360 |
| ccctcagtct tcctcttccc cccaaaaccc aaggacaccc tcatgatctc tagaacccct | 420 |
| gaggtcacat gcgtggtggt ggacgtgagc cacgaagacc ctgaggtcaa gttcaactgg | 480 |
| tacgtggacg gcgtggaggt gcataatgcc aagacaaagc cgcgggagga gcagtacaac | 540 |
| agcacgtacc gtgtggtcag cgtcctcacc gtcctgcacc aggactggct gaatggcaag | 600 |
| gagtacaagt gcaaggtctc caacaaagcc ctcccagccc ccatcgagaa aacgatatcc | 660 |
| aaagccaaag ggcagcccct tccggccaga gtccacctgc tgcccccatc acgggaggag | 720 |
| atgaccaaga accaggtcag cctgacctgc ctggcacgcg gcttctatcc caaggacatc | 780 |
| gccgtggagt gggagagcaa tgggcagccg gagaacaact acaagaccac gccttcccgg | 840 |
| caggagccca gccagggcac caccaccttc gctgtgacct cgaagctcac cgtggacaag | 900 |
| agcagatggc agcaggggaa cgtcttctca tgctccgtga tgcatgaggc tctgcacaac | 960 |
| cactacacgc agaagaccat ctccctgtcc ccgggt | 996 |

<210> SEQ ID NO 79
<211> LENGTH: 702
<212> TYPE: DNA
<213> ORGANISM: Artificial sequence
<220> FEATURE:
<223> OTHER INFORMATION: heavy chain constant region ? SEED(GA)

<400> SEQUENCE: 79

| | |
|---|---|
| gagcccaaat cttctgacaa aactcacaca tgcccaccgt gcccagcacc tgaactcctg | 60 |
| ggggggccct cagtcttcct cttcccccca aaacccaagg acaccctcat gatctctaga | 120 |
| acccctgagg tcacatgcgt ggtggtggac gtgagccacg aagaccctga ggtcaagttc | 180 |
| aactggtacg tggacggcgt ggaggtgcat aatgccaaga caaagccgcg ggaggagcag | 240 |
| tacaacagca cgtaccgtgt ggtcagcgtc ctcaccgtcc tgcaccagga ctggctgaat | 300 |
| ggcaaggagt acaagtgcaa ggtctccaac aaagccctcc cagcccccat cgagaaaacg | 360 |
| atatccaaag ccaaagggca gccccgagaa ccacaggtgt acaccctgcc cccaccgtcg | 420 |
| gaggagctgg ccctgaacga gctggtgacg ctgacctgcc tggtcaaagg cttctatccc | 480 | agcgacatcg ccgtggagtg gctgcagggg tcccaggagc tgccccgcga gaagtacctg 540 acttgggcac ccgtgctgga ctccgacggc tccttcttcc tctatagtat actgcgcgtg 600 gcagccgagg actggaagaa gggggacacc ttctcatgct ccgtgatgca tgaggctctg 660 cacaaccact acacgcagaa gagcctcgac cgctccccgg gt 702

<210> SEQ ID NO 80
<211> LENGTH: 263
<212> TYPE: PRT
<213> ORGANISM: Homo sapiens
<220> FEATURE:
<223> OTHER INFORMATION: human FGFR1b-IIIb extracellular domain

<400> SEQUENCE: 80

```
Arg Pro Ser Pro Thr Leu Pro Glu Gln Asp Ala Leu Pro Ser Ser Glu
1               5                   10                  15

Asp Asp Asp Asp Asp Asp Ser Ser Ser Glu Glu Lys Glu Thr Asp
                20                  25                  30

Asn Thr Lys Pro Asn Pro Val Ala Pro Tyr Trp Thr Ser Pro Glu Lys
            35                  40                  45

Met Glu Lys Lys Leu His Ala Val Pro Ala Ala Lys Thr Val Lys Phe
    50                  55                  60

Lys Cys Pro Ser Ser Gly Thr Pro Asn Pro Thr Leu Arg Trp Leu Lys
65                  70                  75                  80

Asn Gly Lys Glu Phe Lys Pro Asp His Arg Ile Gly Gly Tyr Lys Val
                85                  90                  95

Arg Tyr Ala Thr Trp Ser Ile Ile Met Asp Ser Val Val Pro Ser Asp
            100                 105                 110

Lys Gly Asn Tyr Thr Cys Ile Val Glu Asn Glu Tyr Gly Ser Ile Asn
        115                 120                 125

His Thr Tyr Gln Leu Asp Val Val Glu Arg Ser Pro His Arg Pro Ile
    130                 135                 140

Leu Gln Ala Gly Leu Pro Ala Asn Lys Thr Val Ala Leu Gly Ser Asn
145                 150                 155                 160

Val Glu Phe Met Cys Lys Val Tyr Ser Asp Pro Gln Pro His Ile Gln
                165                 170                 175

Trp Leu Lys His Ile Glu Val Asn Gly Ser Lys Ile Gly Pro Asp Asn
            180                 185                 190

Leu Pro Tyr Val Gln Ile Leu Lys His Ser Gly Ile Asn Ser Ser Asp
        195                 200                 205

Ala Glu Val Leu Thr Leu Phe Asn Val Thr Glu Ala Gln Ser Gly Glu
    210                 215                 220

Tyr Val Cys Lys Val Ser Asn Tyr Ile Gly Glu Ala Asn Gln Ser Ala
225                 230                 235                 240

Trp Leu Thr Val Thr Arg Pro Ala Leu Glu Glu Arg Pro Ala Val Met
                245                 250                 255

Thr Ser Pro Leu Tyr Leu Glu
            260
```

<210> SEQ ID NO 81
<211> LENGTH: 264
<212> TYPE: PRT
<213> ORGANISM: Homo sapiens
<220> FEATURE:
<223> OTHER INFORMATION: human FGFR1b-IIIc extracellular domain

<400> SEQUENCE: 81

Arg Pro Ser Pro Thr Leu Pro Glu Gln Asp Ala Leu Pro Ser Ser Glu
1               5                   10                  15

Asp Asp Asp Asp Asp Asp Ser Ser Glu Lys Glu Thr Asp
            20              25              30

Asn Thr Lys Pro Asn Pro Val Ala Pro Tyr Trp Thr Ser Pro Glu Lys
        35              40                  45

Met Glu Lys Lys Leu His Ala Val Pro Ala Ala Lys Thr Val Lys Phe
    50              55                  60

Lys Cys Pro Ser Ser Gly Thr Pro Asn Pro Thr Leu Arg Trp Leu Lys
65              70                  75                  80

Asn Gly Lys Glu Phe Lys Pro Asp His Arg Ile Gly Gly Tyr Lys Val
            85                  90                  95

Arg Tyr Ala Thr Trp Ser Ile Ile Met Asp Ser Val Val Pro Ser Asp
            100                 105                 110

Lys Gly Asn Tyr Thr Cys Ile Val Glu Asn Glu Tyr Gly Ser Ile Asn
            115                 120                 125

His Thr Tyr Gln Leu Asp Val Val Glu Arg Ser Pro His Arg Pro Ile
    130                 135                 140

Leu Gln Ala Gly Leu Pro Ala Asn Lys Thr Val Ala Leu Gly Ser Asn
145                 150                 155                 160

Val Glu Phe Met Cys Lys Val Tyr Ser Asp Pro Gln Pro His Ile Gln
            165                 170                 175

Trp Leu Lys His Ile Glu Val Asn Gly Ser Lys Ile Gly Pro Asp Asn
            180                 185                 190

Leu Pro Tyr Val Gln Ile Leu Lys Thr Ala Gly Val Asn Thr Thr Asp
            195                 200                 205

Lys Glu Met Glu Val Leu His Leu Arg Asn Val Ser Phe Glu Asp Ala
    210                 215                 220

Gly Glu Tyr Thr Cys Leu Ala Gly Asn Ser Ile Gly Leu Ser His His
225                 230                 235                 240

Ser Ala Trp Leu Thr Val Leu Glu Ala Leu Glu Glu Arg Pro Ala Val
            245                 250                 255

Met Thr Ser Pro Leu Tyr Leu Glu
            260

<210> SEQ ID NO 82
<211> LENGTH: 266
<212> TYPE: PRT
<213> ORGANISM: Mus musculus
<220> FEATURE:
<223> OTHER INFORMATION: mouse FGFR1b-IIIb extracellular domain

<400> SEQUENCE: 82

Arg Pro Ala Pro Thr Leu Pro Glu Gln Asp Ala Leu Pro Ser Ser Glu
1               5                   10                  15

Asp Asp Asp Asp Asp Asp Ser Ser Ser Glu Glu Lys Glu Thr Asp
            20              25              30

Asn Thr Lys Pro Asn Pro Val Ala Pro Tyr Trp Thr Ser Pro Glu Lys
        35              40                  45

Met Glu Lys Lys Leu His Ala Val Pro Ala Ala Lys Thr Val Lys Phe
    50              55                  60

Lys Cys Pro Ser Ser Gly Thr Pro Asn Pro Thr Leu Arg Trp Leu Lys
65              70                  75                  80

Asn Gly Lys Glu Phe Lys Pro Asp His Arg Ile Gly Gly Tyr Lys Val
            85                  90                  95

```
Arg Tyr Ala Thr Trp Ser Ile Ile Met Asp Ser Val Pro Ser Asp
            100                 105                 110

Lys Gly Asn Tyr Thr Cys Ile Val Glu Asn Glu Tyr Gly Ser Ile Asn
            115                 120                 125

His Thr Tyr Gln Leu Asp Val Val Glu Arg Ser Pro His Arg Pro Ile
        130                 135                 140

Leu Gln Ala Gly Leu Pro Ala Asn Lys Thr Val Ala Leu Gly Ser Asn
145                 150                 155                 160

Val Glu Phe Met Cys Lys Val Tyr Ser Asp Pro Gln Pro His Ile Gln
                165                 170                 175

Trp Leu Lys His Ile Glu Val Asn Gly Ser Lys Ile Gly Pro Asp Asn
            180                 185                 190

Leu Pro Tyr Val Gln Ile Leu Lys His Ser Gly Ile Asn Ser Ser Asp
        195                 200                 205

Ala Glu Val Leu Thr Leu Phe Asn Val Thr Glu Ala Gln Ser Gly Glu
    210                 215                 220

Tyr Val Cys Lys Val Ser Asn Tyr Ile Gly Glu Ala Asn Gln Ser Ala
225                 230                 235                 240

Trp Leu Thr Val Thr Arg Pro Val Ala Lys Ala Leu Glu Glu Arg Pro
                245                 250                 255

Ala Val Met Thr Ser Pro Leu Tyr Leu Glu
            260                 265

<210> SEQ ID NO 83
<211> LENGTH: 264
<212> TYPE: PRT
<213> ORGANISM: Mus musculus
<220> FEATURE:
<223> OTHER INFORMATION: mouse FGFR1b-IIIc extracellular domain

<400> SEQUENCE: 83

Arg Pro Ala Pro Thr Leu Pro Glu Gln Asp Ala Leu Pro Ser Ser Glu
1               5                   10                  15

Asp Asp Asp Asp Asp Asp Ser Ser Ser Glu Glu Lys Glu Thr Asp
            20                  25                  30

Asn Thr Lys Pro Asn Pro Val Ala Pro Tyr Trp Thr Ser Pro Glu Lys
        35                  40                  45

Met Glu Lys Lys Leu His Ala Val Pro Ala Ala Lys Thr Val Lys Phe
    50                  55                  60

Lys Cys Pro Ser Ser Gly Thr Pro Asn Pro Thr Leu Arg Trp Leu Lys
65                  70                  75                  80

Asn Gly Lys Glu Phe Lys Pro Asp His Arg Ile Gly Gly Tyr Lys Val
                85                  90                  95

Arg Tyr Ala Thr Trp Ser Ile Ile Met Asp Ser Val Pro Ser Asp
            100                 105                 110

Lys Gly Asn Tyr Thr Cys Ile Val Glu Asn Glu Tyr Gly Ser Ile Asn
            115                 120                 125

His Thr Tyr Gln Leu Asp Val Val Glu Arg Ser Pro His Arg Pro Ile
        130                 135                 140

Leu Gln Ala Gly Leu Pro Ala Asn Lys Thr Val Ala Leu Gly Ser Asn
145                 150                 155                 160

Val Glu Phe Met Cys Lys Val Tyr Ser Asp Pro Gln Pro His Ile Gln
                165                 170                 175

Trp Leu Lys His Ile Glu Val Asn Gly Ser Lys Ile Gly Pro Asp Asn
            180                 185                 190
```

-continued

```
Leu Pro Tyr Val Gln Ile Leu Lys Thr Ala Gly Val Asn Thr Thr Asp
        195                 200                 205

Lys Glu Met Glu Val Leu His Leu Arg Asn Val Ser Phe Glu Asp Ala
    210                 215                 220

Gly Glu Tyr Thr Cys Leu Ala Gly Asn Ser Ile Gly Leu Ser His His
225                 230                 235                 240

Ser Ala Trp Leu Thr Val Leu Glu Ala Leu Glu Glu Arg Pro Ala Val
            245                 250                 255

Met Thr Ser Pro Leu Tyr Leu Glu
        260

<210> SEQ ID NO 84
<211> LENGTH: 148
<212> TYPE: PRT
<213> ORGANISM: Artificial
<220> FEATURE:
<223> OTHER INFORMATION: Artificial sequence

<400> SEQUENCE: 84

Arg Pro Ser Pro Thr Leu Pro Glu Gln Asp Ala Leu Pro Ser Ser Glu
1               5                   10                  15

Asp Asp Asp Asp Asp Asp Ser Ser Ser Glu Glu Lys Glu Thr Asp
            20                  25                  30

Asn Thr Lys Pro Asn Pro Val Ala Pro Tyr Trp Thr Ser Pro Glu Lys
        35                  40                  45

Met Glu Lys Lys Leu His Ala Val Pro Ala Ala Lys Thr Val Lys Phe
    50                  55                  60

Lys Cys Pro Ser Ser Gly Thr Pro Asn Pro Thr Leu Arg Trp Leu Lys
65                  70                  75                  80

Asn Gly Lys Glu Phe Lys Pro Asp His Arg Ile Gly Gly Tyr Lys Val
                85                  90                  95

Arg Tyr Ala Thr Trp Ser Ile Ile Met Asp Ser Val Val Pro Ser Asp
            100                 105                 110

Lys Gly Asn Tyr Thr Cys Ile Val Glu Asn Glu Tyr Gly Ser Ile Asn
        115                 120                 125

His Thr Tyr Gln Leu Asp Val Val Glu Arg Ser Pro His Arg His His
    130                 135                 140

His His His His
145

<210> SEQ ID NO 85
<211> LENGTH: 129
<212> TYPE: PRT
<213> ORGANISM: Artificial sequence
<220> FEATURE:
<223> OTHER INFORMATION: Human FGFR1-IIIc D3-His6

<400> SEQUENCE: 85

Arg Pro Ile Leu Gln Ala Gly Leu Pro Ala Asn Lys Thr Val Ala Leu
1               5                   10                  15

Gly Ser Asn Val Glu Phe Met Cys Lys Val Tyr Ser Asp Pro Gln Pro
            20                  25                  30

His Ile Gln Trp Leu Lys His Ile Glu Val Asn Gly Ser Lys Ile Gly
        35                  40                  45

Pro Asp Asn Leu Pro Tyr Val Gln Ile Leu Lys Thr Ala Gly Val Asn
    50                  55                  60

Thr Thr Asp Lys Glu Met Glu Val Leu His Leu Arg Asn Val Ser Phe
```

```
               65                  70                  75                  80
Glu Asp Ala Gly Glu Tyr Thr Cys Leu Ala Gly Asn Ser Ile Gly Leu
                    85                  90                  95

Ser His His Ser Ala Trp Leu Thr Val Leu Glu Ala Leu Glu Glu Arg
                100                 105                 110

Pro Ala Val Met Thr Ser Pro Leu Tyr Leu Glu His His His His
            115                 120                 125

His

<210> SEQ ID NO 86
<211> LENGTH: 269
<212> TYPE: PRT
<213> ORGANISM: Artificial sequence
<220> FEATURE:
<223> OTHER INFORMATION: human FGFR1b-IIIb extracellular domain with a
      HIS tag

<400> SEQUENCE: 86

Arg Pro Ser Pro Thr Leu Pro Glu Gln Asp Ala Leu Pro Ser Ser Glu
1               5                   10                  15

Asp Asp Asp Asp Asp Asp Ser Ser Ser Glu Glu Lys Glu Thr Asp
                20                  25                  30

Asn Thr Lys Pro Asn Pro Val Ala Pro Tyr Trp Thr Ser Pro Glu Lys
            35                  40                  45

Met Glu Lys Lys Leu His Ala Val Pro Ala Ala Lys Thr Val Lys Phe
    50                  55                  60

Lys Cys Pro Ser Ser Gly Thr Pro Asn Pro Thr Leu Arg Trp Leu Lys
65                  70                  75                  80

Asn Gly Lys Glu Phe Lys Pro Asp His Arg Ile Gly Gly Tyr Lys Val
                85                  90                  95

Arg Tyr Ala Thr Trp Ser Ile Ile Met Asp Ser Val Val Pro Ser Asp
            100                 105                 110

Lys Gly Asn Tyr Thr Cys Ile Val Glu Asn Glu Tyr Gly Ser Ile Asn
        115                 120                 125

His Thr Tyr Gln Leu Asp Val Val Glu Arg Ser Pro His Arg Pro Ile
130                 135                 140

Leu Gln Ala Gly Leu Pro Ala Asn Lys Thr Val Ala Leu Gly Ser Asn
145                 150                 155                 160

Val Glu Phe Met Cys Lys Val Tyr Ser Asp Pro Gln Pro His Ile Gln
                165                 170                 175

Trp Leu Lys His Ile Glu Val Asn Gly Ser Lys Ile Gly Pro Asp Asn
            180                 185                 190

Leu Pro Tyr Val Gln Ile Leu Lys His Ser Gly Ile Asn Ser Ser Asp
        195                 200                 205

Ala Glu Val Leu Thr Leu Phe Asn Val Thr Glu Ala Gln Ser Gly Glu
    210                 215                 220

Tyr Val Cys Lys Val Ser Asn Tyr Ile Gly Glu Ala Asn Gln Ser Ala
225                 230                 235                 240

Trp Leu Thr Val Thr Arg Pro Ala Leu Glu Glu Arg Pro Ala Val Met
                245                 250                 255

Thr Ser Pro Leu Tyr Leu Glu His His His His His
            260                 265

<210> SEQ ID NO 87
<211> LENGTH: 270
<212> TYPE: PRT
```

<213> ORGANISM: Artificial sequence
<220> FEATURE:
<223> OTHER INFORMATION: human FGFR1b-IIIc extracellular domain with a HIS tag

<400> SEQUENCE: 87

```
Arg Pro Ser Pro Thr Leu Pro Glu Gln Asp Ala Leu Pro Ser Ser Glu
1               5                  10                  15
Asp Asp Asp Asp Asp Asp Ser Ser Glu Glu Lys Glu Thr Asp
            20                  25                  30
Asn Thr Lys Pro Asn Pro Val Ala Pro Tyr Trp Thr Ser Pro Glu Lys
        35                  40                  45
Met Glu Lys Lys Leu His Ala Val Pro Ala Ala Lys Thr Val Lys Phe
    50                  55                  60
Lys Cys Pro Ser Ser Gly Thr Pro Asn Pro Thr Leu Arg Trp Leu Lys
65                  70                  75                  80
Asn Gly Lys Glu Phe Lys Pro Asp His Arg Ile Gly Gly Tyr Lys Val
                85                  90                  95
Arg Tyr Ala Thr Trp Ser Ile Ile Met Asp Ser Val Val Pro Ser Asp
            100                 105                 110
Lys Gly Asn Tyr Thr Cys Ile Val Glu Asn Glu Tyr Gly Ser Ile Asn
        115                 120                 125
His Thr Tyr Gln Leu Asp Val Val Glu Arg Ser Pro His Arg Pro Ile
    130                 135                 140
Leu Gln Ala Gly Leu Pro Ala Asn Lys Thr Val Ala Leu Gly Ser Asn
145                 150                 155                 160
Val Glu Phe Met Cys Lys Val Tyr Ser Asp Pro Gln Pro His Ile Gln
                165                 170                 175
Trp Leu Lys His Ile Glu Val Asn Gly Ser Lys Ile Gly Pro Asp Asn
            180                 185                 190
Leu Pro Tyr Val Gln Ile Leu Lys Thr Ala Gly Val Asn Thr Thr Asp
        195                 200                 205
Lys Glu Met Glu Val Leu His Leu Arg Asn Val Ser Phe Glu Asp Ala
    210                 215                 220
Gly Glu Tyr Thr Cys Leu Ala Gly Asn Ser Ile Gly Leu Ser His His
225                 230                 235                 240
Ser Ala Trp Leu Thr Val Leu Glu Ala Leu Glu Glu Arg Pro Ala Val
                245                 250                 255
Met Thr Ser Pro Leu Tyr Leu Glu His His His His His His
            260                 265                 270
```

<210> SEQ ID NO 88
<211> LENGTH: 272
<212> TYPE: PRT
<213> ORGANISM: Artificial sequence
<220> FEATURE:
<223> OTHER INFORMATION: mouse FGFR1b-IIIb extracellular domain with His tag

<400> SEQUENCE: 88

```
Arg Pro Ala Pro Thr Leu Pro Glu Gln Asp Ala Leu Pro Ser Ser Glu
1               5                  10                  15
Asp Asp Asp Asp Asp Asp Ser Ser Ser Glu Glu Lys Glu Thr Asp
            20                  25                  30
Asn Thr Lys Pro Asn Pro Val Ala Pro Tyr Trp Thr Ser Pro Glu Lys
        35                  40                  45
Met Glu Lys Lys Leu His Ala Val Pro Ala Ala Lys Thr Val Lys Phe
```

```
            50                  55                  60
Lys Cys Pro Ser Ser Gly Thr Pro Asn Pro Thr Leu Arg Trp Leu Lys
 65                  70                  75                  80

Asn Gly Lys Glu Phe Lys Pro Asp His Arg Ile Gly Gly Tyr Lys Val
                 85                  90                  95

Arg Tyr Ala Thr Trp Ser Ile Ile Met Asp Ser Val Val Pro Ser Asp
                100                 105                 110

Lys Gly Asn Tyr Thr Cys Ile Val Glu Asn Glu Tyr Gly Ser Ile Asn
                115                 120                 125

His Thr Tyr Gln Leu Asp Val Val Glu Arg Ser Pro His Arg Pro Ile
            130                 135                 140

Leu Gln Ala Gly Leu Pro Ala Asn Lys Thr Val Ala Leu Gly Ser Asn
145                 150                 155                 160

Val Glu Phe Met Cys Lys Val Tyr Ser Asp Pro Gln Pro His Ile Gln
                165                 170                 175

Trp Leu Lys His Ile Glu Val Asn Gly Ser Lys Ile Gly Pro Asp Asn
                180                 185                 190

Leu Pro Tyr Val Gln Ile Leu Lys His Ser Gly Ile Asn Ser Ser Asp
                195                 200                 205

Ala Glu Val Leu Thr Leu Phe Asn Val Thr Glu Ala Gln Ser Gly Glu
            210                 215                 220

Tyr Val Cys Lys Val Ser Asn Tyr Ile Gly Glu Ala Asn Gln Ser Ala
225                 230                 235                 240

Trp Leu Thr Val Thr Arg Pro Val Ala Lys Ala Leu Glu Glu Arg Pro
                245                 250                 255

Ala Val Met Thr Ser Pro Leu Tyr Leu Glu His His His His His His
                260                 265                 270

<210> SEQ ID NO 89
<211> LENGTH: 270
<212> TYPE: PRT
<213> ORGANISM: Artificial sequence
<220> FEATURE:
<223> OTHER INFORMATION: mouse FGFR1b-IIIc extracellular domain with His
      tag

<400> SEQUENCE: 89

Arg Pro Ala Pro Thr Leu Pro Glu Gln Asp Ala Leu Pro Ser Ser Glu
 1               5                  10                  15

Asp Asp Asp Asp Asp Asp Ser Ser Ser Glu Glu Lys Glu Thr Asp Asn
                20                  25                  30

Asn Thr Lys Pro Asn Pro Val Ala Pro Tyr Trp Thr Ser Pro Glu Lys
                35                  40                  45

Met Glu Lys Lys Leu His Ala Val Pro Ala Ala Lys Thr Val Lys Phe
 50                  55                  60

Lys Cys Pro Ser Ser Gly Thr Pro Asn Pro Thr Leu Arg Trp Leu Lys
 65                  70                  75                  80

Asn Gly Lys Glu Phe Lys Pro Asp His Arg Ile Gly Gly Tyr Lys Val
                 85                  90                  95

Arg Tyr Ala Thr Trp Ser Ile Ile Met Asp Ser Val Val Pro Ser Asp
                100                 105                 110

Lys Gly Asn Tyr Thr Cys Ile Val Glu Asn Glu Tyr Gly Ser Ile Asn
                115                 120                 125

His Thr Tyr Gln Leu Asp Val Val Glu Arg Ser Pro His Arg Pro Ile
            130                 135                 140
```

```
Leu Gln Ala Gly Leu Pro Ala Asn Lys Thr Val Ala Leu Gly Ser Asn
145                 150                 155                 160

Val Glu Phe Met Cys Lys Val Tyr Ser Asp Pro Gln Pro His Ile Gln
                165                 170                 175

Trp Leu Lys His Ile Glu Val Asn Gly Ser Lys Ile Gly Pro Asp Asn
            180                 185                 190

Leu Pro Tyr Val Gln Ile Leu Lys Thr Ala Gly Val Asn Thr Thr Asp
        195                 200                 205

Lys Glu Met Glu Val Leu His Leu Arg Asn Val Ser Phe Glu Asp Ala
    210                 215                 220

Gly Glu Tyr Thr Cys Leu Ala Gly Asn Ser Ile Gly Leu Ser His His
225                 230                 235                 240

Ser Ala Trp Leu Thr Val Leu Glu Ala Leu Glu Glu Arg Pro Ala Val
                245                 250                 255

Met Thr Ser Pro Leu Tyr Leu Glu His His His His His
            260                 265                 270

<210> SEQ ID NO 90
<211> LENGTH: 9
<212> TYPE: PRT
<213> ORGANISM: artificial
<220> FEATURE:
<223> OTHER INFORMATION: alternative CDR-3 of the heavy chain of
      antibody #A08 hit
<220> FEATURE:
<221> NAME/KEY: misc_feature
<222> LOCATION: (3)..(3)
<223> OTHER INFORMATION: Xaa can be any one of S, G, A or V
<220> FEATURE:
<221> NAME/KEY: misc_feature
<222> LOCATION: (4)..(4)
<223> OTHER INFORMATION: Xaa can be any one of T or K
<220> FEATURE:
<221> NAME/KEY: misc_feature
<222> LOCATION: (7)..(7)
<223> OTHER INFORMATION: Xaa can be any one of F, Y or I
<220> FEATURE:
<221> NAME/KEY: misc_feature
<222> LOCATION: (9)..(9)
<223> OTHER INFORMATION: Xaa can be any one of P, L, A, T or H

<400> SEQUENCE: 90

Ala Arg Xaa Xaa Asp Trp Xaa Asp Xaa
1               5

<210> SEQ ID NO 91
<211> LENGTH: 116
<212> TYPE: PRT
<213> ORGANISM: artificial
<220> FEATURE:
<223> OTHER INFORMATION: Alternative variable heavy chain of antibody
      #A08
<220> FEATURE:
<221> NAME/KEY: misc_feature
<222> LOCATION: (1)..(1)
<223> OTHER INFORMATION: Xaa can be any one of E or Q
<220> FEATURE:
<221> NAME/KEY: misc_feature
<222> LOCATION: (99)..(99)
<223> OTHER INFORMATION: Xaa can be any one of S, G, A or V
<220> FEATURE:
<221> NAME/KEY: misc_feature
<222> LOCATION: (100)..(100)
<223> OTHER INFORMATION: Xaa can be any one of T or K
<220> FEATURE:
<221> NAME/KEY: misc_feature
<222> LOCATION: (103)..(103)
<223> OTHER INFORMATION: Xaa can be any one of F, Y or I
<220> FEATURE:
```

```
<221> NAME/KEY: misc_feature
<222> LOCATION: (105)..(105)
<223> OTHER INFORMATION: Xaa can be any one of P, L, A, T or H

<400> SEQUENCE: 91

Xaa Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Ser Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Asn Ser Val Thr Ala Ala Asp Thr Ala Val Tyr Tyr Cys
                85                  90                  95

Ala Arg Xaa Xaa Asp Trp Xaa Asp Xaa Trp Gly Gln Gly Thr Leu Val
            100                 105                 110

Thr Val Ser Ser
        115

<210> SEQ ID NO 92
<211> LENGTH: 116
<212> TYPE: PRT
<213> ORGANISM: artificial
<220> FEATURE:
<223> OTHER INFORMATION: variable heavy chain for #B10-SEED(AG) antibody

<400> SEQUENCE: 92

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Ser Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ala Thr Asp Trp Tyr Asp Pro Trp Gly Gln Gly Thr Leu Val
            100                 105                 110

Thr Val Ser Ser
        115

<210> SEQ ID NO 93
<211> LENGTH: 116
<212> TYPE: PRT
<213> ORGANISM: artificial
<220> FEATURE:
<223> OTHER INFORMATION: variable heavy chain for #A02-SEED(AG) antibody

<400> SEQUENCE: 93

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30
```

Asn Trp Trp Ser Trp Val Arg Gln Pro Pro Gly Lys Gly Leu Glu Trp
            35                  40                  45

Ile Gly Glu Ile Tyr His Ser Gly Ser Thr Ser Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ala Thr Asp Trp Phe Asp Leu Trp Gly Gln Gly Thr Leu Val
            100                 105                 110

Thr Val Ser Ser
            115

<210> SEQ ID NO 94
<211> LENGTH: 116
<212> TYPE: PRT
<213> ORGANISM: artificial
<220> FEATURE:
<223> OTHER INFORMATION: variable heavy chain for #G04-SEED(AG) antibody

<400> SEQUENCE: 94

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Ser Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Thr Asp Trp Tyr Asp Leu Trp Gly Gln Gly Thr Leu Val
            100                 105                 110

Thr Val Ser Ser
            115

<210> SEQ ID NO 95
<211> LENGTH: 116
<212> TYPE: PRT
<213> ORGANISM: artificial
<220> FEATURE:
<223> OTHER INFORMATION: variable heavy chain for #D02-SEED(AG) antibody

<400> SEQUENCE: 95

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Ser Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys 85                  90                  95

Ala Arg Gly Thr Asp Trp Ile Asp Thr Trp Gly Gln Gly Thr Leu Val
               100                 105                 110

Thr Val Ser Ser
       115

<210> SEQ ID NO 96
<211> LENGTH: 116
<212> TYPE: PRT
<213> ORGANISM: artificial
<220> FEATURE:
<223> OTHER INFORMATION: variable heavy chain for #D01-SEED(AG) antibody

<400> SEQUENCE: 96

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Ser Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ala Thr Asp Trp Phe Asp His Trp Gly Gln Gly Thr Leu Val
               100                 105                 110

Thr Val Ser Ser
       115

<210> SEQ ID NO 97
<211> LENGTH: 116
<212> TYPE: PRT
<213> ORGANISM: artificial
<220> FEATURE:
<223> OTHER INFORMATION: variable heavy chain for #C01-SEED(AG) antibody

<400> SEQUENCE: 97

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Ser Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ala Thr Asp Trp Phe Asp Ala Trp Gly Gln Gly Thr Leu Val
               100                 105                 110

Thr Val Ser Ser
       115

<210> SEQ ID NO 98
<211> LENGTH: 116

```
<212> TYPE: PRT
<213> ORGANISM: artificial
<220> FEATURE:
<223> OTHER INFORMATION: variable heavy chain for #A07-SEED(AG) antibody

<400> SEQUENCE: 98

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Ser Tyr Asn Pro Ser Leu
50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Thr Asp Trp Tyr Asp Pro Trp Gly Gln Gly Thr Leu Val
            100                 105                 110

Thr Val Ser Ser
        115

<210> SEQ ID NO 99
<211> LENGTH: 448
<212> TYPE: PRT
<213> ORGANISM: artificial
<220> FEATURE:
<223> OTHER INFORMATION: alternative heavy chain for #A08 lead-SEED(AG)
      antibody
<220> FEATURE:
<221> NAME/KEY: misc_feature
<222> LOCATION: (1)..(1)
<223> OTHER INFORMATION: Xaa can be any one of E or Q
<220> FEATURE:
<221> NAME/KEY: misc_feature
<222> LOCATION: (99)..(99)
<223> OTHER INFORMATION: Xaa can be any one of S, G, A or V
<220> FEATURE:
<221> NAME/KEY: misc_feature
<222> LOCATION: (100)..(100)
<223> OTHER INFORMATION: Xaa can be any one of T or K
<220> FEATURE:
<221> NAME/KEY: misc_feature
<222> LOCATION: (103)..(103)
<223> OTHER INFORMATION: Xaa can be any one of F, Y or I
<220> FEATURE:
<221> NAME/KEY: misc_feature
<222> LOCATION: (105)..(105)
<223> OTHER INFORMATION: Xaa can be any one of P, L, A, T or H

<400> SEQUENCE: 99

Xaa Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Ser Tyr Asn Pro Ser Leu
50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95
```

```
Ala Arg Xaa Xaa Asp Trp Xaa Asp Xaa Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Phe Arg Pro Glu Val His Leu Leu Pro Pro
            340                 345                 350

Ser Arg Glu Glu Met Thr Lys Asn Gln Val Ser Leu Thr Cys Leu Ala
            355                 360                 365

Arg Gly Phe Tyr Pro Lys Asp Ile Ala Val Glu Trp Glu Ser Asn Gly
            370                 375                 380

Gln Pro Glu Asn Asn Tyr Lys Thr Thr Pro Ser Arg Gln Glu Pro Ser
385                 390                 395                 400

Gln Gly Thr Thr Thr Phe Ala Val Thr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Thr Ile Ser Leu Ser Pro Gly
            435                 440                 445

<210> SEQ ID NO 100
<211> LENGTH: 448
<212> TYPE: PRT
<213> ORGANISM: artificial
<220> FEATURE:
<223> OTHER INFORMATION: heavy chain for #B10-SEED(AG) antibody

<400> SEQUENCE: 100

Gln Val Gln Leu Gln Glu Ser Gly Pro Gly Leu Val Lys Pro Ser Gly
1               5                   10                  15
```

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Ser Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ala Thr Asp Trp Tyr Asp Pro Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Phe Arg Pro Glu Val His Leu Leu Pro Pro
            340                 345                 350

Ser Arg Glu Glu Met Thr Lys Asn Gln Val Ser Leu Thr Cys Leu Ala
        355                 360                 365

Arg Gly Phe Tyr Pro Lys Asp Ile Ala Val Glu Trp Glu Ser Asn Gly
370                 375                 380

Gln Pro Glu Asn Asn Tyr Lys Thr Thr Pro Ser Arg Gln Glu Pro Ser
385                 390                 395                 400

Gln Gly Thr Thr Thr Phe Ala Val Thr Ser Lys Leu Thr Val Asp Lys
                405                 410                 415

Ser Arg Trp Gln Gln Gly Asn Val Phe Ser Cys Ser Val Met His Glu
            420                 425                 430

```
Ala Leu His Asn His Tyr Thr Gln Lys Thr Ile Ser Leu Ser Pro Gly
            435                 440                 445
```

<210> SEQ ID NO 101
<211> LENGTH: 448
<212> TYPE: PRT
<213> ORGANISM: artificial
<220> FEATURE:
<223> OTHER INFORMATION: heavy chain for #A02-SEED(AG) antibody

<400> SEQUENCE: 101

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ala Thr Asp Trp Phe Asp Leu Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Phe Arg Pro Glu Val His Leu Leu Pro Pro
            340                 345                 350
```

```
Ser Arg Glu Glu Met Thr Lys Asn Gln Val Ser Leu Thr Cys Leu Ala
            355                 360                 365
Arg Gly Phe Tyr Pro Lys Asp Ile Ala Val Glu Trp Glu Ser Asn Gly
370                 375                 380
Gln Pro Glu Asn Asn Tyr Lys Thr Thr Pro Ser Arg Gln Glu Pro Ser
385                 390                 395                 400
Gln Gly Thr Thr Thr Phe Ala Val Thr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Thr Ile Ser Leu Ser Pro Gly
            435                 440                 445
```

<210> SEQ ID NO 102
<211> LENGTH: 448
<212> TYPE: PRT
<213> ORGANISM: artificial
<220> FEATURE:
<223> OTHER INFORMATION: heavy chain for #G04-SEED(AG) antibody

<400> SEQUENCE: 102

```
Gln Val Gln Leu Gln Glu Ser Gly Pro Gly Leu Val Lys Pro Ser Gly
1               5                   10                  15
Thr Leu Ser Leu Thr Cys Ala Val Ser Gly Gly Ser Ile Ser Ser Asn
            20                  25                  30
Asn Trp Trp Ser Trp Val Arg Gln Pro Pro Gly Lys Gly Leu Glu Trp
        35                  40                  45
Ile Gly Glu Ile Tyr His Ser Gly Ser Thr Ser Tyr Asn Pro Ser Leu
    50                  55                  60
Lys Ser Arg Val Thr Ile Ser Val Asp Lys Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Gly Thr Asp Trp Tyr Asp Leu Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Arg Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
```

```
Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Phe Arg Pro Glu Val His Leu Leu Pro Pro
            340                 345                 350

Ser Arg Glu Glu Met Thr Lys Asn Gln Val Ser Leu Thr Cys Leu Ala
        355                 360                 365

Arg Gly Phe Tyr Pro Lys Asp Ile Ala Val Glu Trp Glu Ser Asn Gly
    370                 375                 380

Gln Pro Glu Asn Asn Tyr Lys Thr Thr Pro Ser Arg Gln Glu Pro Ser
385                 390                 395                 400

Gln Gly Thr Thr Thr Phe Ala Val Thr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Thr Ile Ser Leu Ser Pro Gly
        435                 440                 445

<210> SEQ ID NO 103
<211> LENGTH: 448
<212> TYPE: PRT
<213> ORGANISM: artificial
<220> FEATURE:
<223> OTHER INFORMATION: heavy chain for #D02-SEED(AG) antibody

<400> SEQUENCE: 103

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Thr Asp Trp Ile Asp Thr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Phe Arg Pro Glu Val His Leu Leu Pro Pro
            340                 345                 350

Ser Arg Glu Glu Met Thr Lys Asn Gln Val Ser Leu Thr Cys Leu Ala
            355                 360                 365

Arg Gly Phe Tyr Pro Lys Asp Ile Ala Val Glu Trp Glu Ser Asn Gly
            370                 375                 380

Gln Pro Glu Asn Asn Tyr Lys Thr Thr Pro Ser Arg Gln Glu Pro Ser
385                 390                 395                 400

Gln Gly Thr Thr Thr Phe Ala Val Thr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Thr Ile Ser Leu Ser Pro Gly
            435                 440                 445

<210> SEQ ID NO 104
<211> LENGTH: 448
<212> TYPE: PRT
<213> ORGANISM: artificial
<220> FEATURE:
<223> OTHER INFORMATION: heavy chain for #D01-SEED(AG) antibody

<400> SEQUENCE: 104

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ala Thr Asp Trp Phe Asp His Trp Gly Gln Gly Thr Leu Val
            100                 105                 110

```
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Phe Arg Pro Glu Val His Leu Leu Pro Pro
                340                 345                 350

Ser Arg Glu Glu Met Thr Lys Asn Gln Val Ser Leu Thr Cys Leu Ala
        355                 360                 365

Arg Gly Phe Tyr Pro Lys Asp Ile Ala Val Glu Trp Glu Ser Asn Gly
        370                 375                 380

Gln Pro Glu Asn Asn Tyr Lys Thr Thr Pro Ser Arg Gln Glu Pro Ser
385                 390                 395                 400

Gln Gly Thr Thr Thr Phe Ala Val Thr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Thr Ile Ser Leu Ser Pro Gly
                435                 440                 445

<210> SEQ ID NO 105
<211> LENGTH: 448
<212> TYPE: PRT
<213> ORGANISM: artificial
<220> FEATURE:
<223> OTHER INFORMATION: heavy chain for #C01-SEED(AG) antibody

<400> SEQUENCE: 105

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30
```

```
Asn Trp Trp Ser Trp Val Arg Gln Pro Pro Gly Lys Gly Leu Glu Trp
            35                  40                  45

Ile Gly Glu Ile Tyr His Ser Gly Ser Thr Ser Tyr Asn Pro Ser Leu
 50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Ala Thr Asp Trp Phe Asp Ala Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Phe Arg Pro Glu Val His Leu Leu Pro Pro
            340                 345                 350

Ser Arg Glu Glu Met Thr Lys Asn Gln Val Ser Leu Thr Cys Leu Ala
        355                 360                 365

Arg Gly Phe Tyr Pro Lys Asp Ile Ala Val Glu Trp Glu Ser Asn Gly
    370                 375                 380

Gln Pro Glu Asn Asn Tyr Lys Thr Thr Pro Ser Arg Gln Glu Pro Ser
385                 390                 395                 400

Gln Gly Thr Thr Thr Phe Ala Val Thr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Thr Ile Ser Leu Ser Pro Gly
        435                 440                 445
```

-continued

```
<210> SEQ ID NO 106
<211> LENGTH: 448
<212> TYPE: PRT
<213> ORGANISM: artificial
<220> FEATURE:
<223> OTHER INFORMATION: heavy chain for #A07-SEED(AG) antibody

<400> SEQUENCE: 106
```

| | | | | | | | | | | | | | | |
|---|---|---|---|---|---|---|---|---|---|---|---|---|---|---|
| Gln | Val | Gln | Leu | Gln | Glu | Ser | Gly | Pro | Gly | Leu | Val | Lys | Pro | Ser | Gly |
| 1 | | | | 5 | | | | | 10 | | | | | 15 | |
| Thr | Leu | Ser | Leu | Thr | Cys | Ala | Val | Ser | Gly | Gly | Ser | Ile | Ser | Ser | Asn |
| | | | 20 | | | | | 25 | | | | | 30 | | |
| Asn | Trp | Trp | Ser | Trp | Val | Arg | Gln | Pro | Pro | Gly | Lys | Gly | Leu | Glu | Trp |
| | | 35 | | | | | 40 | | | | | 45 | | | |
| Ile | Gly | Glu | Ile | Tyr | His | Ser | Gly | Ser | Thr | Tyr | Asn | Pro | Ser | Leu |
| | 50 | | | | | 55 | | | | | 60 | | | | |
| Lys | Ser | Arg | Val | Thr | Ile | Ser | Val | Asp | Lys | Ser | Lys | Asn | Gln | Phe | Ser |
| 65 | | | | | 70 | | | | | 75 | | | | | 80 |
| Leu | Lys | Leu | Ser | Ser | Val | Thr | Ala | Ala | Asp | Thr | Ala | Val | Tyr | Tyr | Cys |
| | | | | 85 | | | | | 90 | | | | | 95 | |
| Ala | Arg | Gly | Thr | Asp | Trp | Tyr | Asp | Pro | Trp | Gly | Gln | Gly | Thr | Leu | Val |
| | | | 100 | | | | | 105 | | | | | 110 | | |
| Thr | Val | Ser | Ser | Ala | Ser | Thr | Lys | Gly | Pro | Ser | Val | Phe | Pro | Leu | Ala |
| | | 115 | | | | | 120 | | | | | 125 | | | |
| Pro | Ser | Ser | Lys | Ser | Thr | Ser | Gly | Gly | Thr | Ala | Ala | Leu | Gly | Cys | Leu |
| | 130 | | | | | 135 | | | | | 140 | | | | |
| Val | Lys | Asp | Tyr | Phe | Pro | Glu | Pro | Val | Thr | Val | Ser | Trp | Asn | Ser | Gly |
| 145 | | | | | 150 | | | | | 155 | | | | | 160 |
| Ala | Leu | Thr | Ser | Gly | Val | His | Thr | Phe | Pro | Ala | Val | Leu | Gln | Ser | Ser |
| | | | | 165 | | | | | 170 | | | | | 175 | |
| Gly | Leu | Tyr | Ser | Leu | Ser | Ser | Val | Val | Thr | Val | Pro | Ser | Ser | Ser | Leu |
| | | | 180 | | | | | 185 | | | | | 190 | | |
| Gly | Thr | Gln | Thr | Tyr | Ile | Cys | Asn | Val | Asn | His | Lys | Pro | Ser | Asn | Thr |
| | | 195 | | | | | 200 | | | | | 205 | | | |
| Lys | Val | Asp | Lys | Arg | Val | Glu | Pro | Lys | Ser | Cys | Asp | Lys | Thr | His | Thr |
| | 210 | | | | | 215 | | | | | 220 | | | | |
| Cys | Pro | Pro | Cys | Pro | Ala | Pro | Glu | Leu | Leu | Gly | Gly | Pro | Ser | Val | Phe |
| 225 | | | | | 230 | | | | | 235 | | | | | 240 |
| Leu | Phe | Pro | Pro | Lys | Pro | Lys | Asp | Thr | Leu | Met | Ile | Ser | Arg | Thr | Pro |
| | | | | 245 | | | | | 250 | | | | | 255 | |
| Glu | Val | Thr | Cys | Val | Val | Val | Asp | Val | Ser | His | Glu | Asp | Pro | Glu | Val |
| | | | 260 | | | | | 265 | | | | | 270 | | |
| Lys | Phe | Asn | Trp | Tyr | Val | Asp | Gly | Val | Glu | Val | His | Asn | Ala | Lys | Thr |
| | | 275 | | | | | 280 | | | | | 285 | | | |
| Lys | Pro | Arg | Glu | Glu | Gln | Tyr | Asn | Ser | Thr | Tyr | Arg | Val | Val | Ser | Val |
| | 290 | | | | | 295 | | | | | 300 | | | | |
| Leu | Thr | Val | Leu | His | Gln | Asp | Trp | Leu | Asn | Gly | Lys | Glu | Tyr | Lys | Cys |
| 305 | | | | | 310 | | | | | 315 | | | | | 320 |
| Lys | Val | Ser | Asn | Lys | Ala | Leu | Pro | Ala | Pro | Ile | Glu | Lys | Thr | Ile | Ser |
| | | | | 325 | | | | | 330 | | | | | 335 | |
| Lys | Ala | Lys | Gly | Gln | Pro | Phe | Arg | Pro | Glu | Val | His | Leu | Leu | Pro | Pro |
| | | | 340 | | | | | 345 | | | | | 350 | | |
| Ser | Arg | Glu | Glu | Met | Thr | Lys | Asn | Gln | Val | Ser | Leu | Thr | Cys | Leu | Ala |
| | | 355 | | | | | 360 | | | | | 365 | | | |
| Arg | Gly | Phe | Tyr | Pro | Lys | Asp | Ile | Ala | Val | Glu | Trp | Glu | Ser | Asn | Gly |

```
               370                375                380
Gln Pro Glu Asn Asn Tyr Lys Thr Thr Pro Ser Arg Gln Glu Pro Ser
385                 390                395                400

Gln Gly Thr Thr Thr Phe Ala Val Thr Ser Lys Leu Thr Val Asp Lys
                405                410                415

Ser Arg Trp Gln Gln Gly Asn Val Phe Ser Cys Ser Val Met His Glu
            420                425                430

Ala Leu His Asn His Tyr Thr Gln Lys Thr Ile Ser Leu Ser Pro Gly
        435                440                445

<210> SEQ ID NO 107
<211> LENGTH: 1344
<212> TYPE: DNA
<213> ORGANISM: artificial
<220> FEATURE:
<223> OTHER INFORMATION: heavy chain for #B10-SEED(AG) antibody

<400> SEQUENCE: 107
caggtgcagc tgcaggagtc gggcccagga ctggtgaagc cttcgggac  cctgtccctc      60 acctgcgctg tctctggtgg ctccatcagc agtaataact ggtggagttg gtccgccag     120 cccccaggga aggggctgga gtggattggg gaaatctatc atagtgggag caccagctac    180
aacccgtccc tcaagagtcg agtcaccata tcagtagaca gtccaagaa  ccagttctcc    240 ctgaagctgt cctctgtgac cgccgcggac acggccgtgt attactgtgc gagagccacc    300
gattggtacg acccgtgggg ccagggaacc ctggtcactg tctcttcagc tagcaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagagag ttgagcccaa atcttgtgac    660
aaaactcaca catgcccacc gtgcccagca cctgaactcc tggggggacc ctcagtcttc    720
ctcttccccc caaaacccaa ggacaccctc atgatctcta gaaccctga  ggtcacatgc    780 gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa cgatatccaa agccaaaggg   1020
cagcccttcc ggccagaggt ccacctgctg ccccccatcac gggaggagat gaccaagaac   1080
caggtcagcc tgacctgcct ggcacgcggc ttctatccca aggacatcgc cgtggagtgg   1140
gagagcaatg ggcagccgga gaacaactac aagaccacgc cttcccggca ggagcccagc   1200
cagggcacca ccaccttcgc tgtgacctcg aagctcaccg tggacaagag cagatggcag   1260
caggggaacg tcttctcatg ctccgtgatg catgaggctc tgcacaacca ctacacgcag   1320
aagaccatct ccctgtcccc gggt                                           1344

<210> SEQ ID NO 108
<211> LENGTH: 1344
<212> TYPE: DNA
<213> ORGANISM: artificial
<220> FEATURE:
<223> OTHER INFORMATION: heavy chain for #A02-SEED(AG) antibody

<400> SEQUENCE: 108
```

```
caggtgcagc tgcaggagtc gggcccagga ctggtgaagc cttcggggac cctgtccctc    60
acctgcgctg tctctggtgg ctccatcagc agtaataact ggtggagttg ggtccgccag   120
cccccaggga aggggctgga gtggattggg gaaatctatc atagtgggag caccagctac   180
aacccgtccc tcaagagtcg agtcaccata tcagtagaca gtccaagaac cagttctcc    240 ctgaagctgt cctctgtgac cgccgcggac acggccgtgt attactgtgc gagagcgacc   300
gactggtttg acctctgggg ccagggaacc ctggtcaccg tctcttcagc tagcaccaag   360
ggcccatcgg tcttccccct ggcaccctcc tccaagagca cctctggggg cacagcggcc   420
ctgggctgcc tggtcaagga ctacttcccc gaaccggtga cggtgtcgtg gaactcaggc   480
gccctgacca gcggcgtgca caccttcccg gctgtcctac agtcctcagg actctactcc   540
ctcagcagcg tggtgaccgt gccctccagc agcttgggca cccagaccta catctgcaac   600
gtgaatcaca agcccagcaa caccaaggtg gacaagagag ttgagcccaa atcttgtgac   660
aaaactcaca catgcccacc gtgcccagca cctgaactcc tggggggggcc ctcagtcttc   720 ctcttccccc caaaacccaa ggacaccctc atgatctcta gaacccctga ggtcacatgc   780
gtggtggtgg acgtgagcca cgaagaccct gaggtcaagt tcaactggta cgtggacggc   840
gtggaggtgc ataatgccaa gacaaagccg cgggaggagc agtacaacag cacgtaccgt   900
gtggtcagcg tcctcaccgt cctgcaccag gactggctga atggcaagga gtacaagtgc   960
aaggtctcca acaaagccct cccagccccc atcgagaaaa cgatatccaa agccaaaggg  1020
cagcccttcc ggccagaggt ccacctgctg ccccccatcac gggaggagat gaccaagaac  1080
caggtcagcc tgacctgcct ggcacgcggc ttctatccca aggacatcgc cgtggagtgg  1140
gagagcaatg ggcagccgga gaacaactac aagaccacgc cttcccggca ggagcccagc  1200
cagggcacca ccaccttcgc tgtgacctcg aagctcaccg tggacaagag cagatggcag  1260
caggggaacg tcttctcatg ctccgtgatg catgaggctc tgcacaacca ctacacgcag  1320
aagaccatct ccctgtcccc gggt                                        1344
```

<210> SEQ ID NO 109
<211> LENGTH: 1344
<212> TYPE: DNA
<213> ORGANISM: artificial
<220> FEATURE:
<223> OTHER INFORMATION: heavy chain for #G04-SEED(AG) antibody

<400> SEQUENCE: 109

```
caggtgcagc tgcaggagtc gggcccagga ctggtgaagc cttcggggac cctgtccctc    60
acctgcgctg tctctggtgg ctccatcagc agtaataact ggtggagttg ggtccgccag   120
cccccaggga aggggctgga gtggattggg gaaatctatc atagtgggag caccagctac   180
aacccgtccc tcaagagtcg agtcaccata tcagtagaca gtccaagaac cagttctcc    240 ctgaagctgt cctctgtgac cgccgcggac acggccgtgt attactgtgc gagagggacg   300
gactggtatg acctctgggg ccagggaacc ctggtcaccg tctcttcggc tagcaccaag   360
ggcccatcgg tcttccccct ggcaccctcc tccaagagca cctctggggg cacagcggcc   420
ctgggctgcc tggtcaagga ctacttcccc gaaccggtga cggtgtcgtg gaactcaggc   480
gccctgacca gcggcgtgca caccttcccg gctgtcctac agtcctcagg actctactcc   540
ctcagcagcg tggtgaccgt gccctccagc agcttgggca cccagaccta catctgcaac   600
gtgaatcaca agcccagcaa caccaaggtg gacaagagag ttgagcccaa atcttgtgac   660
```

| | |
|---|---|
| aaaactcaca catgcccacc gtgcccagca cctgaactcc tggggggggcc ctcagtcttc | 720 |
| ctcttccccc caaaacccaa ggacaccctc atgatctcta gaacccctga ggtcacatgc | 780 |
| gtggtggtgg acgtgagcca cgaagaccct gaggtcaagt tcaactggta cgtggacggc | 840 |
| gtggaggtgc ataatgccaa gacaaagccg cgggaggagc agtacaacag cacgtaccgt | 900 |
| gtggtcagcg tcctcaccgt cctgcaccag gactggctga atggcaagga gtacaagtgc | 960 |
| aaggtctcca acaaagccct cccagccccc atcgagaaaa cgatatccaa agccaaaggg | 1020 |
| cagcccttcc ggccagaggt ccacctgctg cccccatcac gggaggagat gaccaagaac | 1080 |
| caggtcagcc tgacctgcct ggcacgcggc ttctatccca aggacatcgc cgtggagtgg | 1140 |
| gagagcaatg ggcagccgga gaacaactac aagaccacgc cttcccggca ggagcccagc | 1200 |
| cagggcacca ccaccttcgc tgtgacctcg aagctcaccg tggacaagag cagatggcag | 1260 |
| caggggaacg tcttctcatg ctccgtgatg catgaggctc tgcacaacca ctacacgcag | 1320 |
| aagaccatct ccctgtcccc gggt | 1344 |

<210> SEQ ID NO 110
<211> LENGTH: 1344
<212> TYPE: DNA
<213> ORGANISM: artificial
<220> FEATURE:
<223> OTHER INFORMATION: heavy chain for #D02-SEED(AG) antibody

<400> SEQUENCE: 110

| | |
|---|---|
| caggtgcagc tgcaggagtc gggcccagga ctggtgaagc cttcggggac cctgtccctc | 60 |
| acctgcgctg tctctggtgg ctccatcagc agtaataact ggtggagttg ggtccgccag | 120 |
| cccccaggga aggggctgga gtggattggg gaaatctatc atagtgggag caccagctac | 180 |
| aacccgtccc tcaagagtcg agtcaccata tcagtagaca gtccaagaa ccagttctcc | 240 |
| ctgaagctgt cctctgtgac cgccgcggac acggccgtgt attactgtgc gagagggact | 300 |
| gattggatcg acacctgggg ccagggaacc ctggtcactg tctcctcagc tagcaccaag | 360 |
| ggcccatcgg tcttccccct ggcaccctcc tccaagagca cctctggggg cacagcggcc | 420 |
| ctgggctgcc tggtcaagga ctacttcccc gaaccggtga cggtgtcgtg gaactcaggc | 480 |
| gccctgacca gcggcgtgca caccttcccg gctgtcctac agtcctcagg actctactcc | 540 |
| ctcagcagcg tggtgaccgt gccctccagc agcttgggca cccagaccta catctgcaac | 600 |
| gtgaatcaca agcccagcaa caccaaggtg gacaagagag ttgagcccaa atcttgtgac | 660 |
| aaaactcaca catgcccacc gtgcccagca cctgaactcc tggggggggcc ctcagtcttc | 720 |
| ctcttccccc caaaacccaa ggacaccctc atgatctcta gaacccctga ggtcacatgc | 780 |
| gtggtggtgg acgtgagcca cgaagaccct gaggtcaagt tcaactggta cgtggacggc | 840 |
| gtggaggtgc ataatgccaa gacaaagccg cgggaggagc agtacaacag cacgtaccgt | 900 |
| gtggtcagcg tcctcaccgt cctgcaccag gactggctga atggcaagga gtacaagtgc | 960 |
| aaggtctcca acaaagccct cccagccccc atcgagaaaa cgatatccaa agccaaaggg | 1020 |
| cagcccttcc ggccagaggt ccacctgctg cccccatcac gggaggagat gaccaagaac | 1080 |
| caggtcagcc tgacctgcct ggcacgcggc ttctatccca aggacatcgc cgtggagtgg | 1140 |
| gagagcaatg ggcagccgga gaacaactac aagaccacgc cttcccggca ggagcccagc | 1200 |
| cagggcacca ccaccttcgc tgtgacctcg aagctcaccg tggacaagag cagatggcag | 1260 |
| caggggaacg tcttctcatg ctccgtgatg catgaggctc tgcacaacca ctacacgcag | 1320 |
| aagaccatct ccctgtcccc gggt | 1344 |

<210> SEQ ID NO 111
<211> LENGTH: 1344
<212> TYPE: DNA
<213> ORGANISM: artificial
<220> FEATURE:
<223> OTHER INFORMATION: heavy chain for #D01-SEED(AG) antibody

<400> SEQUENCE: 111

| | |
|---|---|
| caggtgcaac tgcaggagtc gggcccagga ctggtgaagc cttcggggac cctgtccctc | 60 |
| acctgcgctg tctctggtgg ctccatcagc agtaataact ggtggagttg ggtccgccag | 120 |
| cccccaggga aggggctgga gtggattggg gaaatctatc atagtgggag caccagctac | 180 |
| aacccgtccc tcaagagtcg agtcaccata tcagtagaca agtccaagaa ccagttctcc | 240 |
| ctgaagctgt cctctgtgac cgccgcggac acggccgtgt attactgtgc gagagccacg | 300 |
| gattggtttg accactgggg ccagggaacc ctggtcaccg tctcctcagc tagcaccaag | 360 |
| ggcccatcgg tcttccccct ggcaccctcc tccaagagca cctctggggg cacagcggcc | 420 |
| ctgggctgcc tggtcaagga ctacttcccc gaaccggtga cggtgtcgtg gaactcaggc | 480 |
| gccctgacca gcggcgtgca caccttcccg gctgtcctac agtcctcagg actctactcc | 540 |
| ctcagcagcg tggtgaccgt gccctccagc agcttgggca cccagaccta catctgcaac | 600 |
| gtgaatcaca agcccagcaa caccaaggtg gacaagagag ttgagcccaa atcttgtgac | 660 |
| aaaactcaca catgcccacc gtgcccagca cctgaactcc tggggggacc ctcagtcttc | 720 |
| ctcttccccc caaaacccaa ggacaccctc atgatctcta gaacccctga ggtcacatgc | 780 |
| gtggtggtgg acgtgagcca cgaagaccct gaggtcaagt tcaactggta cgtggacggc | 840 |
| gtggaggtgc ataatgccaa gacaaagccg cgggaggagc agtacaacag cacgtaccgt | 900 |
| gtggtcagcg tcctcaccgt cctgcaccag gactggctga atggcaagga gtacaagtgc | 960 |
| aaggtctcca acaaagccct cccagccccc atcgagaaaa cgatatccaa agccaaaggg | 1020 |
| cagcccttcc ggccagaggt ccacctgctg cccccatcac gggaggagat gaccaagaac | 1080 |
| caggtcagcc tgacctgcct ggcacgcggc ttctatccca aggacatcgc cgtggagtgg | 1140 |
| gagagcaatg ggcagccgga gaacaactac aagaccacgc cttcccggca ggagcccagc | 1200 |
| cagggcacca ccaccttcgc tgtgacctcg aagctcaccg tggacaagag cagatggcag | 1260 |
| caggggaacg tcttctcatg ctccgtgatg catgaggctc tgcacaacca ctacacgcag | 1320 |
| aagaccatct ccctgtcccc gggt | 1344 |

<210> SEQ ID NO 112
<211> LENGTH: 1344
<212> TYPE: DNA
<213> ORGANISM: artificial
<220> FEATURE:
<223> OTHER INFORMATION: heavy chain for #C01-SEED(AG) antibody

<400> SEQUENCE: 112

| | |
|---|---|
| caggtgcagc tgcaggagtc gggcccagga ctggtgaagc cttcggggac cctgtccctc | 60 |
| acctgcgctg tctctggtgg ctccatcagc agtaataact ggtggagttg ggtccgccag | 120 |
| cccccaggga aggggctgga gtggattggg gaaatctatc atagtgggag caccagctac | 180 |
| aacccgtccc tcaagagtcg agtcaccata tcagtagaca agtccaagaa ccagttctcc | 240 |
| ctgaagctgt cctctgtgac cgccgcggac acggccgtgt attactgtgc gagagcgacc | 300 |
| gattggtttg acgcctgggg ccagggaacc ctggtcaccg tctcttcagc tagcaccaag | 360 |

```
ggcccatcgg tcttcccct ggcaccctcc tccaagagca cctctggggg cacagcggcc      420
ctgggctgcc tggtcaagga ctacttcccc gaaccggtga cggtgtcgtg gaactcaggc      480
gccctgacca gcggcgtgca caccttcccg gctgtcctac agtcctcagg actctactcc      540
ctcagcagcg tggtgaccgt gccctccagc agcttgggca cccagaccta catctgcaac      600
gtgaatcaca agcccagcaa caccaaggtg gacaagagag ttgagcccaa atcttgtgac      660
aaaactcaca catgcccacc gtgcccagca cctgaactcc tggggggggcc ctcagtcttc      720 ctcttccccc caaaacccaa ggacaccctc atgatctcta gaaccctga ggtcacatgc      780 gtggtggtgg acgtgagcca cgaagaccct gaggtcaagt tcaactggta cgtggacggc      840
gtggaggtgc ataatgccaa gacaaagccg cgggaggagc agtacaacag cacgtaccgt      900
gtggtcagcg tcctcaccgt cctgcaccag gactggctga atggcaagga gtacaagtgc      960
aaggtctcca acaaagccct cccagccccc atcgagaaaa cgatatccaa agccaaaggg     1020 cagccccttcc ggccagaggt ccacctgctg cccccatcac gggaggagat gaccaagaac     1080
caggtcagcc tgacctgcct ggcacgcggc ttctatccca aggacatcgc cgtggagtgg     1140
gagagcaatg ggcagccgga gaacaactac aagaccacgc cttcccggca ggagcccagc     1200
cagggcacca ccaccttcgc tgtgacctcg aagctcaccg tggacaagag cagatggcag     1260
caggggaacg tcttctcatg ctccgtgatg catgaggctc tgcacaacca ctacacgcag     1320
aagaccatct ccctgtcccc gggt                                            1344
```

<210> SEQ ID NO 113
<211> LENGTH: 1344
<212> TYPE: DNA
<213> ORGANISM: artificial
<220> FEATURE:
<223> OTHER INFORMATION: heavy chain for #A07-SEED(AG) antibody

<400> SEQUENCE: 113

```
caggtgcagc tgcaggagtc gggcccagga ctggtgaagc cttcggggac cctgtccctc       60
acctgcgctg tctctggtgg ctccatcagc agtaataact ggtggagttg gtccgccag      120 cccccaggga aggggctgga gtggattggg gaaatctatc atagtgggag caccagctac      180
aacccgtccc tcaagagtcg agtcaccata tcagtagaca gtccaagaa ccagttctcc      240 ctgaagctgt cctctgtgac cgccgcggac acggccgtgt attactgtgc gagaggtact      300
gactggtatg accctggggg ccagggaacc ctggtcaccg tctcctcagc tagcaccaag      360
ggcccatcgg tcttcccct ggcaccctcc tccaagagca cctctggggg cacagcggcc      420
ctgggctgcc tggtcaagga ctacttcccc gaaccggtga cggtgtcgtg gaactcaggc      480
gccctgacca gcggcgtgca caccttcccg gctgtcctac agtcctcagg actctactcc      540
ctcagcagcg tggtgaccgt gccctccagc agcttgggca cccagaccta catctgcaac      600
gtgaatcaca agcccagcaa caccaaggtg gacaagagag ttgagcccaa atcttgtgac      660
aaaactcaca catgcccacc gtgcccagca cctgaactcc tggggggggcc ctcagtcttc      720 ctcttccccc caaaacccaa ggacaccctc atgatctcta gaaccctga ggtcacatgc      780 gtggtggtgg acgtgagcca cgaagaccct gaggtcaagt tcaactggta cgtggacggc      840
gtggaggtgc ataatgccaa gacaaagccg cgggaggagc agtacaacag cacgtaccgt      900
gtggtcagcg tcctcaccgt cctgcaccag gactggctga atggcaagga gtacaagtgc      960
aaggtctcca acaaagccct cccagccccc atcgagaaaa cgatatccaa agccaaaggg     1020 cagccccttcc ggccagaggt ccacctgctg cccccatcac gggaggagat gaccaagaac     1080
```

```
caggtcagcc tgacctgcct ggcacgcggc ttctatccca aggacatcgc cgtggagtgg    1140
gagagcaatg ggcagccgga gaacaactac aagaccacgc cttcccggca ggagcccagc    1200
cagggcacca ccaccttcgc tgtgacctcg aagctcaccg tggacaagag cagatggcag    1260
caggggaacg tcttctcatg ctccgtgatg catgaggctc tgcacaacca ctacacgcag    1320
aagaccatct ccctgtcccc gggt                                           1344
```

MONOCLONAL ANTIBODY DIRECTED TO FGFR1

CROSS-REFERENCE TO RELATED APPLICATIONS

This application is the U.S. national stage application of International Patent Application No. PCT/EP2017/079976, filed Nov. 21, 2017, which claims the benefit of U.S. Provisional Patent Application No. 62/425,325, filed Nov. 22, 2016.

The Sequence Listing for this application is labeled "Seq-List-replace.txt" which was created on Aug. 15, 2019 and is 148 KB. The entire content of the sequence listing is incorporated herein by reference in its entirety.

FIELD OF INVENTION

The present invention relates to antibodies with specificity for FGFR1. More particularly, the invention relates to monoclonal antibodies, and more preferably fully human monoclonal antibodies, that bind to and neutralize FGFR1 with high affinity. The invention also relates to nucleic acids encoding said antibodies, vectors for expression of these nucleic acids, and host cells for producing said antibodies. Further, the invention relates to the use of said antibodies in the diagnosis and/or treatment of cancers.

BACKGROUND OF THE INVENTION

Fibroblast growth factors (FGFs) (Beenken et al.) are a family of heparin-binding proteins (23 members for the time being) modulating the function of various cells. They are involved in many physiological processes, such as morphogenesis during development and angiogenesis, having effect on the proliferation, migration and differentiation of various types of cells including tumor and endothelial cells (Fernig and Gallagher 1994, Eswarakumar et al. 2005). They play an important role in a number of pathological processes.

There are four main types of Fibroblast Growth Factor Receptors (FGFRs) having common structural features: FGFR1, FGFR2, FGFR3 and FGFR4. They all have an extracellular ligand-binding domain containing 3 Ig-like domains (D1 to D3; they thus belong to the immunoglobulin superfamily) and unique trans-membrane and cytoplasmic regions. They also have a so-called "acid box" between Ig domains D1 and D2, which apparently works as a modulator of the FGF binding. Each one of the receptors can be bound by several FGFs (Ornitz et al. 1996).

FGFR1 has been involved in diseases such as cancers and arthritis. FGFR1 gene amplification has been associated with various cancers, such as non-small cells lung cancer, breast cancer, gastric cancer, and oesophageal cancer, glioblastoma, head and neck tumors, or osteosarcoma (Katoh and Nakagama 2014, Touat et al. 2015). FGFR1 has several alternative splicing forms, the most common ones are: 1) two differing in the domain D3: they are named FGFR1-IIIb and FGFR1-IIIc (Johnson and Williams 1993) and 2) two differing in the presence or absence of the D1 domain: they are named FGFR1a and FGFR1b. The former substitutions constitute what is believed to be part of the binding domain of the receptor, and therefore are most likely to cause the two splicing forms to have distinct ligand specificities and thus to have different effects on the FGF/FGFR pathway. The two forms have also been shown to be differentially expressed, which may be part of an exquisite control mechanism of complex functions mediated by FGFR1.

From these findings, FGFR1 has been an attractive target for cancer therapy or other conditions such as obesity or diabetes (Jiao et al. 2011, Wu et al. 2011). In the past few years, several documents describing specific antibodies targeting FGFRs and their therapeutical uses have been published. Among them, WO2005037235 discloses antibodies which are specific for FGFR1-IIIb, FGFR1-IIIc, and/or FGFR4. These antibodies were described as antagonizing and neutralizing FGFR1 and/or FGFR4IIIc as a treatment for obesity or diabetes, for instance. Another example is WO2012108782, which relates to monoclonal antibodies targeting specifically domains D2 and D3 of FGFR1, as well as their use for inhibiting tumor growth.

Depending on the effect that is expected, antibodies having agonist effect can be of interest. Some of them have been disclosed in WO2012158704 for instance. Alternatively, antibodies targeting two different domains of FGFR1 can be interesting, such as the one disclosed in WO2011000384. Blocking the FGF/FGFR1 pathway using antagonist neutralizing the receptor by binding only with specific domains of the receptor (such as D2 and D3-IIIb and -IIIc) should result in the inhibition or slow-down of tumor growth. However, although different antibodies to FGFR1 and the like have already been reported, no effective anti-cancer drug targeting FGFR1 has reached the market yet. Considering the major impact of cancers on public health, there remains a need for further FGFR1 antagonists, such as antibodies, useful as drugs. The present invention provides such antagonists of the FGF/FGFR1 pathway which will be able to treat diseases related to excessive proliferation and neovascularization. In particular, there is a need for novel molecules that could be useful as medicaments notably for treating cancers such as Non-Small Cell Lung Cancer (NSCLC) and Small Cell Lung Cancer (SCLC), head and neck squamous cell carcinomas (HNSCC), malignant pleural mesothelioma, osteosarcoma, soft tissue sarcoma, glioblastoma, metastatic renal cell carcinoma (mRCC), breast cancer or hepatic cancer.

SUMMARY OF THE INVENTION

The present invention provides new monoclonal antibodies that specifically bind to FGFR1, in particular fully human antibodies or active fragment thereof. These FGFR1 antibodies are not only able to bind but also to neutralize (or antagonize) FGFR1. They are thus able notably to bind to FGFR1+ cells, such as NCI-H520 (ATCC No. HTB-182), NCI-H1581 (ATCC No. CRL-5878), DMS114 (ATCC No. CRL-2066) or DMS53 (ATCC No. CRL-2062).

In the first embodiment, the invention describes antibodies, or portions thereof, binding to FGFR1 via their complementarity determining regions (CDRs) sequences. Antibodies comprising said CDRs retain FGFR1-binding specificity of the parent molecule from which the CDRs were obtained.

In a further embodiment, the framework regions (FRs) of said antibodies are described. Said FRs are to be combined with the CDRs according to the present invention.

In another embodiment, also disclosed are the amino acid sequences of the variable heavy and light chain of the antibodies of interest, as well as the preferred constant regions to which they can be combined.

Yet another embodiment of the present invention consists of the polynucleotide sequences encoding the antibody of the present invention, vectors and cell lines comprising said polynucleotide sequences.

Also described is a method for producing the antibodies according to the present invention.

Another embodiment of the present invention is a pharmaceutical composition comprising one or at least one of the antibodies of interest.

In a further embodiment, the monoclonal antibodies according to the present invention are for use as a FGFR1 antagonist or simply as a FGFR1 binder such as for use as antibody drug conjugates. In particular, they can be used for the treatment of disorders associated with FGFR1, or FGFR1 pathway, especially disorders associated with FGFR1 overexpression. As such the monoclonal antibodies according to the present invention can be used for the treatment of autoimmune or inflammatory diseases. In particular, such disorders or diseases are selected from multiple sclerosis, rheumatoid arthritis or Sjogren's syndrome. They can also be used for the treatment of cancers with known FGFR1 amplification, such as NSCLC, SCLC, HNSCC, malignant pleural mesothelioma, osteosarcoma, soft tissue sarcoma, glioblastoma, mRCC, breast cancer or hepatic cancer.

In a last embodiment, the invention describes antibodies, or portions thereof, binding to an epitope present on the extracellular domain of FGFR1. In particular, they bind to a fragment of FGFR1 including amino acid residues from domain D2-only (such as the ones forming the epitope of mAb #A08) or from domain D3 (such as the ones forming the epitope of mAb #A05).

Definitions

The term "immunoglobulin" (Ig) refers to a protein consisting of one or more polypeptides substantially encoded by immunoglobulin genes. One form of immunoglobulin constitutes the basic structural unit of an antibody. This form is a tetramer and consists of two identical pairs of immunoglobulin chains, each pair having one light and one heavy chain. A light chain has two parts: the variable domain (VL) and the constant domain (CL), which in the context of a light chain can be called constant region as well. A heavy chain has two parts as well: the variable domain (VH) and the constant region (CH). In each pair, the light and heavy chain variable domains are together responsible for binding to an antigen, and the constant regions are responsible for the antibody effector functions. Full-length immunoglobulin "light chains" (usually about 25 kDa) are encoded by a variable domain gene at the N-terminus (usually about 110 amino acids) and a kappa or lambda constant domain ($C_K$ and $C_\lambda$, respectively) gene at the C-terminus. Full-length immunoglobulin "heavy chains" (usually about 50 kDa), are similarly encoded by a variable domain gene (usually about 116 amino acids) and one of the other constant region genes (usually about 330 amino acids) mentioned hereinafter. There are five types of mammalian heavy chain denoted by the Greek letters: [alpha], [delta], [epsilon], [gamma], and [mu]. The type of heavy chain defines the antibody's isotype as IgA, IgD, IgE, IgG and IgM, respectively. The constant region is identical in all antibodies of the same isotype, but differs in antibodies of different isotypes. Heavy chains [gamma], [alpha] and [delta] have a constant region composed of three Ig constant domains (CH1, CH2, and CH3), and a hinge region for added flexibility; heavy chains [mu] and [epsilon] have a constant region composed of four Ig constant domains (CH1, CH2, CH3, and CH4) and a hinge region.

An immunoglobulin light or heavy chain variable domain consists of a "framework" region interrupted by three hypervariable regions. Thus, the term "hypervariable region" refers to the amino acid residues of an antibody which are responsible for antigen binding. The hypervariable region comprises amino acid residues from a "complementarity determining region" or "CDR", i.e. L-CDR1, L-CDR2 and L-CDR3 in the light chain variable domain and H-CDR1, H-CDR2 and H-CDR3 in the heavy chain variable domain (Kabat et al. 1991) and/or those residues from a "hypervariable loop" (Chothia and Lesk 1987). "Framework region" or "FR" residues are those variable domain residues other than the hypervariable region residues as herein defined. The sequences of the framework regions of different light (i.e. L-FR1, L-FR2, L-FR3 and L-FR4) or heavy (i.e. H-FR1, H-FR2, H-FR3 and H-FR4) chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDRs. The CDRs are primarily responsible for binding to an epitope of an antigen.

The term "antibody", and its plural form "antibodies", as used herein includes, inter alia, polyclonal antibodies, affinity-purified polyclonal antibodies, monoclonal antibodies, and antigen-binding fragments, such as F(ab')2, Fab proteolytic fragments, and single chain variable region fragments (scFvs). It refers both to one-armed (monovalent) or two-armed (bivalent) antibody. This term also includes SEEDbodies (Davis et al. 2010 or U.S. Pat. No. 8,871,912). Genetically engineered intact antibodies or fragments, such as chimeric antibodies, scFv and Fab fragments, as well as synthetic antigen-binding peptides and polypeptides, are also included.

The term "humanized" immunoglobulin refers to an immunoglobulin comprising a human framework region and one or more CDRs from a non-human (usually a mouse or rat) immunoglobulin. The non-human immunoglobulin providing the CDRs is called the "donor" and the human immunoglobulin providing the framework is called the "acceptor" (humanization by grafting non-human CDRs onto human framework and constant regions, or by incorporating the entire non-human variable domains onto human constant regions (chimerisation)). Constant regions need not be present, but if they are, they must be substantially identical to human immunoglobulin constant regions, i.e., at least about 85-90%, preferably about 95% or more identical. Hence, all parts of a humanized immunoglobulin, except possibly the CDRs and a few residues in the heavy chain constant region if modulation of the effector functions is needed, are substantially identical to corresponding parts of natural human immunoglobulin sequences. A "humanized antibody" is an antibody comprising a humanized light chain variable domain and a humanized heavy chain variable domain. In some instances, humanized antibodies may retain non-human residues within the human framework regions to enhance proper binding characteristics and/or some amino acid mutations may be introduced within the CDRs in order to improve the binding affinity and/or to reduce the immunogenicity and/or to increase the degree of humanness and/or to improve the biochemical/biophysical properties of the antibody.

Through humanizing antibodies, biological half-life may be increased, and the potential for adverse immune reactions upon administration to humans is reduced.

The term "fully human" immunoglobulin refers to an immunoglobulin comprising both a human framework region and human CDRs. Constant regions need not be present, but if they are, they must be substantially identical to human immunoglobulin constant regions, i.e., at least about 85-90%, preferably about 95% or more identical. Hence, all parts of a fully human immunoglobulin, except possibly few residues in the heavy chain constant region if modulation of the effector functions or pharmacokinetic properties are needed, are substantially identical to corresponding parts of natural human immunoglobulin sequences. A "fully human antibody", or "fully human monoclonal antibody", is an antibody comprising a fully human light chain variable domain and a fully human heavy chain variable domain. In some instances, amino acid mutations may be introduced within the CDRs, the framework regions or the constant region, in order to improve the binding affinity and/or to reduce the immunogenicity and/or to improve the biochemical/biophysical properties of the antibody.

The term "recombinant antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable domain or constant region. Changes in the constant region will, in general, be made in order to improve, reduce or alter characteristics, such as complement fixation (e.g. complement dependent cytotoxicity, CDC), interaction with Fc receptors, and other effector functions (e.g. antibody dependent cellular cytotoxicity, ADCC), pharmacokinetic properties (e.g. binding to the neonatal Fc receptor; FcRn). Changes in the variable domain will be made in order to improve the antigen binding characteristics. In addition to antibodies, immunoglobulins may exist in a variety of other forms including, for example, single-chain or Fv, Fab, and (Fab')2, as well as diabodies, linear antibodies, multivalent or multispecific hybrid antibodies.

As used herein, the term "antibody portion" refers to a fragment of an intact or a full-length chain or antibody, usually the binding or variable region. Said portions, or fragments, should maintain at least one activity of the intact chain/antibody, i.e. they are "functional portions" or "functional fragments". Should they maintain at least one activity, they preferably maintain the target binding property. Examples of antibody portions (or antibody fragments) include, but are not limited to, "single-chain Fv," "single-chain antibodies," "Fv" or "scFv". These terms refer to antibody fragments that comprise the variable domains from both the heavy and light chains, but lack the constant regions, all within a single polypeptide chain. Generally, a single-chain antibody further comprises a polypeptide linker between the VH and VL domains which enables it to form the desired structure that would allow for antigen binding. In specific embodiments, single-chain antibodies can also be bi-specific and/or humanized.

A "Fab fragment" is comprised of one light chain and the variable and CH1 domains of one heavy chain. The heavy chain of a Fab molecule cannot form a disulfide bond with another heavy chain molecule. A "Fab' fragment" that contains one light chain and one heavy chain and contains more of the constant region, between the CH1 and CH2 domains, such that an interchain disulfide bond can be formed between two heavy chains is called a F(ab')2 molecule. A "F(ab')2" contains two light chains and two heavy chains containing a portion of the constant region between the CH1 and CH2 domains, such that an interchain disulfide bond is formed between two heavy chains. Having defined some important terms, it is now possible to focus the attention on particular embodiments of the instant invention.

The term SEEDbody (SEED for Strand-Exchange Engineered Domain; plural form: SEEDbodies), refers to a particular type of antibody comprising derivative of human IgG and IgA CH3 domains, creating complementary human SEED CH3 heterodimers that are composed of alternating segments of human IgG and IgA CH3 sequences (FIG. 1). They are asymmetric fusion proteins. SEEDbodies and the SEED technology are described in Davis et al. 2010 or U.S. Pat. No. 8,871,912 which are incorporated herein in their entirety.

The term "treatment" within the context of this invention refers to any beneficial effect on progression of disease, including attenuation, reduction and decrease or diminishing of the pathological development after onset of disease.

The term "pharmaceutically acceptable" is meant to encompass any carrier, which does not interfere with the effectiveness of the biological activity of the active ingredient and that is not toxic to the host to which it is administered. For example, for parenteral administration, the active protein(s) may be formulated in a unit dosage form for injection in vehicles such as, but not limited to, saline, dextrose solution, serum albumin and Ringer's solution.

The human immune system has evolved to combat myriad viral, microbial, and other threats. The humoral component—the antibody response—is a critical component of the immune system's arsenal. Antibodies can coat, block, and process the foreign invader and, importantly, recruit immune effector cells to bring a wide array of defenses to bear against the offender. There are multiple antibody classes and isotypes in the human immune system, each endowed with a palette of effector functions, presumably tailored to the nature of the invading pathogen. Recombinant therapeutic antibodies are built from human sequences and are almost always derived from the IgG class. To date, the majority of therapeutic antibodies are derived from the IgG1 isotype, seconded by IgG2 and IgG4. The IgG1 isotype has a wide utility because of its built-in ability to engage immune effector cells and complement. Effector functions mediated by antibodies and effector cells include principally cytolysis (ADCC=antibody-dependent cell-mediated cytotoxicity), phagocytosis (ADCP=antibody-dependent cell mediated phagocytosis), and complement-dependent cytotoxicity (CDC). Much of our understanding of these effector functions comes from in vitro analysis of antibody mediated killing. For example, incubation of human PBMCs (peripheral blood mononuclear cells) with target cells (typically a tumor cell line) and target-specific antibody leads to lysis of the target cells over a period of hours. Most, if not all, of this ADCC is performed by natural killer (NK) cells. It has been determined that the classic IgG effector functions are mediated through appropriately named Fcγ receptors (Nimmerjahn and Ravetch 2011). In humans, the FcγRs include three activating receptors, FcγRI, FcγRIIa, and FcγRIIIa, and these are expressed to varying levels and exclusivities on leukocytes. All signal through an ITAM intracellular domain, leading to a signaling cascade resulting in the cognate effector functions of each FcγR-expressing cell. NK cells express FcγRIIIa almost exclusively, and this receptor is definitively responsible for mediating in vitro ADCC. The classical (antibody-dependent) complement pathway, triggered by engagement of the antibody Fc with complement protein C1q, includes non-cellular and cellular mechanisms, as well as synergy between complement and FcγR pathways.

The term "Fibroblast Growth Factor Receptor 1 or FGFR1", as used herein, refers to any wildtype FGFR1 from any mammalian source, such as humans, mouse or rat source, unless otherwise specified. The term includes "full-length" FGFR1 as well as any processed form of FGFR1 (e.g. mature form) or extracellular domains (which include the epitopes for the antibodies of the invention). The term also encompasses naturally occurring variants of FGFR1, e.g., splice variants or allelic variants. Examples of amino acid sequences of FGFR1 extracellular domains are for instance disclosed as SEQ ID NO: 80 to SEQ ID NO: 85. The term "epitope" refers to the part of the antigen that is bound by an antibody. In the frame of the present invention, the antigen is FGFR1.

An epitope can be either a linear epitope (i.e. made of contiguous residues within a given amino acid sequence), or a conformational epitope (i.e. made of non-contiguous residues within a given amino acid sequence, but forming a specific 3D structure).

DETAILED DESCRIPTION OF THE INVENTION

The present invention is based on the discovery of novel monoclonal antibodies, or portions thereof, more particularly fully human monoclonal antibodies that are specific to FGFR1. In particular, they are specific to human, macaque and mouse forms of FGFR1 (i.e. they are cross-reactive). These antibodies, or portions thereof, which all antagonize FGFR1, can be useful for treating cancers, such as NSCLC (squamous, adenocarcinoma or large cell carcinoma), SCLC, HNSCC, malignant pleural mesothelioma, osteosarcoma, soft tissue sarcoma, glioblastoma, mRCC, breast cancer or hepatic cancer.

The invention provides new monoclonal antibodies, or portions thereof, that bind, and neutralize (or antagonize) FGFR1, preferably the human, macaque and mouse forms of FGFR1. In particular, the invention provides new light and heavy chain variable domains that bind, modulate and neutralize (or antagonize) FGFR1, preferably the human, macaque and mouse forms of FGFR1.

Preferably, the monoclonal antibodies, or portions thereof, according to the invention bind only to isoforms IIIb and IIIc of FGFR1b, allowing to better treat the patients. Even preferably, the monoclonal antibodies, or portions thereof, according to the invention bind to domain D2-only or to domain D3-only of the isoforms IIIb and IIIc of both FGFR1a and FGFR1b.

It has been shown (see examples section) that the monoclonal antibodies, or portions thereof, according to the invention are able to inhibit the activity of cellular FGFR1. They have a strong anti-tumor activity. They are also capable to increase progression free survival (PFS) as well as to enhance ADCC against FGFR1+ cell lines. Interestingly, the monoclonal antibodies, or fragments thereof, according to the invention do not impact the hormonal FGF23 levels, resulting in an improved safety profile.

The light and heavy chain variable domains of the antibodies, or fragments thereof, according to the invention can be fused, respectively, to a kappa or lambda constant domain of a light chain and to a constant region of a heavy chain chosen among any isotype (IgA, IgD, IgE, IgG and IgM), and expressed in a variety of host cells. Preferably, the constant region chosen is that of an IgG, and more preferably of an IgG1, IgG2 or IgG4 and even more preferably of an IgG1. Alternatively, the antibodies according to the invention are SEED antibodies (or SEEDbodies) (see FIG. 1 for instance). The antibody, or portion thereof, according to the present invention can be either glycosylated/aglycosylated and/or fucosylated/afucosylated.

According to a first embodiment, any one of the monoclonal antibodies according to the invention, or portions thereof, that binds to FGFR1, comprises a heavy chain variable domain comprising H-CDR1, H-CDR2 and H-CDR3, and a light chain variable domain comprising L-CDR1, L-CDR2 and L-CDR3, wherein, 1) H-CDR1 comprises or consists of an amino acid sequence selected from the group consisting of SEQ ID NO: 3, SEQ ID NO: 6, SEQ ID NO: 7 and SEQ ID NO: 60; H-CDR2 comprises or consists of an amino acid sequence selected from the group consisting of SEQ ID NO: 4, SEQ ID NO: 8 and SEQ ID NO: 61; and H-CDR3 comprises or consists of an amino acid sequence selected from the group consisting of SEQ ID NO: 5, SEQ ID NO: 9 to SEQ ID NO: 17, SEQ ID NO: 62 and SEQ ID NO: 90 and 2) L-CDR1 comprises or consists of an amino acid sequence selected from the group consisting of SEQ ID NO: 18, SEQ ID NO: 21 and SEQ ID NO: 63; L-CDR2 comprises or consists of an amino acid sequence selected from the group consisting of SEQ ID NO: 19 and SEQ ID NO: 64, and L-CDR3 comprises or consists of an amino acid sequence selected from the group consisting of SEQ ID NO: 20, SEQ ID NO: 22, SEQ ID NO: 23, SEQ ID NO: 65 and SEQ ID NO: 66. Even more preferably, the monoclonal antibodies according to the present invention have their set of H-CDR1, H-CDR2 and H-CDR3 comprising or consisting respectively of: 1) amino acid sequences SEQ ID NO: 3, SEQ ID NO: 4 and SEQ ID NO: 5, 2) amino acid sequences SEQ ID NO: 60, SEQ ID NO: 61 and SEQ ID NO: 62, or 3) amino acid sequences SEQ ID NO:3, SEQ ID NO:4 and SEQ ID NO:90. Similarly, the monoclonal antibodies preferably have their set of L-CDR1, L-CDR2 and L-CDR3 comprising or consisting respectively of: 1) amino acid sequences SEQ ID NO: 18, SEQ ID NO: 19 and SEQ ID NO: 20, 2) amino acid sequences SEQ ID NO: 63, SEQ ID NO: 64 and SEQ ID NO: 66.

In another embodiment, the invention provides a monoclonal antibody, or portion thereof, as described herein wherein 1) the heavy chain variable domain of the monoclonal antibodies comprises framework regions (FRs) H-FR1, H-FR2, H-FR3 and H-FR4, wherein: H-FR1 comprises or consists of an amino acid sequence selected from the group consisting of SEQ ID NO: 30 and SEQ ID NO: 67; H-FR2 comprises or consists of an amino acid sequence selected from the group consisting of SEQ ID NO: 31 and SEQ ID NO: 68; H-FR3 comprises or consists of an amino acid sequence selected from the group consisting of SEQ ID NO: 32 and SEQ ID NO: 69, and H-FR4 comprises or consists of an amino acid sequence selected from the group consisting of SEQ ID NO: 33, and SEQ ID NO: 70; and 2) the light chain variable domain comprises L-FR1, L-FR2, L-FR3 and L-FR4, wherein: L-FR1 comprises or consists of an amino acid sequence selected from the group consisting of SEQ ID NO: 34 and SEQ ID NO: 71; L-FR2 comprises or consists of an amino acid sequence selected from the group consisting of SEQ ID NO: 35 and SEQ ID NO: 72; L-FR3 comprises or consists of an amino acid sequence selected from the group consisting of SEQ ID NO: 36 and SEQ ID NO: 73; and L-FR4 comprises or consists of an amino acid sequence consisting of SEQ ID NO: 37 and SEQ ID NO: 74. Preferably, the H-FRs and L-FRs according to the present invention are associated to the H-CDRs and L-CDRs above described. Preferably, the monoclonal antibodies according to the present invention have their set of H-FR1, H-FR2, H-FR3 and H-FR4 comprising or consisting respectively of: 1) amino acid sequences SEQ ID NO: 30, SEQ ID NO: 31, SEQ ID NO: 32 and SEQ ID NO: 33, or 2) amino acid sequences SEQ ID NO: 67, SEQ ID NO: 68, SEQ ID NO: 69 and SEQ ID NO: 70. Similarly, the monoclonal antibodies preferably have their set of L-FR1, L-FR2, L-FR3 and L-FR4 comprising or consisting respectively of: 1) amino acid sequences SEQ ID NO: 34, SEQ ID NO: 35, SEQ ID NO: 36 and SEQ ID NO: 37, or 2) amino acid sequences SEQ ID NO: 71, SEQ ID NO: 72, SEQ ID NO: 73 and SEQ ID NO: 74.

In yet another embodiment, the invention provides a monoclonal antibody, or a portion thereof, preferably a fully human monoclonal antibody, or portion thereof, wherein the heavy chain variable domain comprises or consists of an amino acid sequence selected from the group consisting of SEQ ID NO: 1, SEQ ID NO: 24, SEQ ID NO: 26, SEQ ID NO: 27 and SEQ ID No: 91-98; and the light chain variable domain comprises or consists of an amino acid sequence selected from the group consisting of SEQ ID NO: 2, SEQ ID NO: 25, SEQ ID NO: 28, and SEQ ID NO: 29. In a preferred embodiment, the invention provides a monoclonal antibody wherein the heavy chain variable domain comprises or consists of an amino acid sequence selected from the group consisting of SEQ ID NO: 1 and SEQ ID NO: 24; and the light chain variable domain comprises or consists of an amino acid sequence selected from the group consisting of SEQ ID NO: 2 and SEQ ID NO: 25. Preferably, the combinations variable heavy chain and variable light chain are selected from the group consisting of 1) SEQ ID NO: 24 and SEQ ID NO: 25 (mAb #A08 lead), 2) SEQ ID NO: 27 and SEQ ID NO: 29 (mAb #A05 lead). In an alternative embodiment, the combinations variable heavy chain and variable light chain can also be selected from the group consisting of: 1) SEQ ID NO: 1 and SEQ ID NO: 2 (mAb #A08 hit), 2) SEQ ID NO: 26 and SEQ ID NO: 28 (mAb #A05 hit), 3) SEQ ID NO: 93 and SEQ ID NO: 25 (mAb #A02), or 4) SEQ ID NO: 97 and SEQ ID NO: 25 (mAb #C01). Best results were obtained with #A08 hit and #A08 lead, where #A08 lead has a mutation N92S (IMGT numbering scheme; see Lefranc, 1997) in its heavy chain compared to #A08 hit and mutations Q1S as well as A2Y in its light chain compared to #A08 hit.

Additional heavy chain variable region amino acid sequences having at least 95% or more, 96% or more, 97% or more, 98% or more, or at least 99% or more sequence identity to the heavy chain variable region sequences disclosed herein are also provided. Additional light chain variable region amino acid sequences having at least 95% or more, 96% or more, 97% or more, 98% or more, or at least 99% or more sequence identity to the light chain variable region sequences disclosed herein are also provided.

The engineered monoclonal antibodies, preferably fully human antibodies, according to the present invention, may comprise any type of heavy chain constant domains, or portion thereof, from any class of antibody, including IgM, IgG, IgD, IgA and IgE, and any subclass (isotype), including notably IgG1, IgG2, IgG3 and IgG4. When it is desired that the antibody exhibits cytotoxic activity, the heavy chain constant domain is usually a complement-fixing constant domain and the class is typically of IgG1 class. When such cytotoxic activity is not desirable, the constant domain may be of the IgG2 or IgG4 class. The engineered antibody may comprise sequences from more than one class or isotype. In the context of the present invention, IgG1, IgG2 or IgG4 classes of IgG can be used. For instance, the following amino acid sequences for the heavy chain constant regions can be used: 1) an IgG1 of allotype G1m(3) as disclosed in SEQ ID NO: 38, or 2) an IgG2 isotype having a sequence as disclosed in SEQ ID NO: 39. It is to be understood that the above mentioned constant region sequences can be used in full or only part thereof, such as CH1, CH2 and/or CH3 portion thereof. Non-limiting examples of heavy chains containing both a variable domain and a constant domain is the amino acid sequences disclosed in SEQ ID NO: 45. When the antibodies according to the invention comprise IgG constant domains, they are usually in a bivalent form (i.e. they will usually dimerize). Alternatively, the constant regions of SEEDbodies can be used such as 1) SEED(AG) as disclosed in SEQ ID NO: 40 or SEQ ID NO. 43 or 2) SEED(GA) having a sequence as disclosed in SEQ ID NO: 41 or SEQ ID NO. 42. When the antibodies according to the invention comprise SEED chains, they are usually in a monovalent form (i.e. they will usually not form a homodimer comprising two full heavy chains GA/GA or AG/AG). The preferred constant chain is at least one SEED chain. Non-limiting example of heavy chain containing both a variable domain and a constant SEED domain are the amino acid sequences disclosed in SEQ ID NO: 46, SEQ ID NO: 47, SEQ ID NO: 48, SEQ ID NO: 49, and SEQ ID Nos: 99-106.

The engineered monoclonal antibodies according to the present invention may also comprise any type of light chain immunoglobulin constant domains, i.e. kappa or lambda domains. Preferably, the following amino acid sequence for the light chain constant domains can be used: a lambda constant gene such as the one described in SEQ ID NO: 44. Non-limiting example of light chain containing both a variable domain and a constant domain are the amino acid sequences disclosed in SEQ ID NO: 50 and SEQ ID NO: 51.

When the antibody of the invention is a monovalent SEEDbody, it consists of one full light chain comprising both variable and constant domains (such as the ones disclosed as SEQ ID NO: 50 and SEQ ID NO: 51), one full heavy chain comprising both variable and constant domains (such as the ones disclosed as SEQ ID NO: 46, SEQ ID NO: 47, SEQ ID NO: 48, SEQ ID NO: 49 and SEQ ID Nos: 99-106) as well as one partial heavy chain comprising only constant domains CH2 and CH3 of a SEEDbody (such as the ones disclosed as SEQ ID NO: 41 and SEQ ID NO: 43). The partial heavy chain is asymmetric to its counterpart on the full heavy chain. Should the full heavy chain being an "AG chain", the partial heavy chain will be a "GA chain" and should the full heavy chain being a "GA chain", the partial heavy chain will be an "AG chain". Thus for instance, should the full heavy chain have an amino acid sequence according to SEQ ID NO: 46, the partial heavy chain will have an amino acid sequence according to SEQ ID NO: 41. Alternatively, should the full heavy chain have an amino acid sequence according to SEQ ID NO: 47, the partial heavy chain will have an amino acid sequence according to SEQ ID NO: 43. Non-limiting examples of SEEDbodies according to the invention are for instance (as monovalent SEEDbodies): 1) a SEEDbody comprising a light chain comprising or consisting of the amino acid sequence according to SEQ ID NO:50, a full heavy chain comprising or consisting of the amino acid sequence according to SEQ ID NO:46 and a partial heavy chain comprising or consisting of the amino acid sequence according to SEQ ID NO:41, 2) a SEEDbody comprising a light chain comprising or consisting of the amino acid sequence according to SEQ ID NO:50, a full heavy chain comprising or consisting of the amino acid sequence according to SEQ ID NO:47 and a partial heavy chain comprising or consisting of the amino acid sequence according to SEQ ID NO:43, 3) a SEEDbody comprising a light chain comprising or consisting of the amino acid sequence according to SEQ ID NO:51, a full heavy chain comprising or consisting of the amino acid sequence according to SEQ ID NO:48 and a partial heavy chain comprising or consisting of the amino acid sequence according to SEQ ID NO:41, 4) a SEEDbody comprising a light chain comprising or consisting of the amino acid sequence according to SEQ ID NO:51, a full heavy chain comprising or consisting of the amino acid sequence according to SEQ ID NO:49 and a partial heavy chain comprising or consisting of the amino acid sequence according to SEQ ID NO:43 or 5) a SEEDbody comprising a light chain comprising or consisting of the amino acid sequence according to SEQ ID NO:50, a full heavy chain comprising or consisting of the amino acid sequence according to SEQ ID NO:99-106 and a partial heavy chain comprising or consisting of the amino acid sequence according to SEQ ID NO:41 The monovalent SEEDbody form is the preferred form as it allows a good inhibitory effect of the antibodies according to the present invention on cancer cells, without loss of body weight as a side effect.

It is to be understood that bivalent anti-FGFR1 SEEDbody forms are also encompassed by the present invention. A bivalent anti-FGFR1 SEEDbody consists of 2 light chains, 1 full "AG" heavy chain and 1 full "GA" heavy chain. Thus for instance, the invention encompasses a SEEDbody comprising 1) a light chain comprising or consisting of the amino acid sequence according to SEQ ID NO:50, a full heavy chain comprising or consisting of the amino acid sequence according to SEQ ID NO:46 and a full heavy chain comprising or consisting of the amino acid sequence according to SEQ ID NO:47 or 2) a light chain comprising or consisting of the amino acid sequence according to SEQ ID NO:51, a full heavy chain comprising or consisting of the amino acid sequence according to SEQ ID NO:48 and a full heavy chain comprising or consisting of the amino acid sequence according to SEQ ID NO:49.

In another aspect of the invention, the antibodies, or portions thereof, bind to an epitope present on the extracellular domain of FGFR1. In particular, they bind to a fragment of FGFR1 including amino acid residues from domain D2-only. Preferably, the antibodies, or portions thereof, according to the present invention bind to the same epitope as the one of the #A08 antibodies. More preferably, they bind to a conformational epitope localized at or near the 2 peptides including amino acid sequence residues 52-63 and 79-95 of SEQ ID NO: 81. The conformational epitope is for instance made of the residues Ala58, Ala59, Lys60, Thr61, Lys63, Lys95, Arg97, Ile104 and Asp 106. Therefore, the present invention also covers monoclonal antibodies, or portions thereof, binding to the same epitope as mAb #A08 and that antagonize FGFR1. Preferably, said monoclonal antibodies, or portion thereof, bind to a conformational epitope localized at or near the 2 peptides including amino acid sequence residues 52-63 and 79-95 of SEQ ID NO: 81. The conformational epitope is for instance made of the residues Ala58, Ala59, Lys60, Thr61, Lys63, Lys95, Arg97, Ile104 and Asp 106.

Alternatively, the antibodies, or portions thereof, bind to an epitope present on the extracellular domain of FGFR1, including amino acid residues from domain D3-only. Preferably, the antibodies, or portions thereof, according to the present invention bind to the same epitope as the mAb #A05. A further embodiment of the present invention is an isolated nucleic acid molecule, or a polynucleotide, encoding any of the antibodies or portions thereof herein described, or a complementary strand or degenerated sequence thereof. In this regard, the terms "nucleic acid molecule", or interchangeably "polynucleotide" encompass all different types of nucleic acids, including without limitation deoxyribonucleic acids (e.g., DNA, cDNA, gDNA, synthetic DNA, etc.), ribonucleic acids (e.g., RNA) and peptide nucleic acids (PNA). In a preferred embodiment, the nucleic acid molecule is a DNA molecule, such as a double-stranded DNA molecule or a cDNA molecule. The term "isolated" means nucleic acid molecules that have been identified and separated from at least one contaminant nucleic acid molecule with which it is ordinarily associated in the natural source. An isolated nucleic acid molecule is other than in the form or setting in which it is found in nature. Isolated nucleic acid molecules therefore are distinguished from the specific nucleic acid molecule as it exists in natural cells. A degenerate sequence designates any nucleotide sequence encoding the same amino acid sequence as a reference nucleotide sequence, but comprising a distinct nucleotide sequence as a result of the genetic code degeneracy.

In another embodiment a nucleic acid molecule, also called polynucleotide, encodes the heavy chains of any one of the monoclonal antibodies of the invention (including a nucleic acid molecule encoding each one of the partial and complete heavy chains in the case of monovalent SEEDbodies), or portions thereof, such as the heavy chain variable domain, and another polynucleotide encodes the light chain of any one of the antibodies of the invention, or portions thereof, such as the light chain variable domain. In an alternative embodiment a unique polynucleotide encodes the heavy (including the partial and complete heavy chains in the case of monovalent SEEDbodies) and light chains of any one of the antibodies of the invention, or portions thereof, such as the variable domains or Fab regions.

In a preferred embodiment, the polynucleotide encoding the heavy chain variable domain of an antibody of the invention comprises or consists of SEQ ID NO: 52, SEQ ID NO: 54, SEQ ID NO: 56 or SEQ ID NO: 57. In a preferred embodiment the polynucleotide encoding the light chain variable domain of an antibody of the invention comprises or consists of SEQ ID NO: 53, SEQ ID NO: 55, SEQ ID NO: 58 or SEQ ID NO: 59. In an alternative embodiment a unique polynucleotide encodes both the heavy and light chain variable domains of any one of the antibodies of the invention, wherein the polynucleotide encoding the heavy chain variable domain comprises or consists of SEQ ID NO: 52, SEQ ID NO: 54, SEQ ID NO: 56 or SEQ ID NO: 57 and the polynucleotide encoding the light chain variable domain comprises or consists of SEQ ID NO: 53, SEQ ID NO: 55, SEQ ID NO: 58 or SEQ ID NO: 59. The polynucleotide sequences encoding the heavy and light chains are usually preceded by a leader sequence.

Due to the degeneracy of the genetic code, it is to be understood that the polynucleotides encoding the antibodies according to the present invention can be optimized. Therefore, polynucleotide sequences having at least 90% or more, at least 95% or more, or at least 99% or more sequence identity to the polynucleotide sequences encoding the heavy chain variable region sequences disclosed herein, such as the preferred polynucleotide sequences listed above, are also provided. Similarly, polynucleotide sequences having at least 90% or more, at least 95% or more, or at least 99% or more sequence identity to the polynucleotide sequences encoding the light chain variable region sequences disclosed herein, such as the preferred polynucleotide sequences listed above, are also provided.

A further embodiment of this invention is a vector comprising DNA encoding any of the antibodies described herein or portions thereof, such as the variable domains (heavy and/or light variable domains) or Fab regions. The vector may be any cloning or expression vector, integrative or autonomously replicating, functional in any prokaryotic or eukaryotic cell. In particular, the vector may be a plasmid, cosmid, virus, phage, episome, artificial chromosome, and the like. The vector may comprise the entire or part of the coding sequences for both the heavy and light chain, or either of the light and heavy chain coding sequences, or any portions thereof. Should the vector comprise coding sequences for both heavy and light chains or portions thereof, these coding sequences may each be operably linked to a promoter. The promoter may be the same or different for the heavy and light chain coding sequences, or portions thereof. The heavy and light chain coding sequences, or portions thereof, may also be operably linked to one single promoter, in this case the coding sequences for the heavy and light chains, or portions thereof, may preferably be separated by an internal ribosomal entry site (IRES). Suitable promoters for eukaryotic gene expression are, for example, promoters derived from viral genes such as the murine or human cytomegalovirus (CMV), the mouse bi-directional CMV promoter, the rous sarcoma virus (RSV) promoter or the human elongation factor-1 alpha (EF-1α) promoter, which are well known to the person skilled in the art. The vector may comprise regulatory elements, such as a promoter, terminator, enhancer, selection marker, origin of replication, insulator etc. The appropriate nucleic acid sequence may be inserted into the vector by a variety of procedures. In general, DNA is inserted into an appropriate restriction endonuclease site(s) using techniques known in the art.

Construction of suitable vectors containing one or more of these components employs standard ligation techniques which are known to the skilled artisan.

A further embodiment of the present invention is a recombinant host cell, wherein said cell comprises one or more nucleic acid molecule(s)/polynucleotide(s) or one or more vector(s) as defined above. The host cell may be a prokaryotic or eukaryotic cell. Examples of prokaryotic cells include bacteria, such as E. coli. Examples of eukaryotic cells are yeast cells, plant cells, mammalian cells and insect cells including any primary cell culture or established cell line (e.g., 3T3, Vero, HEK293, TN5, etc.). Suitable host cells for the expression of glycosylated proteins are derived from multicellular organisms. Examples of preferred useful mammalian host cell lines include CHO (e.g. CHO-S, ExpiCHO, CHO-k1 or CHO-LF), HEK293 (e.g. 293, 293-6E or Expi293), NSO, SP2/0 and COS cells. The antibodies of the present invention may be produced by any technique known in the art, such as by recombinant technologies, chemical synthesis, cloning, ligations, or combinations thereof. Should it be necessary to obtain an antibody having a lower glycosylation level, an aglycosylated antibody or aglycosylated part thereof, such as an aglycosylated Fc portion, a yeast expression system or engineered/glycoengineered, CHO cell lines can be advantageously used. Similarly, should it be necessary to obtain an antibody having a lower fucosylation level, an afucosylated antibody or afucosylated part thereof, such as an afucosylated Fc portion, an engineered/glycoengineered yeast expression system or engineered/glycoengineered CHO cell lines can be advantageously used.

Another embodiment of this invention is therefore a method of producing an antibody of the present invention, or portions thereof, such as the variable domains (heavy and/or light variable domains) or Fab regions, the method comprising culturing a recombinant host cell of the invention under conditions allowing expression of the nucleic acid molecule(s) encoding any of the antibodies described herein or portions thereof, and recovering/isolating the polypeptide(s) produced. The polypeptide(s) produced may be glycosylated or not, may be fucosylated or not or may contain other post-translational modifications depending on the host cell type used. The method of producing an antibody of the present invention, or portions thereof, may further comprise the steps of purifying the antibodies, or portions thereof, and/or formulating said antibodies, or portions thereof, into a pharmaceutical composition.

Other methods for preparing the polynucleotides (including DNA and RNA) encoding the antibodies described herein, including portions thereof, such as the variable domains (heavy and/or light variable domains) or Fab regions are well known in the art. Total RNA can be prepared using guanidinium isothiocyanate extraction followed by isolation by centrifugation in a CsCl gradient (Chirgwin et al. 1979). Poly(A)+ RNA is prepared from total RNA using the method of Aviv and Leder (Aviv and Leder 1972). Complementary DNA (cDNA) is prepared from poly(A)+ RNA using known methods. Alternatively, genomic DNA can be isolated. Polynucleotides encoding FGFR1 antibodies, or portions thereof, are then identified and isolated by, for example, hybridization or PCR.

The antibodies disclosed herein, including portions thereof, such as the variable domains (heavy and/or light variable domains) or Fab regions, may be produced by any technique known in the art, such as recombinant technologies, chemical synthesis, cloning, ligations, or combinations thereof.

Many books and reviews provide teachings on how to clone and produce recombinant proteins using vectors and prokaryotic or eukaryotic host cells.

A further embodiment of the present invention is a pharmaceutical composition comprising the monoclonal antibodies according to the invention, or portions thereof, such as the variable domains (heavy and/or light variable domains) or Fab regions. Preferably, said pharmaceutical composition may further comprise at least one additional excipient, such as buffer, stabilizer, surfactant, carriers, diluents, vehicles, etc.

Pharmaceutical compositions according to the invention are useful in the prevention, and/or treatment (local or systemic) of various types of cancers such as NSCLC (squamous, adenocarcinoma or large cell carcinoma), SCLC, HNSCC, malignant pleural mesothelioma, osteosarcoma, soft tissue sarcoma, glioblastoma, mRCC, breast cancer or hepatic cancer. The pharmaceutical compositions of the invention may be administered with at least one pharmaceutically acceptable carrier.

In another aspect, the invention provides for the use of monoclonal antibody according to the invention for the preparation of a medicament for the prevention or the treatment of cancer.

Preferably, said cancer is NSCLC (squamous, adenocarcinoma or large cell carcinoma), SCLC, HNSCC, malignant pleural mesothelioma, osteosarcoma, soft tissue sarcoma, glioblastoma, mRCC, breast cancer or hepatic cancer.

In a further aspect, the invention relates to method of preventing or treating cancers, comprising administering to the patient a pharmaceutical composition or any one of the antibodies, or portions thereof, according to the invention. Preferably the cancer is squamous NSCLC (squamous, adenocarcinoma or large cell carcinoma, SCLC, HNSCC, malignant pleural mesothelioma, osteosarcoma, soft tissue sarcoma, glioblastoma, mRCC, breast cancer or hepatic cancer.

The pharmaceutical composition according to the invention can be administered in any suitable way, such as intravenously, intramuscularly, subcutaneously or intradermally.

For parenteral (e.g. intravenous, subcutaneous, intramuscular, intradermal) administration, a pharmaceutical composition of the invention can be formulated as a solution, suspension, emulsion or lyophilized powder in association with a pharmaceutically acceptable parenteral vehicle (e.g. water, saline, dextrose solution) and additives that maintain isotonicity or chemical stability (e.g. preservatives and buffers). The formulation is sterilized by commonly used techniques.

The present invention also includes recombinant antibodies, or portions thereof, such as the variable domains (heavy and/or light variable domains) or Fab regions, against FGFR1 that are functionally equivalent to those described above. Modified antibodies, or portions thereof, providing improved stability and/or therapeutic efficacy are also included. Examples of modified antibodies, or portions thereof, include those with conservative substitutions of amino acid residues, and one or more deletions or additions of amino acids which do not significantly deleteriously alter the antigen binding utility. Substitutions can range from changing or modifying one or more amino acid residues to complete redesign of a region, as long as the therapeutic utility is maintained.

Antibodies of the present invention, or portions thereof, can be modified post-translationally (e.g., acetylation, oxidation, deamidation, racemization and phosphorylation) or can be modified synthetically (e.g., the attachment of a labelling group). It is understood that the antibodies, or portions thereof, designed by the present method may have additional conservative amino acid substitutions which have substantially no effect on antigen binding or other immunoglobulin functions.

The monoclonal antibodies of the present invention, or portions thereof, such as the variable domains (heavy and/or light variable domains) or Fab regions, can include derivatives. For example, but not by way of limitation, the derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc.

Additionally, the derivative may contain one or more non-classical and/or non-natural amino acids.

The in vivo half-lives of the monoclonal antibodies of the present invention can be increased by modifying (e.g. substituting, deleting or adding) amino acid residues identified as involved in the interaction between the Fc region and the FcRn receptor.

All references cited herein, including journal articles or abstracts, patent applications or any other references, are entirely incorporated by reference herein, including all data, tables, figures and text presented in the cited references. Additionally, the entire contents of the references cited within the references cited herein are also entirely incorporated by reference.

DESCRIPTION OF THE TABLES

Figure 1A:
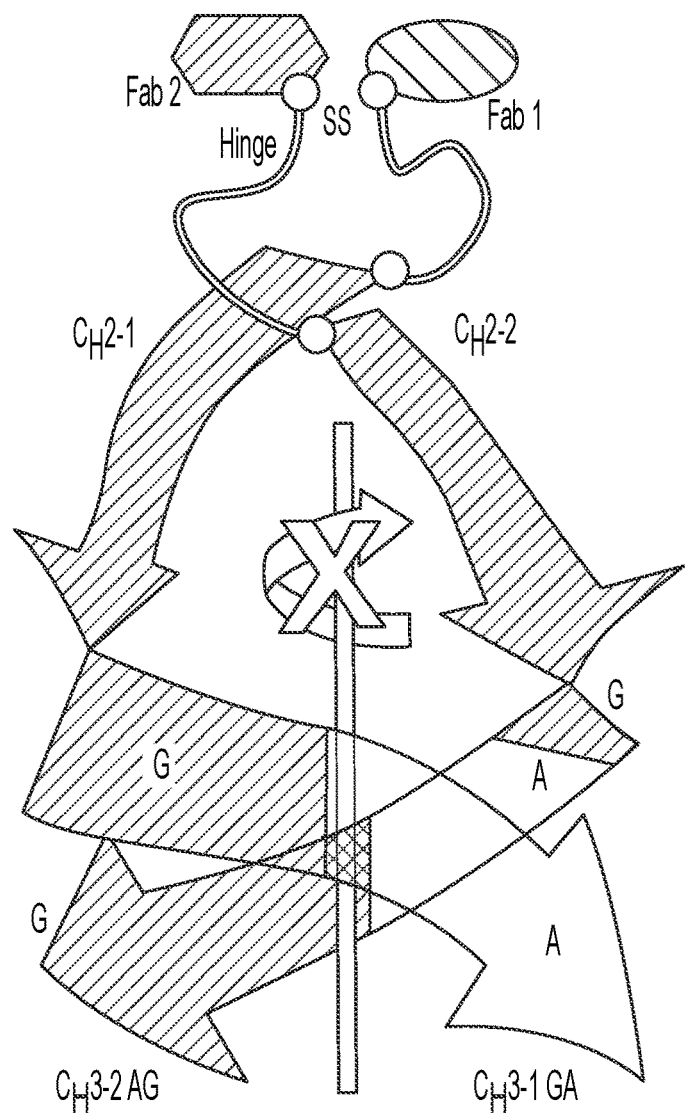
FIG. 1: A) Representation of a bivalent SEEDbody molecule having two different Fab domains, paired by the heterodimeric analogue of CH3 domain. The hashed, grey portion represents the IgG-derived portion, while the white represents the IgA-derived portion. B) Representation of a monovalent SEEDbody molecule, paired by the heterodimeric analogue of CH3 domain.
Figure 1B:
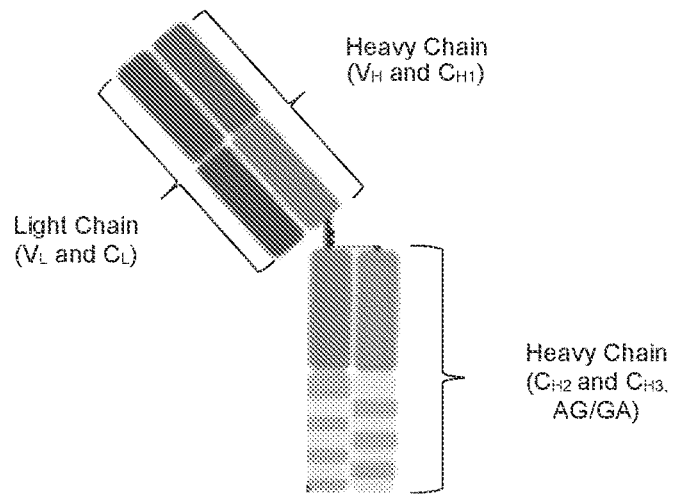

Table 1 reports the affinity constants, $K_D$ (molar, M) calculated by SPR for mAb #A05 (bivalent IgG) and mAb #A08 (bivalent IgG) against different isoforms of human FGFR1 (huFGFR1b-IIIb, huFGFR1b-IIIc, and huFGFR1a-IIIc) and against FGFR1a-IIIc from different species: mouse (mu), rat (rat), rhesus monkey (rhe) and cynomolgus monkey (cy).

Table 2 reports the inhibition of pFGFR1 by the anti-FGFR1 mAb #A05 and mAb #A08 compared to the ligand trap (FP-1039) and 2 other anti-FGFR1 (IMC-H7 and IMC-A1) antibodies in the NCI-H520 cells under non-stimulation or stimulation with FGF1 or FGF2. The selectivity of the molecules and their calculated $IC_{50}$ (molar, M) have been reported. The asterisk highlights a partial response; the hashtag notes estimated $IC_{50}$ (that could not accurately be calculated due to a poor fit).

Table 3 reports the pFGFR1 inhibition activities reported as the calculated $IC_{50}$ (molar, M) for the bivalent (IgG1) and monovalent (SEEDbody) formats for mAb #A05, mAb #A08 as compared to one other anti-FGFR1 (IMC-H7) in the NCI-H520 cells. The asterisk highlights a partial response.

Table 4 reports the affinity constants, $K_D$ (nanomolar, nM), for all FGFR1 mutants. The free energy changes are highlighted according to destabilization of antibody-antigen binding: "**": >2 kcal/mol destabilization (binding hotspots); "*":>1 kcal/mol. NBD indicates "no binding detected", NDC indicates "no data collected", ND indicates "not determined" and NC indicates "not calculated".

Table 5 reports the affinity constants, $K_D$ (nanomole, nM) for the affinity matured clones reformatted into IgG and SEEDbodies for human FGFR1b-IIIb

```
List of sequences
Variable heavy chain of antibody #A08 hit (amino acid sequence)
SEQ ID NO: 1:
EVQLQESGPGLVKPSGTLSLTCAVSGGSISSNNWWSWVRQPPGKGLEWIGEIYHSGSTSYNPSLKS

RVTISVDKSKNQFSLKLNSVTAADTAVYYCARGTDWFDPWGQGTLVTVSS

Variable light chain of antibody #A08 hit (amino acid sequence)
SEQ ID NO: 2:
QAVLTQPPSVSVAPGQTARITCGGNNIGSESVHWYQQKPGQAPVLVVYDDSDRPSGIPERFSGSNS

GNTATLTISRVEAGDEADYYCQVWDSTSDHRVFGGGTKLTVL

CDR-1 of the heavy chain of antibody #A08 hit and lead (amino acid sequence)
SEQ ID NO: 3:
GGSISSNNW CDR-2 of the heavy chain of antibody #A08 hit and lead (amino acid sequence)
SEQ ID NO: 4:
IYHSGST CDR-3 of the heavy chain of antibody #A08 hit and lead (amino acid sequence)
SEQ ID NO: 5:
ARGTDWFDP alternative CDR-1 of the heavy chain of antibody #A08 hit (amino acid
sequence)
SEQ ID NO: 6:
GGSISGNNW alternative CDR-1 of the heavy chain of antibody #A08 hit (amino acid
sequence)
SEQ ID NO: 7:
GGSINSNHW alternative CDR-2 of the heavy chain of antibody #A08 hit (amino acid
sequence)
SEQ ID NO: 8:
IYHSGSV alternative CDR-3 of the heavy chain of antibody #A08 hit (amino acid
sequence), with X being any residues selected from the group consisting of
proline (P), glutamine (Q), alanine (A), leucine (L), histidine (H),
serine (S) or threonine (T)
SEQ ID NO: 9:
ARATDWFDX alternative CDR-3 of the heavy chain of antibody #A08 hit (amino acid
sequence)
SEQ ID NO: 10:
ARGTDWYDP
```

```
alternative CDR-3 of the heavy chain of antibody #A08 hit (amino acid
sequence)
SEQ ID NO: 11:
ARGTDWIDT alternative CDR-3 of the heavy chain of antibody #A08 hit (amino acid
sequence)
SEQ ID NO: 12:
ARSTDWFDP alternative CDR-3 of the heavy chain of antibody #A08 hit (amino acid
sequence)
SEQ ID NO: 13:
ARGTDWYDA alternative CDR-3 of the heavy chain of antibody #A08 hit (amino acid
sequence)
SEQ ID NO: 14:
ARGTDWYDL alternative CDR-3 of the heavy chain of antibody #A08 hit (amino acid
sequence), with X being any residues selected from the group consisting
of S serine (S) or valine (V)
SEQ ID NO: 15:
ARXTDWFDP alternative CDR-3 of the heavy chain of antibody #A08 hit (amino acid
sequence)
SEQ ID NO: 16:
ARAKDWFDA alternative CDR-3 of the heavy chain of antibody #A08 hit (amino acid
sequence)
SEQ ID NO: 17:
ARATDWYDP CDR-1 of the light chain of antibody #A08 hit and lead (amino acid sequence)
SEQ ID NO: 18:
NIGSES CDR-2 of the light chain of antibody #A08 hit and lead (amino acid sequence)
SEQ ID NO: 19:
DDS CDR-3 of the light chain of antibody #A08 hit and lead (amino acid sequence)
SEQ ID NO: 20:
QVWDSTSDHRV alternative CDR-1 of the light chain of antibody #A08 hit (amino acid
sequence)
SEQ ID NO: 21:
NIGDET alternative CDR-3 of the light chain of antibody #A08 hit (amino acid
sequence)
SEQ ID NO: 22:
QVWDSSVDQAV alternative CDR-3 of the light chain of antibody #A08 hit (amino acid
sequence)
SEQ ID NO: 23:
QVWDSSSDHRV Variable heavy chain of antibody #A08 lead (amino acid sequence)
SEQ ID NO: 24:
EVQLQESGPGLVKPSGTLSLTCAVSGGSISSNNWWSWVRQPPGKGLEWIGEIYHSGSTSYNPSLKS

RVTISVDKSKNQFSLKLSSVTAADTAVYYCARGTDWFDPWGQGTLVTVSS

Variable light chain of antibody #A08 lead (amino acid sequence)
SEQ ID NO: 25:
SYVLTQPPSVSVAPGQTARITCGGNNIGSESVHWYQQKPGQAPVLVVYDDSDRPSGIPERFSGSNS

GNTATLTISRVEAGDEADYYCQVWDSTSDHRVFGGGTKLTVL

Variable heavy chain of antibody #A05 hit (amino acid sequence)
SEQ ID NO: 26:
QMQLVQSGAEVKKPGASVKVSCKASGHTFTGYYMHWVRQAPGQGLEWMGWINPNSGGTNYAQKF

QGRVTMTRDTSISTAYMELSRLRSDDTAVYYCARDLFWSLSSGWSIHPYYFDYWGQGTLVTVSS
```

Variable heavy chain of antibody #A05 lead (amino acid sequence)
SEQ ID NO: 27:
EVQLVQSGAEVKKPGASVKVSCKASGHTFTGYYMHWVRQAPGQGLEWMGWINPNSGGTNYAQKF

QGRVTMTRDTSISTAYMELSRLRSDDTAVYYCARDLFWSLSSGWSIHPYYFDYWGQGTLVTVSS

Variable light chain of antibody #A05 hit (amino acid sequence)
SEQ ID NO: 28:
QSALTQPASVSGSPGQSITISCTGTSSDVGSYNLVSWYQQHPGKAPKLMIYGGSKRPSGVPDRF

SGSKSDTSASLTISGLQAEDEADYYCCSYTYNGDVFGTGTKVTVL

Variable light chain of antibody #A05 lead (amino acid sequence)
SEQ ID NO: 29:
QSALTQPASVSGSPGQSITISCTGTSSDVGSYNLVSWYQQHPGKAPKLMIYGGSKRPSGVPDRF

SGSKSGNTASLTISGLQAEDEADYYCSSYTYSGDVFGTGTKVTVL

FR-1 of the heavy chain of antibody #A08 family (amino acid sequence),
with X being any residues selected from the group consisting of Q and E
(glutamic acid)
SEQ ID NO: 30:
XVQLQESGPGLVKPSGTLSLTGAVS FR-2 of the heavy chain of antibody #A08 family (amino acid sequence)
SEQ ID NO: 31:
WSWVRQPPGKGLEWIGE FR-3 of the heavy chain of antibody #A08 family (amino acid sequence),
with X being any residues selected from the group consisting of S or N
(asparagine)
SEQ ID NO: 32:
SYNPSLKSRVTISVDKSKNQFSLKLXSVTAADTAVYYC FR-4 of the heavy chain of antibody #A08 family (amino acid sequence)
SEQ ID NO: 33:
WGQGTLVTVSS FR-1 of the light chain of antibody #A08 family (amino acid sequence),
with $X_1$ being any residues selected from the group consisting of Q and
S and $X_2$ being any residues selected from the group consisting of A,
S and Y (Tyrosine)
SEQ ID NO: 34:
$X_1X_2$VLTQPPSVSVAPGQTARITCGGN FR-2 of the light chain of antibody #A08 family (amino acid sequence),
SEQ ID NO: 35:
VHWYQQKPGQAPVLVVY FR-3 of the light chain of antibody #A08 family (amino acid sequence)
SEQ ID NO: 36:
DRPSGIPERFSGSNSGNTATLTISRVEAGDEADYYC FR-4 of the light chain of antibody #A08 family (amino acid sequence)
SEQ ID NO: 37:
FGGGTKLTVL heavy chain constant region-human IgG1 allotype G1m3 (amino acid sequence)
SEQ ID NO: 38:
ASTKGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKRVEPKSCDKTHTCPPCPAPELLGGPSVFLF

PPKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSREEMTKNQVSLTCLV

KGFYPSDIAVEWESNGQPENNYKTTPPVLDSDGSFFLYSKLTVDKSRWQQGNVFSCSVMHEAL

HNHYTQKSLSLSPG heavy chain constant region-human IgG2 allotype G2h (amino acid sequence)
SEQ ID NO: 39:
ASTKGPSVFPLAPCSRSTSESTAALGCLVKDYFPEPVTVSWNSGALTSGVHTFPAVLQSSGLY

SLSSVVTVPSSNFGTQTYTCNVDHKPSNTKVDKTVEPKSSDKTHTCPPCPAPPVAGPSVFLFP

PKPKDTLMISRTPEVTCVVVDVSHEDPEVQFNWYVDGVEVHNAKTKPREEQAQSTFRVVSVLT

VVHQDWLNGKEYKCAVSNKGLPAPIEKTISKTKGQPREPQVYTLPPSREEMTKNQVSLTCLVK

GFYPSDIAVEWESNGQPENNYKTTPPMLDSDGSFFLYSKLTVDKSRWQQGNVFSCSVMHEALH

NHYTQKSLSLSPG heavy chain constant region CH1-hinge-CH2-CH3-SEED(AG) (amino acid sequence)
SEQ ID NO: 40:
ASTKGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKRVEPKSCDKTHTCPPCPAPELLGGPSVFLF

PPKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPFRPEVHLLPPSREEMTKNQVSLTCLA

RGFYPKDIAVEWESNGQPENNYKTTPSRQEPSQGTTTFAVTSKLTVDKSRWQQGNVFSCSVMH

EALHNHYTQKTISLSPG heavy chain constant region hinge-CH2-CH3-SEED(GA) (amino acid sequence)
SEQ ID NO: 41:
EPKSSDKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIEKTISKAKG

QPREPQVYTLPPPSEELALNELVTLTCLVKGFYPSDIAVEWLQGSQELPREKYLTWAPVLDSD

GSFFLYSILRVAAEDWKKGDTFSCSVMHEALHNHYTQKSLDRSPG heavy chain constant region CH1-hinge-CH2-CH3-SEED(GA) (amino acid sequence)
SEQ ID NO: 42:
ASTKGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKRVEPKSSDKTHTCPPCPAPELLGGPSVFLF

PPKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPPSEELALNELVTLTCL

VKGFYPSDIAVEWLQGSQELPREKYLTWAPVLDSDGSFFLYSILRVAAEDWKKGDTFSCSVMH

EALHNHYTQKSLDRSPG heavy chain constant region hinge-CH2-CH3-SEED(AG) (amino acid sequence)
SEQ ID NO: 43:
EPKSCDKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIEKTISKAKG

QPFRPEVHLLPPSREEMTKNQVSLTCLARGFYPKDIAVEWESNGQPENNYKTTPSRQEPSQGT

TTFAVTSKLTVDKSRWQQGNVFSCSVMHEALHNHYTQKTISLSPG light chain constant region (lambda) (amino acid sequence)
SEQ ID NO: 44:
GQPKAAPSVTLFPPSSEELQANKATLVCLISDFYPGAVTVAWKADSSPVKAGVETTTPSKQSN

NKYAASSYLSLTPEQWKSHKSYSCQVTHEGSTVEKTVAPTECS heavy chain for #A08 lead-IgG1m3 antibody (amino acid sequence)
SEQ ID NO: 45:
EVQLQESGPGLVKPSGTLSLTCAVSGGSISSNNWWSWVRQPPGKGLEWIGEIYHSGSTSYNPS

LKSRVTISVDKSKNQFSLKLSSVTAADTAVYYCARGTDWFDPWGQGTLVTVSSASTKGPSVFP

LAPSSKSTSGGTAALGCLVKDYFPEPVTVSWNSGALTSGVHTFPAVLQSSGLYSLSSVVTVPS

SSLGTQTYICNVNHKPSNTKVDKRVEPKSCDKTHTCPPCPAPELLGGPSVFLFPPKPKDTLMI

SRTPEVTCVVVDVSHEDPEVKFNWYVDGVEVHNAKTKPREEQYNSTYRVVSVLTVLHQDWLNG

KEYKCKVSNKALPAPIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMHEALHNHYTQKSLS

LSPG heavy chain for #A08 lead-SEED(AG) antibody (amino acid sequence)
SEQ ID NO: 46:
EVQLQESGPGLVKPSGTLSLTCAVSGGSISSNNWWSWVRQPPGKGLEWIGEIYHSGSTSYNPS

```
LKSRVTISVDKSKNQFSLKLSSVTAADTAVYYCARGTDWFDPWGQGTLVTVSSASTKGPSVFP

LAPSSKSTSGGTAALGCLVKDYFPEPVTVSWNSGALTSGVHTFPAVLQSSGLYSLSSVVTVPS

SSLGTQTYICNVNHKPSNTKVDKRVEPKSCDKTHTCPPCPAPELLGGPSVFLFPPKPKDTLMI

SRTPEVTCVVVDVSHEDPEVKFNWYVDGVEVHNAKTKPREEQYNSTYRVVSVLTVLHQDWLNG

KEYKCKVSNKALPAPIEKTISKAKGQPFRPEVHLLPPSREEMTKNQVSLTCLARGFYPKDIAV

EWESNGQPENNYKTTPSRQEPSQGTTTFAVTSKLTVDKSRWQQGNVFSCSVMHEALHNHYTQK

TISLSPG heavy chain for #A08 lead-SEED(GA) antibody (amino acid sequence)
SEQ ID NO: 47:
EVQLQESGPGLVKPSGTLSLTCAVSGGSISSNNWWSWVRQPPGKGLEWIGEIYHSGSTSYNPS

LKSRVTISVDKSKNQFSLKLSSVTAADTAVYYCARGTDWFDPWGQGTLVTVSSASTKGPSVFP

LAPSSKSTSGGTAALGCLVKDYFPEPVTVSWNSGALTSGVHTFPAVLQSSGLYSLSSVVTVPS

SSLGTQTYICNVNHKPSNTKVDKRVEPKSSDKTHTCPPCPAPELLGGPSVFLFPPKPKDTLMI

SRTPEVTCVVVDVSHEDPEVKFNWYVDGVEVHNAKTKPREEQYNSTYRVVSVLTVLHQDWLNG

KEYKCKVSNKALPAPIEKTISKAKGQPREPQVYTLPPPSEELALNELVTLTCLVKGFYPSDIA

VEWLQGSQELPREKYLTWAPVLDSDGSFFLYSILRVAAEDWKKGDTFSCSVMHEALHNHYTQK

SLDRSPG heavy chain for #A05 lead-SEED(AG) antibody (amino acid sequence)
SEQ ID NO: 48:
EVQLVQSGAEVKKPGASVKVSCKASGHTFTGYYMHWVRQAPGQGLEWMGWINPNSGGTNYAQK

FQGRVTMTRDTSISTAYMELSRLRSDDTAVYYCARDLFWSLSSGWSIHPYYFDYWGQGTLVTV

SSASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSCDKTHTCPPCPAPELLGGPSVF

LFPPKPKDTLMISRTPEVTCVVVDVSHEDPEVKFNWYVDGVEVHNAKTKPREEQYNSTYRVVS

VLTVLHQDWLNGKEYKCKVSNKALPAPIEKTISKAKGQPFRPEVHLLPPSREEMTKNQVSLTC

LARGFYPKDIAVEWESNGQPENNYKTTPSRQEPSQGTTTFAVTSKLTVDKSRWQQGNVFSCSV

MHEALHNHYTQKTISLSPG heavy chain for #A05 lead-SEED(GA) antibody (amino acid sequence)
SEQ ID NO: 49:
EVQLVQSGAEVKKPGASVKVSCKASGHTFTGYYMHWVRQAPGQGLEWMGWINPNSGGTNYAQK

FQGRVTMTRDTSISTAYMELSRLRSDDTAVYYCARDLFWSLSSGWSIHPYYFDYWGQGTLVTV

SSASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKRVEPKSSDKTHTCPPCPAPELLGGPSVF

LFPFKPKDTLMISRTREVTCVVVDVSHEDPEVKFNWYVDGVEVFINAKTKPREECNNSTYRVV

SVLIVLHQDWLNGKEYKCKVSNKALPAPIEKTISKAKGQPREPQVYTLPPPSEELALNELVTL

TCLVKGRYPSDIAVEWLQGSQELPREKYLTWAPVLDSDGSFFLYSILRVAAEDWKKGDTFSCS

VMHEALHNHYTQKSLDRSPG

Light chain for #A08 lead (amino acid sequence)
SEQ ID NO: 50:
SYVLTQPPSVSVAPGQTARITCGGNNIGSESVHWYQQKPGQAPVLVVYDDSDRPSGIPERFSG

SNSGNTATLTISRVEAGDEADYYCQVWDSTSDHRVFGGGTKLTVLGQPKAAPSVTLFPPSSEE

LQANKATLVCLISDFYPGAVTVAWKADSSPVKAGVETTTPSKQSNNKYAASSYLSLTPEQWKS

HKSYSCQVTHEGSTVEKTVAPTECS

Light chain for #A05 lead (amino acid sequence)
SEQ ID NO: 51:
QSALTQPASVSGSPGQSITISCTGTSSDVGSYNLVSWYQQHPGKAPKLMIYGGSKRPSGVPDR
```

FSGSKSGNTASLTISGLQAEDEADYYCSSYTYSGDVFGTGTKVTVLGQPKAAPSVTLFPPSSE

ELQANKATLVCLISDFYPGAVTVAWKADSSPVKAGVETTTPSKQSNNKYAASSYLSLTPEQWK

SHKSYSCQVTHEGSTVEKTVAPTECS

Variable heavy chain of antibody #A08 hit (nucleic acid sequence)
SEQ ID NO: 52:
GAGGTGCAGCTGCAGGAGTCGGGCCCAGGACTGGTGAAGCCTTCGGGGACCCTGTCCCTCACC

TGCGCTGTCTCTGGTGGCTCCATCAGCAGTAATAACTGGTGGAGTTGGGTCCGCCAGCCCCCAG

GGAAGGGGCTGGAGTGGATTGGGGAAATCTATCATAGTGGGAGCACCAGCTACAACCCGTCCCT

CAAGAGTCGAGTCACCATATCAGTAGACAAGTCCAAGAACCAGTTCTCCCTGAAGCTGAACTCTG

TGACCGCCGCGGACACGGCCGTGTATTACTGTGCGAGAGGCACCGACTGGTTCGACCCCTGGG

GCCAGGGAACCCTGGTCACCGTCTCCTCA

Variable light chain of antibody #A08 hit (nucleic acid sequence)
SEQ ID NO: 53:
caggctGTGCTGACTCAGCCACCCTCGGTGTCAGTGGCCCCAGGACAGACGGCCAGGATTACCTG

TGGGGGAAACAACATTGGAAGTGAAAGTGTGCACTGGTACCAACAGAAGCCAGGCCAGGCCCCT

GTGCTGGTCGTCTATGATGATAGCGACCGGCCCTCAGGGATCCCTGAGCGATTCTCTGGCTCCA

ACTCTGGGAACACGGCCACCCTGACCATCAGCAGGGTCGAAGCCGGGGATGAGGCCGACTATT

ACTGTCAGGTGTGGGATAGTACTAGTGATCATCGGGTATTCGGCGGAGGGACCAAGCTCACCGT

CCTA

Variable heavy chain of antibody #A08 lead (nucleic acid sequence)
SEQ ID NO: 54:
GAGGTGCAGCTGCAGGAGTCGGGCCCAGGACTGGTGAAGCCTTCGGGGACCCTGTCCCTCACC

TGCGCTGTCTCTGGTGGCTCCATCAGCAGTAATAACTGGTGGAGTTGGGTCCGCCAGCCCCCAG

GGAAGGGGCTGGAGTGGATTGGGGAAATCTATCATAGTGGGAGCACCAGCTACAACCCGTCCCT

CAAGAGTCGAGTCACCATATCAGTAGACAAGTCCAAGAACCAGTTCTCCCTGAAGCTGTCCTCTG

TGACCGCCGCGGACACGGCCGTGTATTACTGTGCGAGAGGCACCGACTGGTTCGACCCCTGGG

GCCAGGGAACCCTGGTCACCGTCTCCTCA

Variable light chain of antibody #A08 lead (nucleic acid sequence)
SEQ ID NO: 55:
TCCTACGTGCTGACTCAGCCACCCTCGGTGTCAGTGGCCCCAGGACAGACGGCCAGGATTACCT

GTGGGGGAAACAACATTGGAAGTGAAAGTGTGCACTGGTACCAACAGAAGCCAGGCCAGGCCC

CTGTGCTGGTCGTCTATGATGATAGCGACCGGCCCTCAGGGATCCCTGAGCGATTCTCTGGCTC

CAACTCTGGGAACACGGCCACCCTGACCATCAGCAGGGTCGAAGCCGGGGATGAGGCCGACTA

TTACTGTCAGGTGTGGGATAGTACTAGTGATCATCGGGTATTCGGCGGAGGGACCAAGCTCACC

GTCCTA

Variable heavy chain of antibody #A05 hit (nucleic acid sequence)
SEQ ID NO: 56:
CAAATGCAGCTGGTACAATCTGGGGCTGAGGTGAAGAAGCCTGGGGCCTCAGTGAAGGTCTCCT

GCAAGGCTTCTGGACACACCTTCACCGGCTACTATATGCACTGGGTGCGACAGGCCCCTGGACA

AGGGCTTGAGTGGATGGGATGGATCAACCCTAACAGTGGTGGCACAAACTATGCACAGAAGTTT

CAGGGCAGGGTCACCATGACCAGGGACACGTCCATCAGCACAGCCTACATGGAGCTGAGCAGG

CTGAGATCTGACGACACGGCCGTGTATTACTGTGCGAGAGATCTTTTCTGGTCCTTGAGCAGTGG

CTGGTCTATCCATCCGTACTACTTTGACTACTGGGGCCAGGGAACCCTGGTCACCGTCTCCTCA

Variable heavy chain of antibody #A05 lead (nucleic acid sequence)
SEQ ID NO: 57:
GAGGTGCAGCTGGTACAATCTGGGGCTGAGGTGAAGAAGCCTGGGGCCTCAGTGAAGGTCTCC -continued

TGCAAGGCTTCTGGACACACCTTCACCGGCTACTATATGCACTGGGTGCGACAGGCCCCTGGAC

AAGGGCTTGAGTGGATGGGATGGATCAACCCTAACAGTGGTGGCACAAACTATGCACAGAAGTT

TCAGGGCAGGGTCACCATGACCAGGGACACGTCCATCAGCACAGCCTACATGGAGCTGAGCAG

GCTGAGATCTGACGACACGGCCGTGTATTACTGTGCGAGAGATCTTTTCTGGTCCTTGAGCAGTG

GCTGGTCTATCCATCCGTACTACTTTGACTACTGGGGCCAGGGAACCCTGGTCACCGTCTCCTCA

Variable light chain of antibody #A05 hit (nucleic acid sequence)
SEQ ID NO: 58:
CAGTCTGCCCTGACTCAGCCTGCCTCCGTGTCTGGGTCTCCTGGACAGTCGATCACCATCTCCT

GCACTGGAACCAGCAGTGATGTTGGGAGTTATAACCTTGTCTCCTGGTACCAACAGCACCCAGG

CAAAGCCCCCAAACTCATGATTTATGGGGCAGTAAGCGGCCCTCAGGGGTCCCTGACCGATTC

TCTGGCTCCAAGTCTGACACCTCAGCCTCCCTGACCATCTCTGGGCTCCAGGCTGAGGACGAGG

CTGATTATTACTGCTGCTCATATACATACAATGGGGATGTCTTCGGAACTGGGACCAAGGTCACC

GTCCTA

Variable light chain of antibody #A05 lead (nucleic acid sequence)
SEQ ID NO: 59:
CAGTCTGCCCTGACTCAGCCTGCCTCCGTGTCTGGGTCTCCTGGACAGTCGATCACCATCTCCT

GCACTGGAACCAGCAGTGATGTTGGGAGTTATAACCTTGTCTCCTGGTACCAACAGCACCCAGG

CAAAGCCCCCAAACTCATGATTTATGGGGCAGTAAGCGGCCCTCAGGGGTCCCTGACCGATTC

TCTGGCTCCAAGTCTGGCAACACCGCCTCCCTGACCATCTCTGGGCTCCAGGCTGAGGACGAGG

CTGATTATTACTGCAGCTCATATACATACAGCGGGGATGTCTTCGGAACTGGGACCAAGGTCACC

GTCCTA

CDR-1 of the heavy chain of antibodies #A05 hit and lead (amino acid sequence)
SEQ ID NO: 60:
GHTFTGYY CDR-2 of the heavy chain of antibodies #A05 hit and lead (amino acid sequence)
SEQ ID NO: 61:
INPNSGGT CDR-3 of the heavy chain of antibodies #A05 hit and lead (amino acid sequence)
SEQ ID NO: 62:
ARDLFWSLSSGWSIHPYYFDY CDR-1 of the light chain of antibodies #A05 hit and lead (amino acid sequence)
SEQ ID NO: 63:
SSDVGSYNL CDR-2 of the light chain of antibodies #A05 hit and lead (amino acid sequence)
SEQ ID NO: 64:
GGS CDR-3 of the light chain of antibody #A05 hit (amino acid sequence)
SEQ ID NO: 65:
CSYTYNGDV CDR-3 of the light chain of antibody #A05 lead (amino acid sequence)
SEQ ID NO: 66:
SSYTYSGDV FR-1 of the heavy chain of antibody #A05 family (amino acid sequence),
with $X_1$ being any residues selected from the group consisting of Q and
E and $X_2$ being any residues selected from the group consisting of M
(Methionine) and V (Valine)
SEQ ID NO: 67:
$X_1X_2$QLVQSGAEVKKPGASVKVSCKAS FR-2 of the heavy chain of antibody #A05 family (amino acid sequence)
SEQ ID NO: 68:
MHWVRQAPGQGLEWMGW FR-3 of the heavy chain of antibody #A05 family (amino acid sequence)
SEQ ID NO: 69:
NYAQKFQGRVTMTRDTSISTAYMELSRLRSDDTAVYYC FR-4 of the heavy chain of antibody #A05 family (amino acid sequence)
SEQ ID NO: 70:
WGQGTLVTVSS FR-1 of the light chain of antibody #A05 family (amino acid sequence),
SEQ ID NO: 71:
QSALTQPASVSGSPGQSITISCTGT FR-2 of the light chain of antibody #A05 family (amino acid sequence),
SEQ ID NO: 72:
VSWYQQHPGKAPKLMIY FR-3 of the light chain of antibody #A05 family (amino acid sequence),
with $X_1$ being any residues selected from the group consisting of D (aspartic
acid) and G (glycine), $X_2$ being any residues selected from the group
consisting of T and N and $X_3$ being any residues selected from the group
consisting of S and T.
SEQ ID NO: 73:
KRPSGVPDRFSGSKSX$_1$X$_2$X$_3$ASLTISGLQAEDEADYYC FR-4 of the light chain of antibody #A05 family (amino acid sequence)
SEQ ID NO: 74:
FGTGTKVTVL light chain constant region (lambda) (nucleic acid sequence)
SEQ ID NO: 75:
GGACAGCCCAAGGCTGCCCCCTCGGTCACTCTGTTCCCGCCCTCCTCTGAGGAGCTTCAAGCCA

ACAAGGCCACACTGGTGTGTCTCATAAGTGACTTCTACCCGGGAGCCGTGACAGTGGCCTGGAA

GGCAGATAGCAGCCCCGTCAAGGCGGGAGTGGAGACCACCACACCCTCCAAACAAAGCAACAA

CAAGTACGCGGCCAGCAGCTACCTGAGCCTGACGCCTGAGCAGTGGAAGTCCCACAAAAGCTAC

AGCTGCCAGGTCACGCATGAAGGGAGCACCGTGGAGAAGACAGTGGCCCCTACAGAATGTTCA heavy chain constant region-human IgG1 allotype G1m3 (nucleic acid sequence)
SEQ ID NO: 76:
GCTAGCACCAAGGGCCCATCGGTCTTCCCCCTGGCACCCTCCTCCAAGAGCACCTCTGGGGGC

ACAGCGGCCCTGGGCTGCCTGGTCAAGGACTACTTCCCCGAACCGGTGACGGTGTCGTGGAAC

TCAGGCGCCCTGACCAGCGGCGTGCACACCTTCCCGGCTGTCCTACAGTCCTCAGGACTCTACT

CCCTCAGCAGCGTGGTGACCGTGCCCTCCAGCAGCTTGGGCACCCAGACCTACATCTGCAACGT

GAATCACAAGCCCAGCAACACCAAGGTGGACAAGAGAGTTGAGCCCAAATCTTGTGACAAAACTC

ACACATGCCCACCGTGCCCAGCACCTGAACTCCTGGGGGGACCGTCAGTCTTCCTCTTCCCCCC

AAAACCCAAGGACACCCTCATGATCTCCCGGACCCCTGAGGTCACATGCGTGGTGGTGGACGTG

AGCCACGAAGACCCTGAGGTCAAGTTCAACTGGTACGTGGACGGCGTGGAGGTGCATAATGCCA

AGACAAAGCCGCGGGAGGAGCAGTACAACAGCACGTACCGTGTGGTCAGCGTCCTCACCGTCC

TGCACCAGGACTGGCTGAATGGCAAGGAGTACAAGTGCAAGGTCTCCAACAAAGCCCTCCCAGC

CCCCATCGAGAAAACCATCTCCAAAGCCAAAGGGCAGCCCCGAGAACCACAGGTGTACACCCTG

CCCCCATCACGGGAGGAGATGACCAAGAACCAGGTCAGCCTGACCTGCCTGGTCAAAGGCTTCT

ATCCCAGCGACATCGCCGTGGAGTGGGAGAGCAATGGGCAGCCGGAGAACAACTACAAGACCA

CGCCTCCCGTGCTGGACTCCGACGGCTCCTTCTTCCTCTATAGCAAGCTCACCGTGGACAAGAG

CAGGTGGCAGCAGGGGAACGTCTTCTCATGCTCCGTGATGCATGAGGCTCTGCACAACCACTAC

ACGCAGAAGAGCCTCTCCCTGTCCCCGGGT heavy chain constant region-human IgG2 allotype G2h (nucleic acid sequence)
SEQ ID NO: 77:
GCTAGCACCAAGGGCCCATCGGTCTTCCCCCTGGCGCCCTGCTCCAGGAGCACCTCCGAGAGC

ACAGCGGCCCTGGGCTGCCTGGTCAAGGACTACTTCCCCGAACCGGTGACGGTGTCGTGGAAC

TCAGGCGCTCTGACCAGCGGCGTGCACACCTTCCCAGCTGTCCTACAGTCCTCAGGACTCTACT

CCCTCAGCAGCGTGGTGACCGTGCCCTCCAGCAACTTCGGCACCCAGACCTACACCTGCAACGT

AGATCACAAGCCCAGCAACACCAAGGTGGACAAGACAGTTGAGCCCAAATCTTCTGACAAAACTC

-continued

ACACATGCCCACCGTGCCCAGCACCACCTGTGGCAGGACCGTCAGTCTTCCTCTTCCCCCCAAA

ACCCAAGGACACCCTCATGATCTCCCGGACCCCTGAGGTCACGTGCGTGGTGGTGGACGTGAG

CCACGAAGACCCCGAGGTCCAGTTCAACTGGTACGTGGACGGCGTGGAGGTGCATAATGCCAA

GACAAAGCCACGGGAGGAGCAGGCCCAGAGCACGTTCCGTGTGGTCAGCGTCCTCACCGTTGT

GCACCAGGACTGGCTGAACGGCAAGGAGTACAAGTGCGCTGTCTCCAACAAAGGCCTCCCAGC

CCCCATCGAGAAAACCATCTCCAAAACCAAAGGGCAGCCCCGAGAACCACAGGTGTACACCCTG

CCCCCATCACGGGAGGAGATGACCAAGAACCAGGTCAGCCTGACCTGCCTGGTCAAAGGCTTCT

ACCCCAGCGACATCGCCGTGGAGTGGGAGAGCAATGGGCAGCCGGAGAACAACTACAAGACCA

CACCTCCCATGCTGGACTCCGACGGCTCCTTCTTCCTCTACAGCAAGCTCACCGTGGACAAGAG

CAGGTGGCAGCAGGGGAACGTCTTCTCATGCTCCGTGATGCATGAGGCTCTGCACAACCACTAC

ACACAGAAGAGCCTCTCCCTGTCCCCGGGT heavy chain constant region-SEED(AG) (nucleic acid sequence)
SEQ ID NO: 78:
GCTAGCACCAAGGGCCCATCGGTCTTCCCCCTGGCACCCTCCTCCAAGAGCACCTCTGGGGGC

ACAGCGGCCCTGGGCTGCCTGGTCAAGGACTACTTCCCCGAACCGGTGACGGTGTCGTGGAAC

TCAGGCGCCCTGACCAGCGGCGTGCACACCTTCCCGGCTGTCCTACAGTCCTCAGGACTCTACT

CCCTCAGCAGCGTGGTGACCGTGCCCTCCAGCAGCTTGGGCACCCAGACCTACATCTGCAACGT

GAATCACAAGCCCAGCAACACCAAGGTGGACAAGAGAGTTGAGCCCAAATCTTGTGACAAAACTC

ACACATGCCCACCGTGCCCAGCACCTGAACTCCTGGGGGGGCCCTCAGTCTTCCTCTTCCCCCC

AAAACCCAAGGACACCCTCATGATCTCTAGAACCCCTGAGGTCACATGCGTGGTGGTGGACGTG

AGCCACGAAGACCCTGAGGTCAAGTTCAACTGGTACGTGGACGGCGTGGAGGTGCATAATGCCA

AGACAAAGCCGCGGGAGGAGCAGTACAACAGCACGTACCGTGTGGTCAGCGTCCTCACCGTCC

TGCACCAGGACTGGCTGAATGGCAAGGAGTACAAGTGCAAGGTCTCCAACAAAGCCCTCCCAGC

CCCCATCGAGAAAACGATATCCAAAGCCAAAGGGCAGCCCTTCCGGCCAGAGGTCCACCTGCTG

CCCCCATCACGGGAGGAGATGACCAAGAACCAGGTCAGCCTGACCTGCCTGGCACGCGGCTTC

TATCCCAAGGACATCGCCGTGGAGTGGGAGAGCAATGGGCAGCCGGAGAACAACTACAAGACC

ACGCCTTCCCGGCAGGAGCCCAGCCAGGGCACCACCACCTTCGCTGTGACCTCGAAGCTCACC

GTGGACAAGAGCAGATGGCAGCAGGGGAACGTCTTCTCATGCTCCGTGATGCATGAGGCTCTGC

ACAACCACTACACGCAGAAGACCATCTCCCTGTCCCCGGGT heavy chain constant region-SEED(GA) (nucleic acid sequence)
SEQ ID NO: 79:
GAGCCCAAATCTTCTGACAAAACTCACACATGCCCACCGTGCCCAGCACCTGAACTCCTGGGGG

GGCCCTCAGTCTTCCTCTTCCCCCCAAAACCCAAGGACACCCTCATGATCTCTAGAACCCCTGAG

GTCACATGCGTGGTGGTGGACGTGAGCCACGAAGACCCTGAGGTCAAGTTCAACTGGTACGTGG

ACGGCGTGGAGGTGCATAATGCCAAGACAAAGCCGCGGGAGGAGCAGTACAACAGCACGTACC

GTGTGGTCAGCGTCCTCACCGTCCTGCACCAGGACTGGCTGAATGGCAAGGAGTACAAGTGCAA

GGTCTCCAACAAAGCCCTCCCAGCCCCCATCGAGAAAACGATATCCAAAGCCAAAGGGCAGCCC

CGAGAACCACAGGTGTACACCCTGCCCCCACCGTCGGAGGAGCTGGCCCTGAACGAGCTGGTG

ACGCTGACCTGCCTGGTCAAAGGCTTCTATCCCAGCGACATCGCCGTGGAGTGGCTGCAGGGGT

CCCAGGAGCTGCCCCGCGAGAAGTACCTGACTTGGGCACCCGTGCTGGACTCCGACGGCTCCT

TCTTCCTCTATAGTATACTGCGCGTGGCAGCCGAGGACTGGAAGAAGGGGGACACCTTCTCATG

CTCCGTGATGCATGAGGCTCTGCACAACCACTACACGCAGAAGAGCCTCGACCGCTCCCCGGGT

```
human FGFR1b-IIIb extracellular domain (amino acid sequence)
SEQ ID NO: 80:
RPSPTLPEQDALPSSEDDDDDDSSSEEKETDNTKPNPVAPYWTSPEKMEKKLHAVPAAKTVKFKCP

SSGTPNPTLRWLKNGKEFKPDHRIGGYKVRYATWSIIMDSVVPSDKGNYTCIVENEYGSINHTYQLDV

VERSPHRPILQAGLPANKTVALGSNVEFMCKVYSDPQPHIQWLKHIEVNGSKIGPDNLPYVQILKHSGI

NSSDAEVLTLFNVTEAQSGEYVCKVSNYIGEANQSAWLTVTRPALEERPAVMTSPLYLE human FGFR1b-IIIc extracellular domain (amino acid sequence)
SEQ ID NO: 81:
RPSPTLPEQDALPSSEDDDDDDSSSEEKETDNTKPNPVAPYWTSPEKMEKKLHAVPAAKTVKFKCP

SSGTPNPTLRWLKNGKEFKPDHRIGGYKVRYATWSIIMDSVVPSDKGNYTCIVENEYGSINHTYQLDV

VERSPHRPILQAGLPANKTVALGSNVEFMCKVYSDPQPHIQWLKHIEVNGSKIGPDNLPYVQILKTAGV

NTTDKEMEVLHLRNVSFEDAGEYTCLAGNSIGLSHHSAWLTVLEALEERPAVMTSPLYLE mouse FGFR1b-IIIb extracellular domain (amino acid sequence)
SEQ ID NO: 82:
RPAPTLPEQDALPSSEDDDDDDSSSEEKETDNTKPNPVAPYWTSPEKMEKKLHAVPAAKTVKFKCP

SSGTPNPTLRWLKNGKEFKPDHRIGGYKVRYATWSIIMDSVVPSDKGNYTCIVENEYGSINHTYQLDV

VERSPHRPILQAGLPANKTVALGSNVEFMCKVYSDPQPHIQWLKHIEVNGSKIGPDNLPYVQILKHSGI

NSSDAEVLTLFNVTEAQSGEYVCKVSNYIGEANQSAWLTVTRPVAKALEERPAVMTSPLYLE mouse FGFR1b-IIIc extracellular domain (amino acid sequence)
SEQ ID NO: 83:
RPAPTLPEQDALPSSEDDDDDDSSSEEKETDNTKPNPVAPYWTSPEKMEKKLHAVPAAKTVKFKCP

SSGTPNPTLRWLKNGKEFKPDHRIGGYKVRYATWSIIMDSVVPSDKGNYTCIVENEYGSINHTYQLDV

VERSPHRPILQAGLPANKTVALGSNVEFMCKVYSDPQPHIQWLKHIEVNGSKIGPDNLPYVQILKTAGV

NTTDKEMEVLHLRNVSFEDAGEYTCLAGNSIGLSHHSAWLTVLEALEERPAVMTSPLYLE

Human FGFR1 D2-His6 (amino acid sequence)
SEQ ID NO: 84:
RPSPTLPEQDALPSSEDDDDDDSSSEEKETDNTKPNPVAPYWTSPEKMEKKLHAVPAAKTVKFKCP

SSGTPNPTLRWLKNGKEFKPDHRIGGYKVRYATWSIIMDSVVPSDKGNYTCIVENEYGSINHTYQLDV

VERSPHRHHHHHH

Human FGFR1-IIIc D3-His6 (amino acid sequence)
SEQ ID NO: 85:
RPILQAGLPANKTVALGSNVEFMCKVYSDPQPHIQWLKHIEVNGSKIGPDNLPYVQILKTAGVNTTDKE

MEVLHLRNVSFEDAGEYTCLAGNSIGLSHHSAWLTVLEALEERPAVMTSPLYLEHHHHHH human FGFR1b-IIIb extracellular domain with a HIS tag (amino acid sequence)
SEQ ID NO: 86:
RPSPTLPEQDALPSSEDDDDDDSSSEEKETDNTKPNPVAPYWTSPEKMEKKLHAVPAAKTVKFKCP

SSGTPNPTLRWLKNGKEFKPDHRIGGYKVRYATWSIIMDSVVPSDKGNYTCIVENEYGSINHTYQLDV

VERSPHRPILQAGLPANKTVALGSNVEFMCKVYSDPQPHIQWLKHIEVNGSKIGPDNLPYVQILKHSGI

NSSDAEVLTLFNVTEAQSGEYVCKVSNYIGEANQSAWLTVTRPALEERPAVMTSPLYLEHHHHHH human FGFR1b-IIIc extracellular domain with a HIS tag (amino acid sequence)
SEQ ID NO: 87:
RPSPTLPEQDALPSSEDDDDDDSSSEEKETDNTKPNPVAPYWTSPEKMEKKLHAVPAAKTVKFKCP

SSGTPNPTLRWLKNGKEFKPDHRIGGYKVRYATWSIIMDSVVPSDKGNYTCIVENEYGSINHTYQLDV

VERSPHRPILQAGLPANKTVALGSNVEFMCKVYSDPQPHIQWLKHIEVNGSKIGPDNLPYVQILKTAGV

NTTDKEMEVLHLRNVSFEDAGEYTCLAGNSIGLSHHSAWLTVLEALEERPAVMTSPLYLEHHHHHH mouse FGFR1b-IIIb extracellular domain with His tag (amino acid sequence)
SEQ ID NO: 88:
RPAPTLPEQDALPSSEDDDDDDSSSEEKETDNTKPNPVAPYWTSPEKMEKKLHAVPAAKTVKFKCP

SSGTPNPTLRWLKNGKEFKPDHRIGGYKVRYATWSIIMDSVVPSDKGNYTCIVENEYGSINHTYQLDV

VERSPHRPILQAGLPANKTVALGSNVEFMCKVYSDPQPHIQWLKHIEVNGSKIGPDNLPYVQILKHSGI
```

NSSDAEVLTLFNVTEAQSGEYVCKVSNYIGEANQSAWLTVTRPVAKALEERPAVMTSPLYLEHHHHH

H mouse FGFR1b-IIIc extracellular domain with His tag (amino acid sequence)
SEQ ID NO: 89:
RPAPTLPEQDALPSSEDDDDDDDSSSEEKETDNTKPNPVAPYWTSPEKMEKKLHAVPAAKTVKFKCP

SSGTPNPTLRWLKNGKEFKPDHRIGGYKVRYATWSIIMDSVVPSDKGNYTCIVENEYGSINHTYQLDV

VERSPHRPILQAGLPANKTVALGSNVEFMCKVYSDPQPHIQWLKHIEVNGSKIGPDNLPYVQILKTAGV

NTTDKEMEVLHLRNVSFEDAGEYTCLAGNSIGLSHHSAWLTVLEALEERPAVMTSPLYLEHHHHHH alternative CDR-3 of the heavy chain of antibody #A08 hit (amino acid
sequence), with $X_1$ being any residues selected from the group consisting
of S (Serine), G (Glycine), A (Alanine) or V (Valine); $X_2$ being any residues
selected from the group consisting of T (Threonine) or K (Lysine); $X_3$ being
any residues selected from the group consisting of F (Phenylalanine), Y
(Tyrosine) or I (lsoleucine) and $X_4$ being any residues selected from the
group consisting of P (Proline), L (Leucine), A (Alanine), T (Threonine)
and H (Histidine)
SEQ ID NO: 90:
AR$X_1X_2$DW$X_3$D$X_4$ alternative variable heavy chain of antibody #A08 hit (amino acid sequence),
with X2 being any residues selected from the group consisting of Q (Glutamine)
or E (Glutamic Acid); $X_2$ being any residues selected from the group consisting
of S (Serine), G (Glycine), A (Alanine) or V (Valine); $X_3$ being any residues
selected from the group consisting of T (Threonine) or K (Lysine); $X_4$ being
any residues selected from the group consisting of F (Phenylalanine),
Y (Tyrosine) or I (Isoleucine) and $X_5$ being any residues selected from the
group consisting of P (Proline), L (Leucine), A (Alanine), T (Threonine)
and H (Histidine)
SEQ ID NO: 91:
$X_1$VQLQESGPGLVKPSGTLSLTCAVSGGSISSNNWWSVVVRQPPGKGLEWIGEIYHSGSTSYNPSLKS

RVTISVDKSKNQFSLKLNSVTAADTAVYYCAR$X_2X_3$DW$X_4$D$X_5$WGQGTLVTVSS variable heavy chain for #B10-SEED(AG) antibody (amino acid sequence)
SEQ ID NO: 92:
QVQLQESGPGLVKPSGTLSLTCAVSGGSISSNNWWSWVRQPPGKGLEWIGEIYHSGSTSYNPSLKS

RVTISVDKSKNQFSLKLSSVTAADTAVYYCARATDWYDPWGQGTLVTVSS variable heavy chain for #A02-SEED(AG) antibody (amino acid sequence)
SEQ ID NO: 93:
QVQLQESGPGLVKPSGTLSLTCAVSGGSISSNNWWSWVRQPPGKGLEWIGEIYHSGSTSYNPSLKS

RVTISVDKSKNQFSLKLSSVTAADTAVYYCARATDWFDLWGQGTLVTVSS variable heavy chain for #G04-SEED(AG) antibody (amino acid sequence)
SEQ ID NO: 94:
QVQLQESGPGLVKPSGTLSLTCAVSGGSISSNNWWSWVRQPPGKGLEWIGEIYHSGSTSYNPSLKS

RVTISVDKSKNQFSLKLSSVTAADTAVYYCARGTDWYDLWGQGTLVTVSS variable heavy chain for #D02-SEED(AG) antibody (amino acid sequence)
SEQ ID NO: 95:
QVQLQESGPGLVKPSGTLSLTCAVSGGSISSNNWWSWVRQPPGKGLEWIGEIYHSGSTSYNPSLKS

RVTISVDKSKNQFSLKLSSVTAADTAVYYCARGTDWIDTWGQGTLVTVSS variable heavy chain for #D01-SEED(AG) antibody (amino acid sequence)
SEQ ID NO: 96:
QVQLQESGPGLVKPSGTLSLTCAVSGGSISSNNWWSWVRQPPGKGLEWIGEIYHSGSTSYNPSLKS

RVTISVDKSKNQFSLKLSSVTAADTAVYYCARATDWFDHWGQGTLVTVSS variable heavy chain for #C01-SEED(AG) antibody (amino acid sequence)
SEQ ID NO: 97:
QVQLQESGPGLVKPSGTLSLTCAVSGGSISSNNWWSWVRQPPGKGLEWIGEIYHSGSTSYNPSLKS

RVTISVDKSKNQFSLKLSSVTAADTAVYYCARATDWFDAWGQGTLVTVSS variable heavy chain for #A07-SEED(AG) antibody (amino acid sequence)
SEQ ID NO: 98:
QVQLQESGPGLVKPSGTLSLTCAVSGGSISSNNWWSWVRQPPGKGLEWIGEIYHSGSTSYNPSLKS

RVTISVDKSKNQFSLKLSSVTAADTAVYYCARGTDWYDPWGQGTLVTVSS alternative heavy chain for #A08 lead-SEED(AG) antibody (amino acid sequence),
with $X_1$ being any residues selected from the group consisting of Q (Glutamine)
or E (Glutamic Acid); $X_2$ being any residues selected from the group consisting
of S (Serine), G (Glycine), A (Alanine) or V (Valine); $X_3$ being any residues
selected from the group consisting of T (Threonine) or K (Lysine); $X_4$ being
any residues selected from the group consisting of F (Phenylalanine), Y
(Tyrosine) or I (Isoleucine) and $X_5$ being any residues selected from the
group consisting of P (Proline), L (Leucine), A (Alanine), T (Threonine)
and H (Histidine)
SEQ ID NO: 99:
$X_1$VQLQESGPGLVKPSGTLSLTCAVSGGSISSNNWWSWVRQPPGKGLEWIGEIYHSGSTSYNPSLKS RVTISVDKSKNQFSLKLSSVTAADTAVYYCARX$_2$X$_3$DWX$_4$DX$_5$WGQGTLVTVSSASTKGPSVFPLAPSS

KSTSGGTAALGCLVKDYFPEPVTVSWNSGALTSGVHTFPAVLQSSGLYSLSSVVTVPSSSLGTQTYIC

NVNHKPSNTKVDKRVEPKSCDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKT

ISKAKGQPFRPEVHLLPPSREEMTKNQVSLTCLARGFYPKDIAVEWESNGQPENNYKTTPSRQEPSQ

GTTTFAVTSKLTVDKSRWQQGNVFSCSVMHEALHNHYTQKTISLSPG heavy chain for #B10-SEED(AG) antibody (amino acid sequence)
SEQ ID NO: 100:
QVQLQESGPGLVKPSGTLSLTCAVSGGSISSNNWWSWVRQPPGKGLEWIGEIYHSGSTSYNPSLKS

RVTISVDKSKNQFSLKLSSVTAADTAVYYCARATDWYDPWGQGTLVTVSSASTKGPSVFPLAPSSKS

TSGGTAALGCLVKDYFPEPVTVSWNSGALTSGVHTFPAVLQSSGLYSLSSVVTVPSSSLGTQTYICNV

NHKPSNTKVDKRVEPKSCDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKCKVSNKALPAPIEKTIS

KAKGQPFRPEVHLLPPSREEMTKNQVSLTCLARGFYPKDIAVEWESNGQPENNYKTTPSRQEPSQG

TTTFAVTSKLTVDKSRWQQGNVFSCSVMHEALHNHYTQKTISLSPG heavy chain for #A02-SEED(AG) antibody (amino acid sequence)
SEQ ID NO: 101:
QVQLQESGPGLVKPSGTLSLTCAVSGGSISSNNWWSWVRQPPGKGLEWIGEIYHSGSTSYNPSLKS

RVTISVDKSKNQFSLKLSSVTAADTAVYYCARATDWFDLWGQGTLVTVSSASTKGPSVFPLAPSSKST

SGGTAALGCLVKDYFPEPVTVSWNSGALTSGVHTFPAVLQSSGLYSLSSVVTVPSSSLGTQTYICNVN

HKPSNTKVDKRVEPKSCDKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCKVSNKALPAPIEKTISK

AKGQPFRPEVHLLPPSREEMTKNQVSLTCLARGFYPKDIAVEWESNGQPENNYKTTPSRQEPSQGT

TTFAVTSKLTVDKSRWQQGNVFSCSVMHEALHNHYTQKTISLSPG heavy chain for #G04-SEED(AG) antibody (amino acid sequence)
SEQ ID NO: 102:
QVQLQESGPGLVKPSGTLSLTCAVSGGSISSNNWWSWVRQPPGKGLEWIGEIYHSGSTSYNPSLKS

RVTISVDKSKNQFSLKLSSVTAADTAVYYCARGTDWYDLWGQGTLVTVSSASTKGPSVFPLAPSSKS

TSGGTAALGCLVKDYFPEPVTVSWNSGALTSGVHTFPAVLQSSGLYSLSSVVTVPSSSLGTQTYICNV

NHKPSNTKVDKRVEPKSCDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKCKVSNKALPAPIEKTIS

KAKGQPFRPEVHLLPPSREEMTKNQVSLTCLARGFYPKDIAVEWESNGQPENNYKTTPSRQEPSQG

TTTFAVTSKLTVDKSRWQQGNVFSCSVMHEALHNHYTQKTISLSPG heavy chain for #D02-SEED(AG) antibody (amino acid sequence)

SEQ ID NO: 103:
QVQLQESGPGLVKPSGTLSLTCAVSGGSISSNNWWSWVRQPPGKGLEWIGEIYHSGSTSYNPSLKS

RVTISVDKSKNQFSLKLSSVTAADTAVYYCARGTDWIDTWGQGTLVTVSSASTKGPSVFPLAPSSKST

SGGTAALGCLVKDYFPEPVTVSWNSGALTSGVHTFPAVLQSSGLYSLSSVVTVPSSSLGTQTYICNVN

HKPSNTKVDKRVEPKSCDKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCKVSNKALPAPIEKTISK

AKGQPFRPEVHLLPPSREEMTKNQVSLTCLARGFYPKDIAVEWESNGQPENNYKTTPSRQEPSQGT

TTFAVTSKLTVDKSRWQQGNVFSCSVMHEALHNHYTQKTISLSPG heavy chain for #D01-SEED(AG) antibody (amino acid sequence)
SEQ ID NO: 104:
QVQLQESGPGLVKPSGTLSLTCAVSGGSISSNNWWSWVRQPPGKGLEWIGEIYHSGSTSYNPSLKS

RVTISVDKSKNQFSLKLSSVTAADTAVYYCARATDWFDHWGQGTLVTVSSASTKGPSVFPLAPSSKS

TSGGTAALGCLVKDYFPEPVTVSWNSGALTSGVHTFPAVLQSSGLYSLSSVVTVPSSSLGTQTYICNV

NHKPSNTKVDKRVEPKSCDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKCKVSNKALPAPIEKTIS

KAKGQPFRPEVHLLPPSREEMTKNQVSLTCLARGFYPKDIAVEWESNGQPENNYKTTPSRQEPSQG

TTTFAVTSKLTVDKSRWQQGNVFSCSVMHEALHNHYTQKTISLSPG heavy chain for #C01-SEED(AG) antibody (amino acid sequence)
SEQ ID NO: 105:
QVQLQESGPGLVKPSGTLSLTCAVSGGSISSNNWWSWVRQPPGKGLEWIGEIYHSGSTSYNPSLKS

RVTISVDKSKNQFSLKLSSVTAADTAVYYCARATDWFDAWGQGTLVTVSSASTKGPSVFPLAPSSKS

TSGGTAALGCLVKDYFPEPVTVSWNSGALTSGVHTFPAVLQSSGLYSLSSVVTVPSSSLGTQTYICNV

NHKPSNTKVDKRVEPKSCDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKCKVSNKALPAPIEKTIS

KAKGQPFRPEVHLLPPSREEMTKNQVSLTCLARGFYPKDIAVEWESNGQPENNYKTTPSRQEPSQG

TTTFAVTSKLTVDKSRWQQGNVFSCSVMHEALHNHYTQKTISLSPG heavy chain for #A07-SEED(AG) antibody (amino acid sequence)
SEQ ID NO: 106:
QVQLQESGPGLVKPSGTLSLTCAVSGGSISSNNWWSWVRQPPGKGLEWIGEIYHSGSTSYNPSLKS

RVTISVDKSKNQFSLKLSSVTAADTAVYYCARGTDWYDPWGQGTLVTVSSASTKGPSVFPLAPSSKS

TSGGTAALGCLVKDYFPEPVTVSWNSGALTSGVHTFPAVLQSSGLYSLSSVVTVPSSSLGTQTYICNV

NHKPSNTKVDKRVEPKSCDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKCKVSNKALPAPIEKTIS

KAKGQPFRPEVHLLPPSREEMTKNQVSLTCLARGFYPKDIAVEWESNGQPENNYKTTPSRQEPSQG

TTTFAVTSKLTVDKSRWQQGNVFSCSVMHEALHNHYTQKTISLSPG heavy chain for #B10-SEED(AG) antibody (nucleic acid sequence)
SEQ ID NO: 107:
CAGGTGCAGCTGCAGGAGTCGGGCCCAGGACTGGTGAAGCCTTCGGGGACCCTGTCCCTCACC

TGCGCTGTCTCTGGTGGCTCCATCAGCAGTAATAACTGGTGGAGTTGGGTCCGCCAGCCCCCAG

GGAAGGGGCTGGAGTGGATTGGGGAAATCTATCATAGTGGGAGCACCAGCTACAACCCGTCCCT

CAAGAGTCGAGTCACCATATCAGTAGACAAGTCCAAGAACCAGTTCTCCCTGAAGCTGTCCTCTG

TGACCGCCGCGGACACGGCCGTGTATTACTGTGCGAGAGCCACCGATTGGTACGACCCGTGGG

GCCAGGGAACCCTGGTCACTGTCTCTTCAGCTAGCACCAAGGGCCCATCGGTCTTCCCCCTGGC

ACCCTCCTCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACACCTTCCC

-continued

```
GGCTGTCCTACAGTCCTCAGGACTCTACTCCCTCAGCAGCGTGGTGACCGTGCCCTCCAGCAGC

TTGGGCACCCAGACCTACATCTGCAACGTGAATCACAAGCCCAGCAACACCAAGGTGGACAAGA

GAGTTGAGCCCAAATCTTGTGACAAAACTCACACATGCCCACCGTGCCCAGCACCTGAACTCCTG

GGGGGGCCCTCAGTCTTCCTCTTCCCCCCAAAACCCAAGGACACCCTCATGATCTCTAGAACCC

CTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCAC

GTACCGTGTGGTCAGCGTCCTCACCGTCCTGCACCAGGACTGGCTGAATGGCAAGGAGTACAAG

TGCAAGGTCTCCAACAAAGCCCTCCCAGCCCCCATCGAGAAAACGATATCCAAAGCCAAAGGGC

AGCCCTTCCGGCCAGAGGTCCACCTGCTGCCCCCATCACGGGAGGAGATGACCAAGAACCAGG

TCAGCCTGACCTGCCTGGCACGCGGCTTCTATCCCAAGGACATCGCCGTGGAGTGGGAGAGCA

ATGGGCAGCCGGAGAACAACTACAAGACCACGCCTTCCCGGCAGGAGCCCAGCCAGGGCACCA

CCACCTTCGCTGTGACCTCGAAGCTCACCGTGGACAAGAGCAGATGGCAGCAGGGGAACGTCTT

CTCATGCTCCGTGATGCATGAGGCTCTGCACAACCACTACACGCAGAAGACCATCTCCCTGTCCC

CGGGT
``` heavy chain for #A02-SEED(AG) antibody (nucleic acid sequence)
SEQ ID NO: 108:
```
CAGGTGCAGCTGCAGGAGTCGGGCCCAGGACTGGTGAAGCCTTCGGGGACCCTGTCCCTCACC

TGCGCTGTCTCTGGTGGCTCCATCAGCAGTAATAACTGGTGGAGTTGGGTCCGCCAGCCCCCAG

GGAAGGGGCTGGAGTGGATTGGGGAAATCTATCATAGTGGGAGCACCAGCTACAACCCGTCCCT

CAAGAGTCGAGTCACCATATCAGTAGACAAGTCCAAGAACCAGTTCTCCCTGAAGCTGTCCTCTG

TGACCGCCGCGGACACGGCCGTGTATTACTGTGCGAGAGCGACCGACTGGTTTGACCTCTGGG

GCCAGGGAACCCTGGTCACCGTCTCTTCAGCTAGCACCAAGGGCCCATCGGTCTTCCCCCTGGC

ACCCTCCTCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACACCTTCCC

GGCTGTCCTACAGTCCTCAGGACTCTACTCCCTCAGCAGCGTGGTGACCGTGCCCTCCAGCAGC

TTGGGCACCCAGACCTACATCTGCAACGTGAATCACAAGCCCAGCAACACCAAGGTGGACAAGA

GAGTTGAGCCCAAATCTTGTGACAAAACTCACACATGCCCACCGTGCCCAGCACCTGAACTCCTG

GGGGGGCCCTCAGTCTTCCTCTTCCCCCCAAAACCCAAGGACACCCTCATGATCTCTAGAACCC

CTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCAC

GTACCGTGTGGTCAGCGTCCTCACCGTCCTGCACCAGGACTGGCTGAATGGCAAGGAGTACAAG

TGCAAGGTCTCCAACAAAGCCCTCCCAGCCCCCATCGAGAAAACGATATCCAAAGCCAAAGGGC

AGCCCTTCCGGCCAGAGGTCCACCTGCTGCCCCCATCACGGGAGGAGATGACCAAGAACCAGG

TCAGCCTGACCTGCCTGGCACGCGGCTTCTATCCCAAGGACATCGCCGTGGAGTGGGAGAGCA

ATGGGCAGCCGGAGAACAACTACAAGACCACGCCTTCCCGGCAGGAGCCCAGCCAGGGCACCA

CCACCTTCGCTGTGACCTCGAAGCTCACCGTGGACAAGAGCAGATGGCAGCAGGGGAACGTCTT

CTCATGCTCCGTGATGCATGAGGCTCTGCACAACCACTACACGCAGAAGACCATCTCCCTGTCCC

CGGGT
``` heavy chain for #G04-SEED(AG) antibody (nucleic acid sequence)
SEQ ID NO: 109:
```
CAGGTGCAGCTGCAGGAGTCGGGCCCAGGACTGGTGAAGCCTTCGGGGACCCTGTCCCTCACC

TGCGCTGTCTCTGGTGGCTCCATCAGCAGTAATAACTGGTGGAGTTGGGTCCGCCAGCCCCCAG
```

```
GGAAGGGGCTGGAGTGGATTGGGGAAATCTATCATAGTGGGAGCACCAGCTACAACCCGTCCCT

CAAGAGTCGAGTCACCATATCAGTAGACAAGTCCAAGAACCAGTTCTCCCTGAAGCTGTCCTCTG

TGACCGCCGCGGACACGGCCGTGTATTACTGTGCGAGAGGGACGGACTGGTATGACCTCTGGG

GCCAGGGAACCCTGGTCACCGTCTCTTCGGCTAGCACCAAGGGCCCATCGGTCTTCCCCCTGGC

ACCCTCCTCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACACCTTCCC

GGCTGTCCTACAGTCCTCAGGACTCTACTCCCTCAGCAGCGTGGTGACCGTGCCCTCCAGCAGC

TTGGGCACCCAGACCTACATCTGCAACGTGAATCACAAGCCCAGCAACACCAAGGTGGACAAGA

GAGTTGAGCCCAAATCTTGTGACAAAACTCACACATGCCCACCGTGCCCAGCACCTGAACTCCTG

GGGGGGCCCTCAGTCTTCCTCTTCCCCCCAAAACCCAAGGACACCCTCATGATCTCTAGAACCC

CTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCAC

GTACCGTGTGGTCAGCGTCCTCACCGTCCTGCACCAGGACTGGCTGAATGGCAAGGAGTACAAG

TGCAAGGTCTCCAACAAAGCCCTCCCAGCCCCCATCGAGAAAACGATATCCAAAGCCAAAGGGC

AGCCCTTCCGGCCAGAGGTCCACCTGCTGCCCCCATCACGGGAGGAGATGACCAAGAACCAGG

TCAGCCTGACCTGCCTGGCACGCGGCTTCTATCCCAAGGACATCGCCGTGGAGTGGGAGAGCA

ATGGGCAGCCGGAGAACAACTACAAGACCACGCCTTCCCGGCAGGAGCCCAGCCAGGGCACCA

CCACCTTCGCTGTGACCTCGAAGCTCACCGTGGACAAGAGCAGATGGCAGCAGGGGAACGTCTT

CTCATGCTCCGTGATGCATGAGGCTCTGCACAACCACTACACGCAGAAGACCATCTCCCTGTCCC

CGGGT heavy chain for #D02-SEED(AG) antibody (nucleic acid sequence)
SEQ ID NO: 110:
CAGGTGCAGCTGCAGGAGTCGGGCCCAGGACTGGTGAAGCCTTCGGGGACCCTGTCCCTCACC

TGCGCTGTCTCTGGTGGCTCCATCAGCAGTAATAACTGGTGGAGTTGGGTCCGCCAGCCCCCAG

GGAAGGGGCTGGAGTGGATTGGGGAAATCTATCATAGTGGGAGCACCAGCTACAACCCGTCCCT

CAAGAGTCGAGTCACCATATCAGTAGACAAGTCCAAGAACCAGTTCTCCCTGAAGCTGTCCTCTG

TGACCGCCGCGGACACGGCCGTGTATTACTGTGCGAGAGGGACTGATTGGATCGACACCTGGG

GCCAGGGAACCCTGGTCACTGTCTCCTCAGCTAGCACCAAGGGCCCATCGGTCTTCCCCCTGGC

ACCCTCCTCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACACCTTCCC

GGCTGTCCTACAGTCCTCAGGACTCTACTCCCTCAGCAGCGTGGTGACCGTGCCCTCCAGCAGC

TTGGGCACCCAGACCTACATCTGCAACGTGAATCACAAGCCCAGCAACACCAAGGTGGACAAGA

GAGTTGAGCCCAAATCTTGTGACAAAACTCACACATGCCCACCGTGCCCAGCACCTGAACTCCTG

GGGGGGCCCTCAGTCTTCCTCTTCCCCCCAAAACCCAAGGACACCCTCATGATCTCTAGAACCC

CTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCAC

GTACCGTGTGGTCAGCGTCCTCACCGTCCTGCACCAGGACTGGCTGAATGGCAAGGAGTACAAG

TGCAAGGTCTCCAACAAAGCCCTCCCAGCCCCCATCGAGAAAACGATATCCAAAGCCAAAGGGC

AGCCCTTCCGGCCAGAGGTCCACCTGCTGCCCCCATCACGGGAGGAGATGACCAAGAACCAGG

TCAGCCTGACCTGCCTGGCACGCGGCTTCTATCCCAAGGACATCGCCGTGGAGTGGGAGAGCA

ATGGGCAGCCGGAGAACAACTACAAGACCACGCCTTCCCGGCAGGAGCCCAGCCAGGGCACCA

CCACCTTCGCTGTGACCTCGAAGCTCACCGTGGACAAGAGCAGATGGCAGCAGGGGAACGTCTT
```

CTCATGCTCCGTGATGCATGAGGCTCTGCACAACCACTACACGCAGAAGACCATCTCCCTGTCCC

CGGGT heavy chain for #D01-SEED(AG) antibody (nucleic acid sequence)
SEQ ID NO: 111:
CAGGTGCAACTGCAGGAGTCGGGCCCAGGACTGGTGAAGCCTTCGGGGACCCTGTCCCTCACC

TGCGCTGTCTCTGGTGGCTCCATCAGCAGTAATAACTGGTGGAGTTGGGTCCGCCAGCCCCCAG

GGAAGGGGCTGGAGTGGATTGGGGAAATCTATCATAGTGGGAGCACCAGCTACAACCCGTCCCT

CAAGAGTCGAGTCACCATATCAGTAGACAAGTCCAAGAACCAGTTCTCCCTGAAGCTGTCCTCTG

TGACCGCCGCGGACACGGCCGTGTATTACTGTGCGAGAGCCACGGATTGGTTTGACCACTGGG

GCCAGGGAACCCTGGTCACCGTCTCCTCAGCTAGCACCAAGGGCCCATCGGTCTTCCCCCTGGC

ACCCTCCTCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACACCTTCCC

GGCTGTCCTACAGTCCTCAGGACTCTACTCCCTCAGCAGCGTGGTGACCGTGCCCTCCAGCAGC

TTGGGCACCCAGACCTACATCTGCAACGTGAATCACAAGCCCAGCAACACCAAGGTGGACAAGA

GAGTTGAGCCCAAATCTTGTGACAAAACTCACACATGCCCACCGTGCCCAGCACCTGAACTCCTG

GGGGGGCCCTCAGTCTTCCTCTTCCCCCCAAAACCCAAGGACACCCTCATGATCTCTAGAACCC

CTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCAC

GTACCGTGTGGTCAGCGTCCTCACCGTCCTGCACCAGGACTGGCTGAATGGCAAGGAGTACAAG

TGCAAGGTCTCCAACAAAGCCCTCCCAGCCCCCATCGAGAAAACGATATCCAAAGCCAAAGGGC

AGCCCTTCCGGCCAGAGGTCCACCTGCTGCCCCCATCACGGGAGGAGATGACCAAGAACCAGG

TCAGCCTGACCTGCCTGGCACGCGGCTTCTATCCCAAGGACATCGCCGTGGAGTGGGAGAGCA

ATGGGCAGCCGGAGAACAACTACAAGACCACGCCTTCCCGGCAGGAGCCCAGCCAGGGCACCA

CCACCTTCGCTGTGACCTCGAAGCTCACCGTGGACAAGAGCAGATGGCAGCAGGGGAACGTCTT

CTCATGCTCCGTGATGCATGAGGCTCTGCACAACCACTACACGCAGAAGACCATCTCCCTGTCCC

CGGGT heavy chain for #C01-SEED(AG) antibody (nucleic acid sequence)
SEQ ID NO: 112:
CAGGTGCAGCTGCAGGAGTCGGGCCCAGGACTGGTGAAGCCTTCGGGGACCCTGTCCCTCACC

TGCGCTGTCTCTGGTGGCTCCATCAGCAGTAATAACTGGTGGAGTTGGGTCCGCCAGCCCCCAG

GGAAGGGGCTGGAGTGGATTGGGGAAATCTATCATAGTGGGAGCACCAGCTACAACCCGTCCCT

CAAGAGTCGAGTCACCATATCAGTAGACAAGTCCAAGAACCAGTTCTCCCTGAAGCTGTCCTCTG

TGACCGCCGCGGACACGGCCGTGTATTACTGTGCGAGAGCGACCGATTGGTTTGACGCCTGGG

GCCAGGGAACCCTGGTCACCGTCTCTTCAGCTAGCACCAAGGGCCCATCGGTCTTCCCCCTGGC

ACCCTCCTCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACACCTTCCC

GGCTGTCCTACAGTCCTCAGGACTCTACTCCCTCAGCAGCGTGGTGACCGTGCCCTCCAGCAGC

TTGGGCACCCAGACCTACATCTGCAACGTGAATCACAAGCCCAGCAACACCAAGGTGGACAAGA

GAGTTGAGCCCAAATCTTGTGACAAAACTCACACATGCCCACCGTGCCCAGCACCTGAACTCCTG

GGGGGGCCCTCAGTCTTCCTCTTCCCCCCAAAACCCAAGGACACCCTCATGATCTCTAGAACCC

CTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCAC

-continued

```
GTACCGTGTGGTCAGCGTCCTCACCGTCCTGCACCAGGACTGGCTGAATGGCAAGGAGTACAAG

TGCAAGGTCTCCAACAAAGCCCTCCCAGCCCCCATCGAGAAAACGATATCCAAAGCCAAAGGGC

AGCCCTTCCGGCCAGAGGTCCACCTGCTGCCCCCATCACGGGAGGAGATGACCAAGAACCAGG

TCAGCCTGACCTGCCTGGCACGCGGCTTCTATCCCAAGGACATCGCCGTGGAGTGGGAGAGCA

ATGGGCAGCCGGAGAACAACTACAAGACCACGCCTTCCCGGCAGGAGCCCAGCCAGGGCACCA

CCACCTTCGCTGTGACCTCGAAGCTCACCGTGGACAAGAGCAGATGGCAGCAGGGGAACGTCTT

CTCATGCTCCGTGATGCATGAGGCTCTGCACAACCACTACACGCAGAAGACCATCTCCCTGTCCC

CGGGT
``` heavy chain for #A07-SEED(AG) antibody (nucleic acid sequence)
SEQ ID NO: 113:
```
CAGGTGCAGCTGCAGGAGTCGGGCCCAGGACTGGTGAAGCCTTCGGGGACCCTGTCCCTCACC

TGCGCTGTCTCTGGTGGCTCCATCAGCAGTAATAACTGGTGGAGTTGGGTCCGCCAGCCCCCAG

GGAAGGGGCTGGAGTGGATTGGGGAAATCTATCATAGTGGGAGCACCAGCTACAACCCGTCCCT

CAAGAGTCGAGTCACCATATCAGTAGACAAGTCCAAGAACCAGTTCTCCCTGAAGCTGTCCTCTG

TGACCGCCGCGGACACGGCCGTGTATTACTGTGCGAGAGGTACTGACTGGTATGACCCCTGGG

GCCAGGGAACCCTGGTCACCGTCTCCTCAGCTAGCACCAAGGGCCCATCGGTCTTCCCCCTGGC

ACCCTCCTCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACACCTTCCC

GGCTGTCCTACAGTCCTCAGGACTCTACTCCCTCAGCAGCGTGGTGACCGTGCCCTCCAGCAGC

TTGGGCACCCAGACCTACATCTGCAACGTGAATCACAAGCCCAGCAACACCAAGGTGGACAAGA

GAGTTGAGCCCAAATCTTGTGACAAAACTCACACATGCCCACCGTGCCCAGCACCTGAACTCCTG

GGGGGGACCCTCAGTCTTCCTCTTCCCCCCAAAACCCAAGGACACCCTCATGATCTCTAGAACCC

CTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCAC

GTACCGTGTGGTCAGCGTCCTCACCGTCCTGCACCAGGACTGGCTGAATGGCAAGGAGTACAAG

TGCAAGGTCTCCAACAAAGCCCTCCCAGCCCCCATCGAGAAAACGATATCCAAAGCCAAAGGGC

AGCCCTTCCGGCCAGAGGTCCACCTGCTGCCCCCATCACGGGAGGAGATGACCAAGAACCAGG

TCAGCCTGACCTGCCTGGCACGCGGCTTCTATCCCAAGGACATCGCCGTGGAGTGGGAGAGCA

ATGGGCAGCCGGAGAACAACTACAAGACCACGCCTTCCCGGCAGGAGCCCAGCCAGGGCACCA

CCACCTTCGCTGTGACCTCGAAGCTCACCGTGGACAAGAGCAGATGGCAGCAGGGGAACGTCTT

CTCATGCTCCGTGATGCATGAGGCTCTGCACAACCACTACACGCAGAAGACCATCTCCCTGTCCC

CGGGT
```

EXAMPLES

The working examples presented below are intended to illustrate particular embodiments of the invention, and are not intended to limit the scope of the specification or the claims in any way.

Example 1—Generation and Characterization of Anti-FGFR1 Antagonist Antibodies

1.1 Generation of Transient and Stable Expressing Human and Mouse FGFR1

The cDNAs encoding the extracellular domains of human and mouse FGFR1b-IIIb and FGFR1b-IIIc respectively based on NCBI reference NP_075594, NP_056934 (respectively SEQ ID NO: 80 to SEQ ID NO: 83), were generated by gene synthesis with a C-terminal 6-Histidin tag. The cDNAs were subcloned into mammalian expression vector pVAC2 vector (InvivoGen) to encode FGFR1 protein fused to GPI anchoring domain of the placental alkaline phosphatase.

Expi293 cells were transfected using Expifectamine (Thermofischer) and CHO cells were transfected using a Nucleofector II Device (Amaxa Biosystems) with the vector encoding the using the Nucleofection system and followed by selection with hygromycin B. Minipools were screened for FGFR1 expression using FACS. Single cells were sorted from best minipools by FACS and expanded. Selection of the clone with highest expression of FGFR1 was done by FACS.

After 3 days, FGFR1 cell surface expression was assessed by FACS using an anti-FGFR1-IgG1 (at 1 µg/ml and 10 µg/ml) or control antibody (1 µg/ml and 10 µg/ml) as primary antibody, and use R-Phycoerythrin-conjugated AffiniPure F(ab')2 Fragment Goat anti-Human IgG, Fcγ Fragment Specific (Jackson Immuno Research #109-116-098) as secondary antibody.

1.2. Preparation of Recombinant Proteins

Recombinant human FGFR1b-IIIb and FGFR1b-IIIc extracellular domains (respectively SEQ ID NO: 80, SEQ ID NO: 81) were fused to a 6-Histidine tag. The FGFR1 fusion constructs were prepared using standard recombinant DNA techniques. DNA was transfected into HEK293 cells using PEI for transient expression. Protein was purified from cell supernatant by Nickel chelating affinity column and elution with imidazole. QC analysis was performed on the purified proteins: SDS PAGE under reducing and non-reducing conditions, SEC for determination of purity and apparent MW, UV spectroscopy for concentration determination, and Limulus Amebocyte Lysate assay for measurement of endotoxin contamination. The proteins were functionally tested in vitro by their capacity to inhibit the FGF1- or FGF2-induced phosphorylation of FGFR1 (see Example 1.10). Mouse, rat, cynomolgus monkey and rhesus monkey FGFR1a-IIIc His6-tagged were purchased from Creative BioMart and Sino Biologicals, human FGFR2 and FGFR3 His6-tagged from Sino Biologicals.

1.3 Animals

Anti-FGFR1 human monoclonal antibodies were generated using transgenic rats (OmniRats licensed from Open Monoclonal Technologies, Inc./Ligand Pharmaceuticals, Inc.) that express human antibody genes: human light chain (VLCL or VKCK) and human VH while expressing the rat constant regions of the heavy chain (Geurts et al. 2009, Menoret et al. 2010, Ma et al. 2013, Osborn et al. 2013).

1.4 Generation of Anti-FGFR1 Antibodies Using Phage Display Technology

Monoclonal antibodies specific to FGFR1 were generated using phage display technology and His-tagged human FGFR1b-IIIb and FGFR1b-IIIc antigens. Human phage scFv antibody libraries with natural diversity of heavy and light chains from donors were used for panning. Several different arms were employed to select scFv binding specifically to human FGFR1 (3-4 rounds of selection). 17944 phage clones were screened by ELISA to identify 458 individual FGFR1 binders. 79 clones were confirmed by ELISA for binding specifically to FGFR1 and not FGFR2, FGFR3 or FGFR4. Among those, 25 clones showed binding to cells expressing FGFR1 by FACS. 20 unique clones were successfully reformatted for IgG1 expression. Hit candidates were selected based on their potency to block the phosphorylation of FGFR1 (see Example 1.10). Binding to FGFR1 was originally determined by ELISA and later quantified by Biacore (see Example 1.8) and binding to FGFR1 expressing cells by FACS (see Example 1.7). Three candidates fitted the predefined profile, including mAb #A05.

1.5 Generation of Anti-FGFR1 Antibodies from Rat Hybridoma

Alternatively, to generate fully human monoclonal antibodies to FGFR1, transgenic rats, OmniRats™ were immunized with the His-tagged D2-D3 of human FGFR1b-IIIb and FGFR1b-IIIc antigens (SEQ ID NO: 80 and SEQ ID NO: 81). General immunization schemes were used for Repetitive IMmunization at Multiple Sites as previously described (Kilpatrick et al. 1997). The serum immune response was monitored by FACS using FGFR1-overexpressing cells Cells from lymph nodes were isolated and fused with myeloma cells to generate hybridomas using the conventional PEG method. After ten days of culture in flask in HAT medium, supernatants were harvested and cells were frozen. The supernatants were tested by FACS for binding to cells overexpressing FGFR1.

Monoclonal hybridoma cells were single sorted in 96-well plates and grown in HAT medium for several days. 7896 supernatants were tested for binding to cells expressing murine FGFR1. 414 supernatants were confirmed binding to FGFR1 by ELISA. 177 unique clones were reformatted and expressed as IgGs. 27 clones were confirmed to bind to FGFR1 by ELISA and to FGFR1 expressing cells by FACS (see Example 1.7).

None of the antibodies selected from phage or hybridoma bound to D2 domain (SEQ ID NO: 84) (as tested by ELISA) and were able to inhibit pFGFR1 in the absence of ligand (data not shown).

Another immunization of OmniRats was then carried out using a mixture of FGFR1b-IIIb and FGFR1b-IIIc in order to break tolerance and increase diversity. 138 hybridoma supernatants were selected based on their binding to FGFR1 expressing cells. All clones were reformatted and expressed as IgGs. 21 clones were confirmed to bind to FGFR1b-IIIb and FGFR1b-IIIc, murine FGFR1a-IIIc and the D2 domain of FGFR1 by ELISA including mAb #A08.

1.6 Antibody Expression and Purification

Antibody heavy and light chains were subcloned separately into the pTT5 vector and were transiently co-expressed in Expi293 cells after transfection using the Expi-Fectamine transfection reagent. Cells were incubated for 7 days with shaking at 37° C. in a 5% CO2 humidified incubator. Conditioned medium was harvested and centrifuged to remove cell debris. The antibodies were purified from culture supernatants by Protein A affinity chromatography using standard methods. The following QC analysis was performed on the purified proteins: SDS-PAGE under reducing and non-reducing conditions, SEC for determination of purity and apparent MW, UV spectroscopy for concentration determination, and Limulus Amebocyte Lysate assay for measurement of endotoxin contamination.

1.7 Cell-Based Binding Assays for Anti-FGFR1 Antibodies

Binding of anti-FGFR1 antibodies to cell lines was assessed by FACS. Briefly, approximately $1\times10^5$ FGFR1 expressing cells were resuspended in FACS buffer (DPBS with 1% FBS) containing serial dilutions of anti-FGFR1 antibodies ranging from 100 to 0 nM, and incubated for 30 min on ice. Cells were washed and resuspended in FACS buffer containing FITC-conjugated goat anti-human IgG Fc antibody (Jackson ImmunoResearch Laboratories #109-

096-098) for 30 min on ice. Cells were then centrifuged and resuspended in FACS buffer containing 7-AAD and 1% neutral buffered formalin. Analysis was done on a Guava EasyCyte instrument (MilliporeSigma). Median Flow Intensity (MFI) was plotted against antibody concentration and GraphPad Prism software was used to calculate $EC_{50}$ values. The mAbs #A08 and #A05 were highly specific to human and murine FGFR1 expressing cells and showed no binding to the control parental Expi293 cells (data not shown).

1.8 Determination of the $K_D$ of Anti-FGFR1 mAb Variants for FGFR1

Binding affinities of anti-FGFR1 antibodies to FGFR1 were measured by Surface Plasmon Resonance (SPR) using a GE Healthcare BIAcore 4000 instrument as follows. Goat anti-human Fc antibody (Jackson ImmunoResearch Laboratories #109-005-098) was first immobilized on BIAcore carboxymethylated dextran CM5 chip using direct coupling to free amino groups following the procedure described by the manufacturer. Antibodies were then captured on the CM5 biosensor chip to achieve approximately 200 response units (RU). Binding measurements were performed using the running HBS-EP+ buffer. A 2-fold dilution series of His-tagged FGFR1 proteins were injected at a flow rate of 30 µl/min at 25° C. Association rates ($k_{on}$, per mol/s) and dissociation rates ($k_{off}$, per s) were calculated using a simple 1:1 Langmuir binding model (Biacore 4000 Evaluation Software). The equilibrium dissociation constant ($K_D$, mol) was calculated as the ratio of $k_{off}/k_{on}$. One of the anti-FGFR1 antibodies which were identified as described above (mAb #A08) bound to FGFR1b-IIIb and FGFR1b-IIIc with a similar affinity of $10 \times 10^{-12}$ and $17 \times 10^{-12}$ M (Table 1). While the anti-FGFR1 antibody mAb #A05 bound to both FGFR1b-IIIb and FGFR1b-IIIc (as shown via ELISA testing), binding measured by SPR against FGFR1b-IIIc revealed an affinity of $10 \times 10^{-12}$ M.

1.9 Binding Selectivity to FGFR1 Against Other Family Members

The binding selectivity of the antibodies were tested by ELISA against the different FGFR family members: FGFR1, FGFR2, FGFR3 and FGFR4. Briefly plates were coated overnight with the different His6-tagged FGFR proteins, after blocking with 1% Bovine Serum albumin, 1 or 0.1 µg/ml of anti-FGFR1 antibodies were incubated for 1 h at room temperature. After washing, the bound antibodies were incubated for 1 h at room temperature with a peroxidase affiniPure F(ab')2 Fragment goat anti-human Fc (Jackson ImmunoResearch Laboratories #109-036-098) and detection was performed using the TMB HRP Substrate solution (BioFx Lab # TMBW-1000-01). At 0.1 µg/ml, only mAb #A05 showed strong signal against FGFR2 and FGFR4 while mAb #A08 had a very weak binding with FGFR2 (data not showed).

Figure 2:
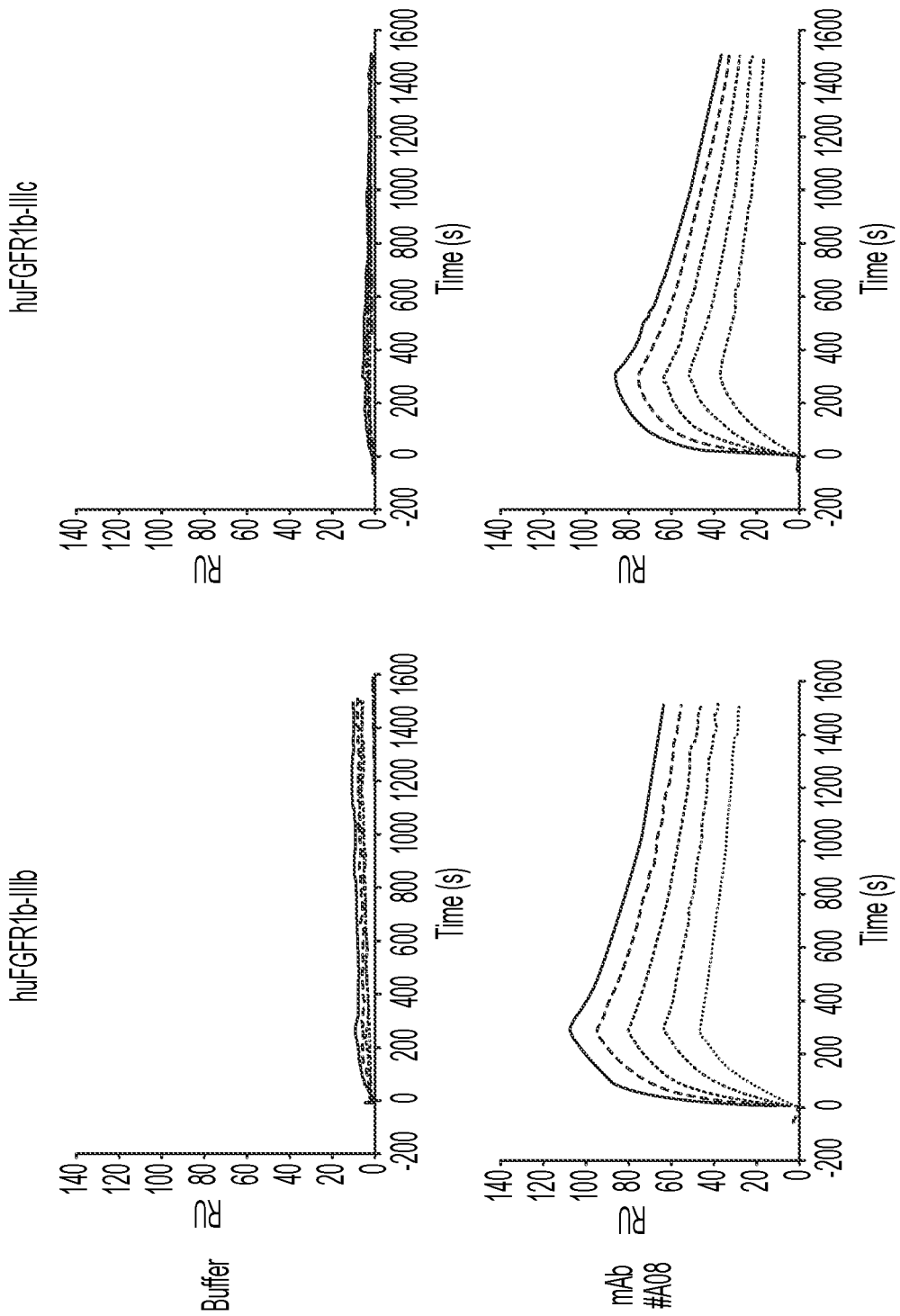
FIG. 2 depicts the binding sensorgrams of mAb #A08 and buffer to FGFR1-IIIb and -IIIc, FGFR2 and FGFR3. The binding signals (response unit, RU) are plotted against time. Buffer control and mAb #A08 were tested for binding to huFGFR1b-IIIb, -IIIc, huFGFR2 and huFGFR3.
Figure 2:
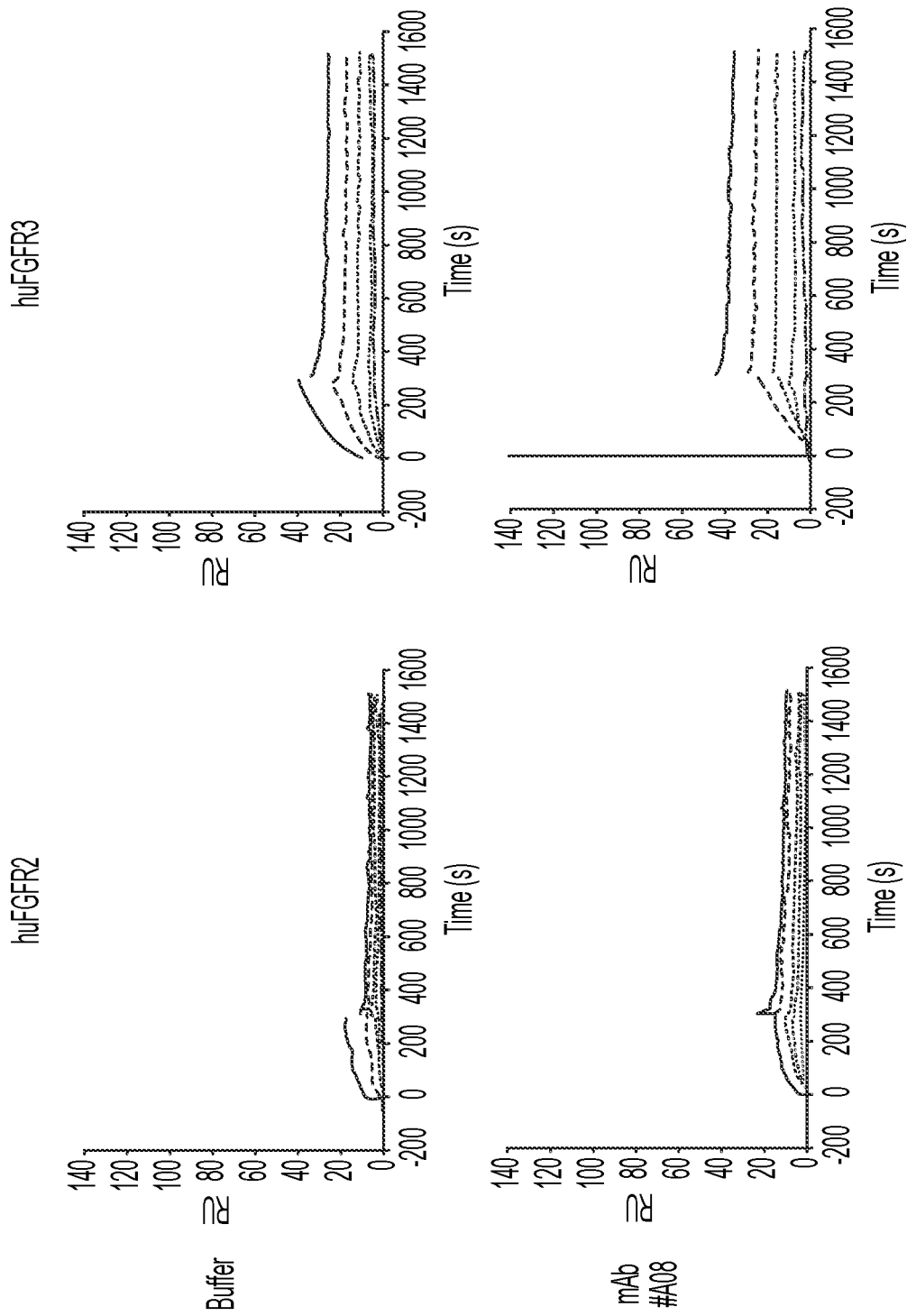

The binding affinities of mAb #A08 against FGFR1, FGFR2 and FGFR3 were measured by SPR using a similar protocol to the one disclosed in example 1.8 with the following modification: for FGFR2 and FGFR3, the serial dilutions were started at 1000 nM. The kinetic profiles (FIG. 2) clearly demonstrate that mAb #A08 has a similar profile than the buffer negative control and therefore does not bind to FGFR2 nor FGFR3. mAb #A08 binds specifically to FGFR1-IIIb and FGFR1-IIIc with a similar affinity profile (also see Table 1).

1.10 Inhibition of Phospho-FGFR1 (pFGFR1) in NCI-H520 Cell Line

For the inhibition of activation of FGFR1, NCI-H520 cells (from lung squamous cell carcinoma) were plated at $2 \times 10^4$ cells/well in 10% FCS-containing RPMI medium and incubated overnight at 37° C., 5% $CO_2$. Cells were starved for 24 h by replacing the medium by serum free RPMI medium. Five-fold serial dilutions of anti-FGFR1 antibodies or one-armed molecules (i.e. monovalent SEEDbodies) were prepared in Optimem medium and added the cells for 45 min at 37° C. Human FGF1 (Biomol #50440.50) or FGF2 (Biomol #50361.50) were mixed with Heparin (Sigma Aldrich #H3149) and added to the cells for final concentrations of 100 ng/ml FGF1 or FGF2 and 5 µg/ml Heparin for 10 min at 37° C. Cells were washed and lysed for 20 min on ice with Triton lysis buffer. Lysed cells were filtered through Lysate filterplates by centrifugation. The phosphorylated FGFR1 (pFGFR1) was quantified using beads coated with a rabbit anti-FGFR1 (Cell Signaling, clone D8E4) for capture, and a mouse anti-phospho-FGFR (Tyr653/654) (Cell Signaling clone 55H2) and a donkey anti-mouse-PE (Dianova #715-116-151) for detection with a Luminex instrument. The untreated control (non-stimulated) was set as 100% and calculated the antibody treated samples as % control. % control of pFGFR1 was plotted against antibody concentration and GraphPad Prism software was used to calculate $IC_{50}$ values (Table 2). The activity of the anti-FGFR1 antibodies were compared with the activity of a FGF trap, a molecule consisting of the extracellular domains of FGFR1 fused to a Fc domain to trap the FGFR1 ligands, designated as FP-1039 (WO2007014123) and 2 other anti-FGFR1, IMC-H7 that binds to FGFR1-IIIb and FGFR1-IIIc and IMC-A1 that binds to FGFR1-IIIc only (WO2005037235). All molecules inhibited pFGFR1 in the FGF-1- and FGF2-induced cells but only FP-1039 and the mAb #A08 inhibited completely pFGFR1 in the presence of FGF1. mAb #A08 showed the strongest inhibition activity with $IC_{50}$ of 4/0.2 nM and mAb #A05 had an $IC_{50}$ of 1/1 nM for respectively FGF1-/FGF2-induced pFGFR1. Only mAb #A08 and IMC-H7 inhibited the ligand-independent pFGFR1 in this assay.

Example 2—Optimization of mAb #A08 and mAb #A05

2.1 Heavy and Light Chain Variants

The amino acid sequences of the variable regions of the mAb #A08 and mAb #A05 heavy (SEQ ID NO: 1 and SEQ ID NO: 26 respectively; VH) and of the variable regions of the mAb #A08 and mAb #A05 light (SEQ ID NO: 2 and SEQ ID NO: 28 respectively; VL) chains were separately modified, by altering both framework region and CDR sequences in the heavy and light chain variable regions. The purpose of these sequence alterations was either to mutate framework amino acid residues to the most homologous human germline residue found at that position, to increase potency in relevant cellular assay, to improve manufacturability of the molecule by preventing Asp isomerization, Asn deamidation and Met oxidation, or to deplete the antibody of in silico identified human T-cell epitopes, thereby reducing or abolishing immunogenicity in humans.

Two heavy chain variants (SEQ ID NO: 24, and SEQ ID NO: 27) were constructed, as a human IgG1 heavy chain isotype and are denoted respectively #A08 VH lead (corresponding to SEQ ID NO: 24; heavy chain of #A08 lead) and #A05 VH lead (SEQ ID NO: 27, heavy chain of #A05 lead).

According to IMGT numbering scheme, the following mutations were made:
A08 VH lead: N92S
A05 VH lead: Q1E, M2V In addition, several mutations were made in the amino acid sequences of the CDR of heavy variable region of mAb #A08 (SEQ ID NO: 6 to SEQ ID NO: 17) as follows:
A08 CDR1: S35G (SEQ ID NO: 6) or S31N, N37H (SEQ ID NO: 7)
A08 CDR2: T65V (SEQ ID NO: 8)
A08 CDR3: G107A, P117X (SEQ ID NO: 9) with X being any residues selected from the group consisting of P, Q, A, L, H, S or T; G107A, F115Y (SEQ ID NO: 10), G107A, F1151, P117T (SEQ ID NO: 11), G107S (SEQ ID NO: 12), F1151, P117A (SEQ ID NO: 13), F115Y, P117L (SEQ ID NO: 14), G107X with X being any residues selected from the group consisting of S or V (SEQ ID NO: 15), G107A, T108K, P117A (SEQ ID NO: 16), or G107A, F115Y (SEQ ID NO: 17).

Two light chain variants were constructed, in a human lambda background, and are denoted #A08 VL lead (SEQ ID NO: 25, light chain of #A08 lead), and #A05 VL lead (SEQ ID NO: 29, light chain of #A05 lead) comprise the following mutations (according to IMGT numbering; residues that are underlined are located in one of the CDRs):
A08 VL lead: Q1S, A2Y
A05 VL lead: D84G, T85N, S86T, C105S, N114S The original and variant heavy and light chains were combined in all possible pair-wise combinations to generate a number of functional fully human anti-FGFR1 antibodies. Hit optimization candidates were selected based on their binding activity to FGFR1 (by ELISA and FACS).

Example 3—SEEDbody Production and Testing 3.1 Bioproduction, Clarification and Purification The monovalent SEEDbody #A08, having amino acid sequences corresponding to SEQ ID NO: 46 and SEQ ID NO: 41 (heavy chains) and SEQ ID NO: 50 (light chain), was produced from CHO-LF cells (generating afucosylated protein for enhanced ADCC). Cell cultures were conducted in batch mode in a 250L Single-use Bioreactor. Cells were grown in proprietary-CHO fed-batch growth media supplemented with glucose at 37° C. The cultures were fed with a mixture of proprietary feed components on days 3, 5, 7 and 10 days post inoculation.

Crude conditioned media from the bioreactor runs were clarified using 2.2 m² Millistak+Pod DOHC (Millipore MD0HC10FS1) and 1.1 m2 Millistak+Pod XOHC (Millipore #MX0HC01FS1) filters, followed by terminal filtration with a Millipore Opticap XL3 0.5/0.2 µm filter (Millipore #KHGES03HH3).

The SEEDbody was then purified using standard methods and formulated in 10 mM histidine. This SEEDbody #A08 was used in all the subsequent assays (see sections 3.2 to 3.8). #A08 heavy and light chains were also used to construct a standard IgG1 antibody also used in subsequent assays (see sections 3.2 and 3.3)

3.2 Affinity Measurement

The affinities of the anti-FGFR1 SEEDbody (monovalent) and the IgG1 (bivalent) were compared by Biacore using a protocol similar to the one described in Example 1.8. The SPR experiments measured a similar binding affinity to FGFR1b-IIIc for the SEEDbody and the IgG1 formats. The formatting into the monovalent molecule has not altered the binding kinetic of the Fab portion (data not shown).

3.3 Inhibition of Ligand-Dependent and -Independent pFGFR1 in H520 Cells

Using a similar protocol as the one described in example 1.10, the activities of the antibodies as bivalent (IgG1) and monovalent (SEEDbody) were compared. The data showed that all antibodies had an $IC_{50}$~10-fold higher when reformatted into the monovalent format most likely due to a loss in the avidity on the cell surface (Table 3). Only clone #A08 retained inhibition activity as a monovalent molecule in both FGF1-, FGF2-induced and in the absence of ligand with $IC_{50}$ of 70, 6 and 20 nM respectively. Similar findings were obtained on downstream signaling events such as the phosphorylation of FRS2 and Erk1/2 (data not shown).

3.4 ADCC Assay with DMS53 and NCI-H520 Cells

Figure 3:
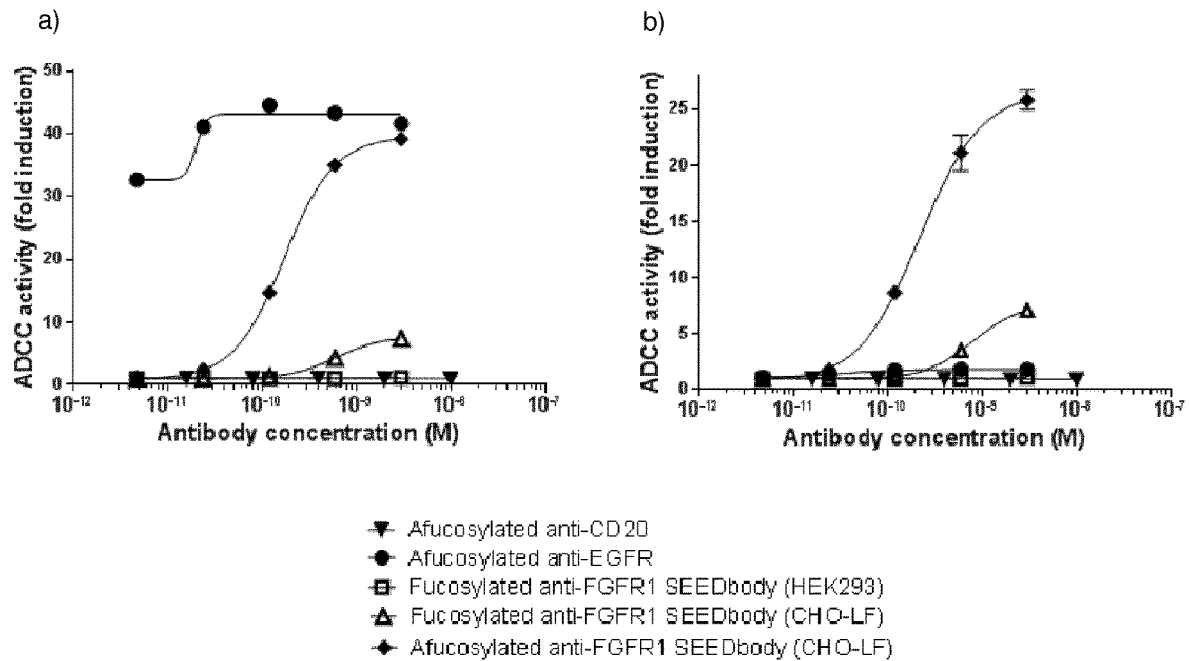
FIG. 3 shows the ADCC activity of anti-FGFR1 SEEDbody against a) DMS53 and b) NCI-H520 cells. The fold induction versus control (no effector cells) was plotted against concentration (molar, M). Afucosylated anti-CD20 antibody (enhanced ADCC function) was used a negative control; afucosylated anti-EGFR antibody (enhanced ADCC function) was used a positive control in DMS53 cells (which express EGFR) and as negative control in NCI-H520 cells (which don't express EGFR). The SEEDbody A08 was tested as fucosylated (with ADCC function) or afucosylated (enhanced ADCC function).

The capacity of the anti-FGFR1 antibodies to induce ADCC was evaluated using the ADCC Reporter Bioassay Core Kit (Promega #G7018). Briefly DMS53 (from human small cell lung carcinoma) or NCI-H520 target cells were plated at $1.25 \times 10^4$ cells/well in a 96-well plate and grown overnight in medium containing low-IgG serum. Culture medium was then replaced by pre-warmed ADCC assay buffer. Five-fold serial dilutions of antibodies were added to the cells together with the effector cells (Jurkat NFAT-luc provided with the kit) with the ratio of 6:1 (effector: target cells) of in the pre-warmed ADCC assay buffer. Plates were incubated for 6 h at 37° C. After equilibrating the plates for 15 min at room temperature, the Bio-Glo luciferase assay reagent was added. Following 5 min incubation at room temperature, luminescence was measured using an Envision 2104 plate reader. The fold induction was calculated as the ratio of signal (induced minus background)/signal (no antibody control minus background). The fold induction was plotted versus the antibody concentration. Control afucosylated anti-EGFR (positive control for EGFR-positive-DMS53 cells), afucosylated anti-CD20 (negative control), anti-FGFR1 produced in CHO-LF cells in presence or absence of fucose were compared for ADCC activity against the DMS53 (FIG. 3a) and NCI-H520 (FIG. 3b) cells. The afucosylated anti-FGFR1 SEEDbody induced ADCC of both DMS53 and NCI-H520 cells while the fucosylated protein produced in CHO-LF cells induced moderate ADCC.

3.5 DMS53 Tumor Xenograft

Seven to nine weeks old H2d RAG3 mice (Taconic) were subcutaneously injected with $5 \times 10^6$ DMS53 cells with Matrigel (BD #354234). Tumors were allowed to grow and animals were randomized into 5 groups of 10 animals each to give mean tumor volume of approximately 115 mm³. Groups were injected intraperitoneally twice weekly with vehicle (in 10 mM Histidine buffer) or SEEDbody #A08 at 25, 12, 6, 3 mg/kg (formulation buffer see example 3.1). Animals were checked daily and body weight was measured twice weekly. Tumors were measured twice weekly by collecting length and width. The tumor volume was calculated using the following formula: Length×Width×Width/2.

Figure 4:
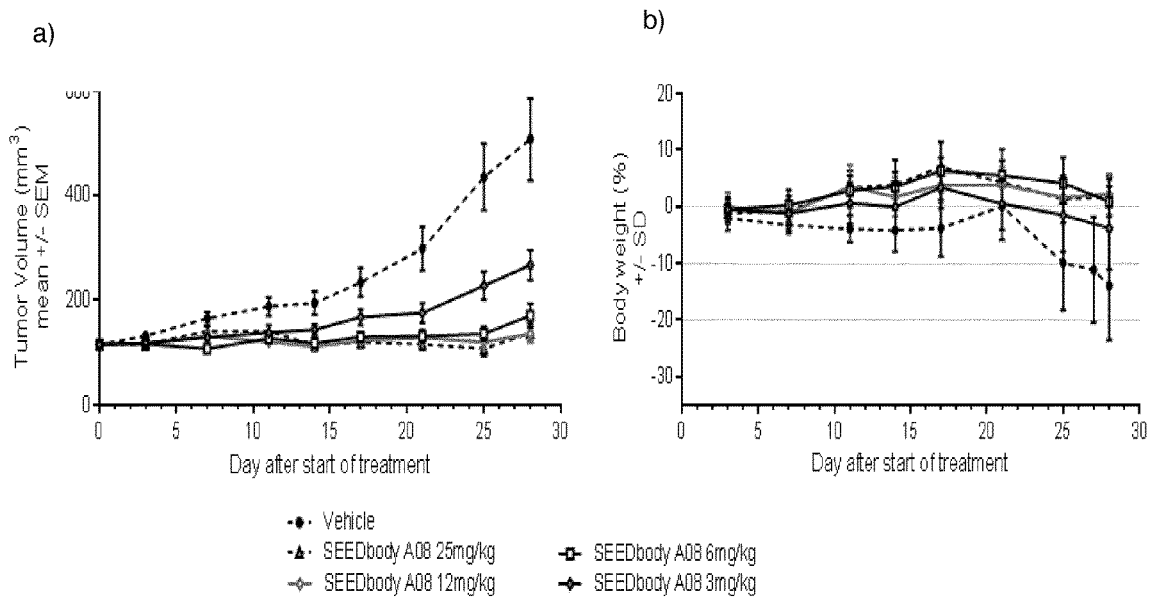
FIG. 4 shows in vivo efficacy study of the monovalent anti-FGFR1 molecule (SEEDbody A08) as compared to the vehicle in DMS53-xenograft bearing mice. Results were reported as a) effect on tumor volume as depicted with the tumor volume (mm3) plotted against day after treatment b) effect on body weight of the mice as represented by % of body weight as a function of time after treatment.

The (monovalent) SEEDbody anti-FGFR1 inhibited the growth of the DMS53 xenograft in a dose dependent manner and already inducing strong tumor growth inhibition at 6 mg/kg (FIG. 4a).

While the DMS53 model induced cachexia on vehicle-treated mice, stable body weight was observed in SEEDbody #A08-treated mice (FIG. 4b).

Nineteen days after the last treatment, tumor were collected to measure the level of pFGFR1 using a similar protocol as described in example 1.10.

Figure 5:
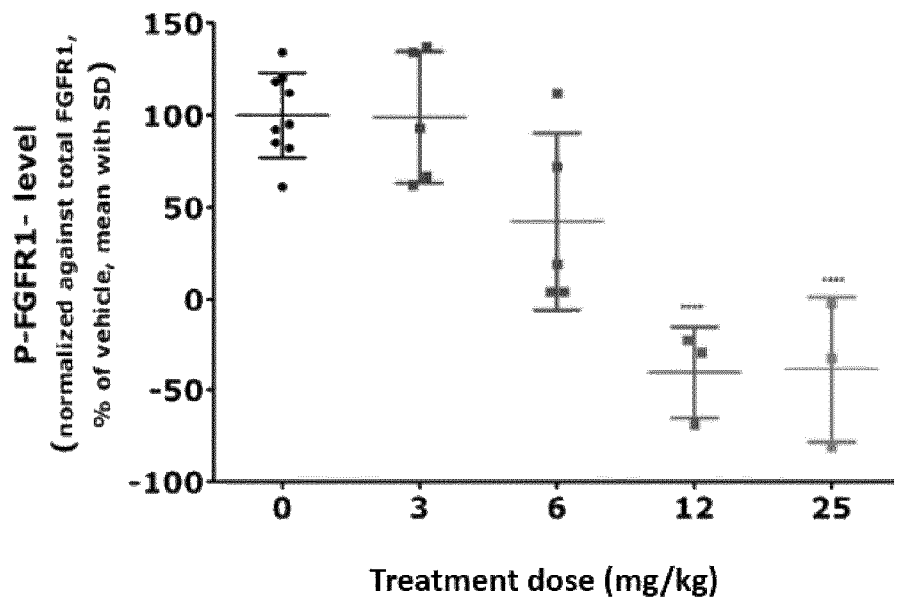
FIG. 5 shows the pFGFR1 levels in DMS53 tumor xenografts harvested 19 days after the last treatment.

FIG. 5 shows the dose dependent in vivo inhibition of pFGFR1 in DMS53 xenografts by the treatment with the SEEDbody #A08. Full inhibition (lower limit of detection) was obtained at 12 mg/kg.

3.6 NCI-H226 Xenograft Model

Eleven weeks old H2d RAG3 mice (Taconic) were subcutaneously injected on the flank with $2.5 \times 10^6$ NCI-H226 cells (from human lung squamous cell carcinoma, mesothelioma). Tumors were allowed to grow to reach a tumor volume ranging from 47 to 94 mm³, and animals were randomized into 6 groups of 10 animals. Groups were injected intraperitoneally twice weekly with vehicle (in 10 mM histidine buffer) or SEEDbody #A08 at 50 mg/kg (formulated according to example 3.1).

Animals were checked daily and body weight was measured twice weekly. Tumors were measured twice weekly by collecting length and width. The tumor volume was calculated using the following formula: Length×Width×Width/2.

The (monovalent) SEEDbody anti-FGFR1 inhibited the growth of the NCI-H226 xenograft, similarly to one of the standard of care (Pemetrexel/Cisplatin) (data not shown). The body weight was affected in all groups, suggesting a model related effect (data not shown).

3.7 Effect of SEEDbody on Mouse Plasma Levels of FGF23

Figure 6:
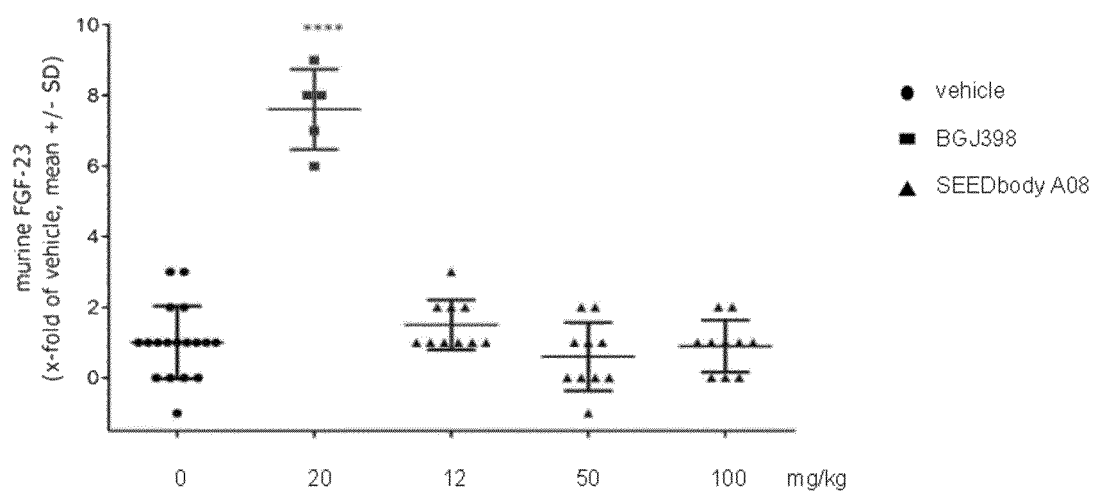
FIG. 6 shows the in vivo effect 24 hours after injection in mice of the SEEDbody A08, a pan-FGFR inhibitor (BGJ398) and vehicle control on mouse FGF23 levels in plasma.

It was important to test whether the SEEDbody #A08 (as a monovalent form) had similar effect in vivo than the pan-FGFR inhibitors: interference with FGF23 pathway resulting in elevated plasma FGF23 levels (Wohrle et al. 2013, Yanochko et al. 2013). Plasma samples of mice injected with vehicle, pan-FGFR inhibitor (BGJ39) at 20 mg/kg, and SEEDbody #A08 at 12, 50 and 100 mg/kg were collected after 24 h and quantification of mouse FGF23 was performed using the mouse FGF-23 ELISA Kit (Millipore #EZMFGF23-43K) according to manufacturer recommendations. Data demonstrate that in contrast to the pan-FGFR inhibitor, the SEEDbody #A08 does not modify the hormonal FGF23 levels in plasma for all tested doses (FIG. 6).

Example 4—Epitope Mapping

4.1 Domain Mapping

Figure 7:
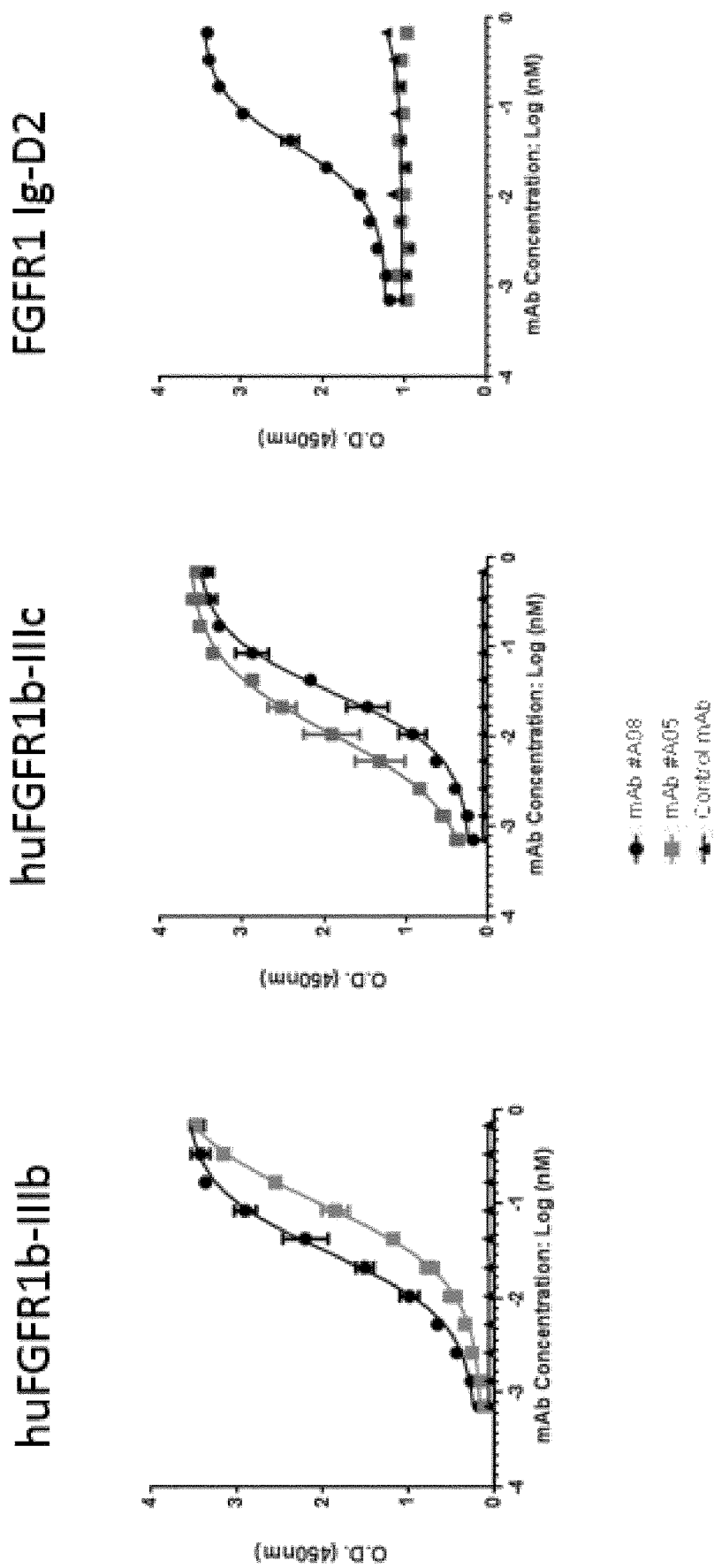
FIG. 7 shows the domain mapping to Ig-D2 for mAb #A08, mAb #A05 and a control antibody (anti-Hen Egg Lysozyme) by ELISA. The optical density measured at 450 nm was plotted against antibody concentrations (with a $Log_{10}$ scale).

A domain-level epitope mapping of the anti-FGFR1 antibodies was established by generating partial constructs of FGFR1b-IIIc (SEQ ID NO: 81) for the domain D2 (residues 1-142 of SEQ ID No. 81, corresponding to SEQ ID NO: 84) and D3 (residues 142-164 of SEQ ID No. 81, corresponding to SEQ ID NO: 85). Antibody binding against those D2 domain was tested by ELISA and against D2 (FIG. 7). Data showed that mAb #A08 binds to the D2 domain and mAb #A05 does not bind to D2. The ELISA data have also demonstrated that mAb #A05 binds both FGFR1b-IIIb and FGFR1b-IIIc. The SPR data have confirmed the binding of mAb #A08 to the D2 domain and of mAb #A05 to the D3 domain (data not shown).

4.2. Epitope Mapping by Hydrogen-Deuterium Exchange

The extracellular domain of FGFR1 antigen (SEQ ID NO: 81) was incubated in heavy water ($D_2O$) solution to allow amide protons on the protein backbone to exchange with deuterons from the solvent, in either the presence or absence of excess anti-FGFR1 Fab or a non-specific Fab. The samples were digested with protease and analyzed by liquid chromatography-mass spectrometry (LC-MS) to determine the level of deuteration in each peptide.

Figures 8, 9:
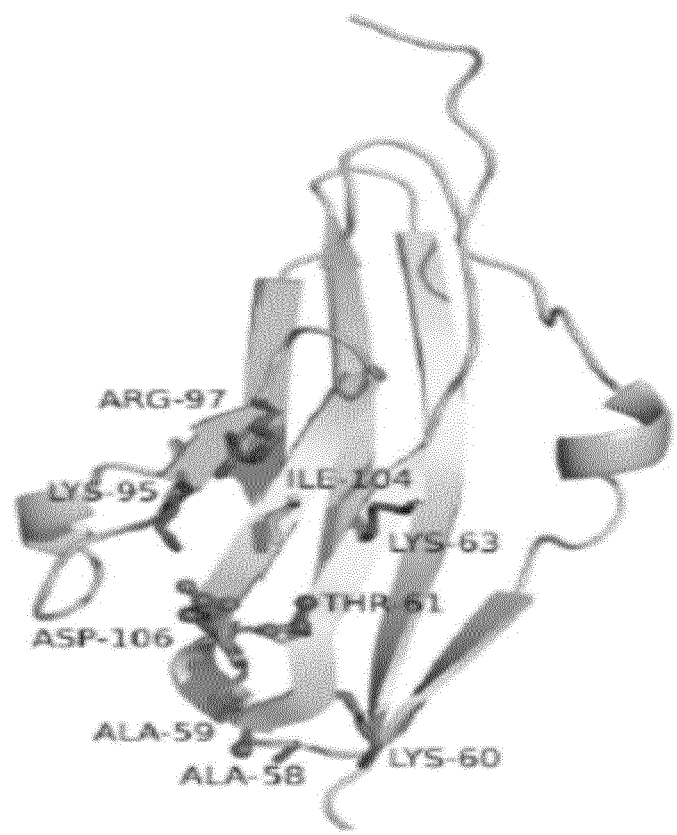
FIG. 8 shows the sequence of the extracellular domain (fused to a 6 amino acid His tag, SEQ ID NO: 81) of FGFR1b-IIIc. Peptides that could be identified by Mass Spectrometry are indicated by grey bars. Those that showed protection from Hydrogen-Deuterium exchange in the presence of the Fab are represented by black bars. Peptides that could not be analyzed are highlighted by underlining and italicizing in the sequence.
FIG. 9 shows the epitope of mAb #A08 on FGFR1 (35-137). The backbone of FGFR1 is shown in a ribbon representation. Amino acids which, when mutated to alanine or glycine (if original amino acid is alanine) destabilize the mAb #A08-FGFR1 binding by more than 0.7 kcal/mol are shown as sticks.

The Fab corresponding to mAb #A08 was used instead of the full IgG in order to simplify the mass spectrometry analysis by decreasing the number of peptides generated by protease digestion. Despite this, some regions remained that could not be identified and analyzed (underlined, italicized sequence portions in FIG. 8), however these regions represent a small fraction of the sequence, and reside all in the Ig like domain D3, distant from the epitope containing region of mAb #A08. This method could not therefore be used for mAb #A05 which has its epitope located in the D3 domain. Several peptides from antigen were observed to have a significantly reduced rate of exchange of protons for deuterons in the presence of the Fab than in its absence, suggesting that at least some residues for these peptides are in direct contact with the Fab and constitute a conformational epitope that are proximal in the three-dimensional structure of FGFR1 and constitute a single patch on the surface of the antigen (FIG. 9).

In summary, HD exchange identified a conformational epitope localized near the 2 peptides
  i. residues 52-63 of SEQ ID NO: 81, in extracellular domain plus His tag, and
  ii. residues 79-95 of SEQ ID NO: 81, in extracellular domain plus His tag, that contains the functional epitope of mAb #A08.

4.3 Mutagenesis

To obtain a finer, residue-level mapping of the epitope and to complement the HD exchange data, molecular modelling and manual inspection of the crystal structure of FGFR1 [(Beenken et al. 2012); PDB record 3OJV] was used to select solvent exposed residues within and around the epitope identified by HD exchange. The selected residues were mutated either to alanine (large to small) or to glycine if the selected residue was alanine. In total 35 point mutants were designed, expressed and purified in HEK cells, and tested for binding to mAb #A08 using surface plasmon resonance as described in Example 1.8. The affinity of the antibody for wild-type and each mutant was determined and used to calculate the contribution of each epitope residue to the binding energy.

The results are summarized in the Table 4. Variant were compared to wild-type D2. The change in the Gibbs free energy of binding of mutant relative to the wild-type D2 construct ($\Delta\Delta G_{mut}$) was derived from the ratio of the wild-type and mutant $K_D$. The temperature midpoint of fluorescently monitored thermal denaturation is given for the wild type and mutant proteins. The percent monomer as determined by analytical SEC is given. For $K_D$ and $T_{1/2}$, the mean and standard deviation is given where n>1. It was important to confirm that the lack of binding of mAb #A08 to K60A, T61A, K63A, and K95A point mutants was indeed due to loss of hotspot residues and not to global unfolding of the antigen. The structural integrity of the mutated proteins was confirmed using a fluorescence monitored thermal unfolding (FMTU) assay in which the protein is incubated with a dye that is quenched in aqueous solution but fluoresces when bound by exposed hydrophobic residues. As the temperature increases, thermal denaturation of the protein exposes the hydrophobic core residues and tis can be monitored by an increase in fluorescence of the dye. A melting curve is fit to the data with the Boltzmann equation outlined in Equation 1, adapted from (Bullock et al. 1997) to determine the temperature at the inflection point of the curve ($T_{1/2}$). The calculated $T_{1/2}$ are reported in the Table 4.

Equation 1:

$$F = F_{min} + \frac{F_{max} - F_{min}}{1 + e^{\frac{T_m - x}{dx}}}$$

All mutants displayed a two state transition similar to wild-type D2, indicating a folded structure at room temperature. The majority of variant proteins have melting points similar to wild-type FGFR1-IIIb or -IIIc or the wild-type D2. Notable exceptions include variants of L53A, A55G, V56A, G92A, G93A, and Y94A which each have uncharacteristic melting curves in the FMTU assay that indicate potential local or global unfolding of these variants. Of these potentially unstable variants only mutation Y94A has an effect on binding affinity. While this residue is in the vicinity of the epitope, the tyrosine sidechain is oriented on the opposite side of the beta sheet from the other epitope residues. Taken together, it is unlikely that the sidechain atoms of tyrosine 94 participate in meaningful interactions with the mAb #A08.

Example 5—Affinity Maturation

Figure 10:
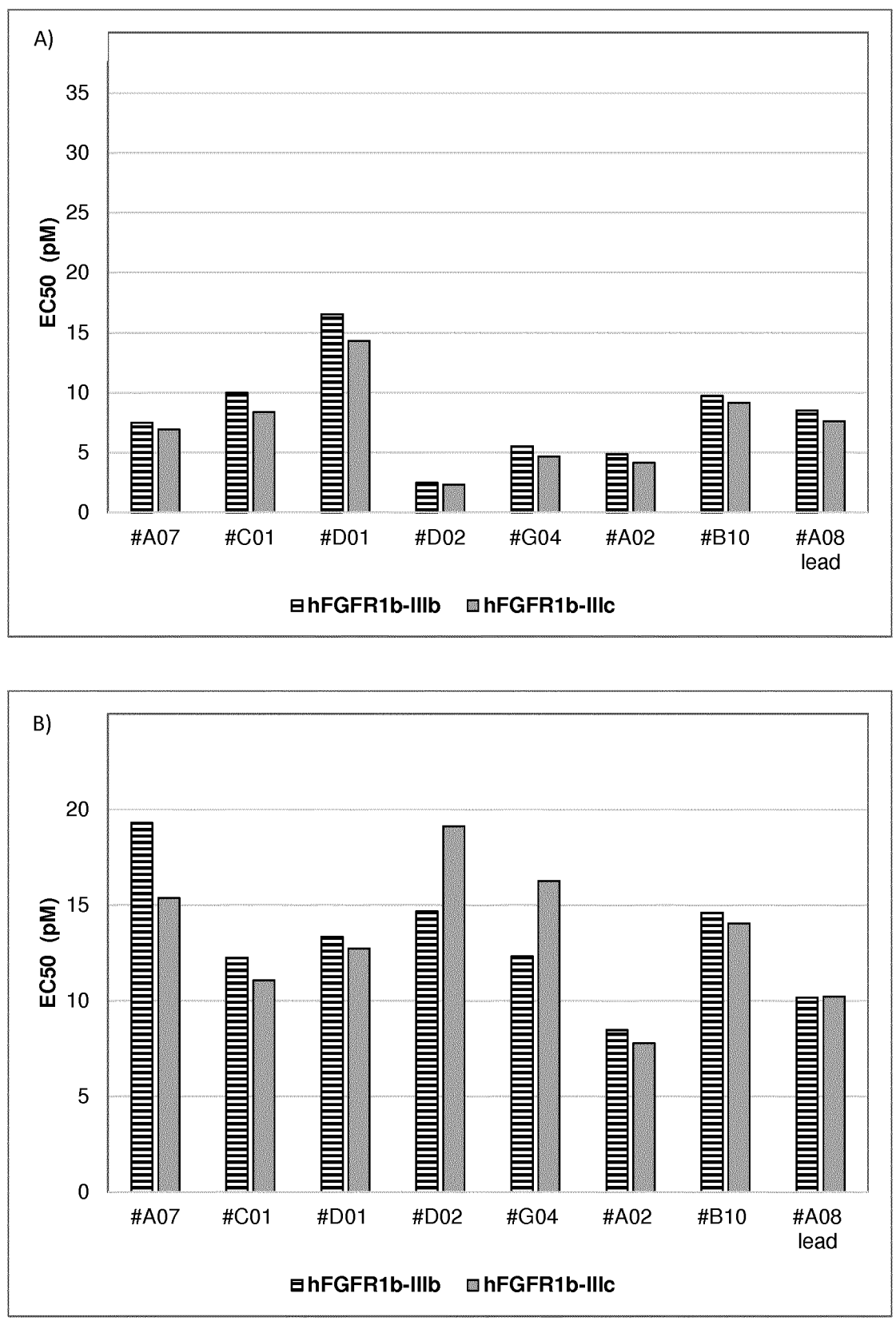
FIG. 10 shows the binding of various affinity matured mAbs on human FGFR1b (IIIb) (hFGFR1b-IIIb) and human FGFR1b (IIIc) (hFGFR1b-IIIc) as measured by ELISA. A) mAbs are in the IgG1 format, B) mAbs are in the monovalent SEEDbody format.

The antibody #A08 both as an IgG1 (bivalent) and as a SEEDbody (monovalent), was affinity matured using the yeast display technology described in (Rhiel et al. 2014) and performing light chain shuffling from immunized OmniRats and naïve human library followed by CDR-H3 parsimonious mutagenesis. Following several sorting rounds, yeast clones were picked, unique clones were reformatted as described in Examples 1.6 and 3.1. The binding affinities of the anti-FGFR1 molecules against human FGFR1b-IIIb) and human FGFR1b-IIIc) were measured by ELISA using a similar protocol as described in Example 1.9. The OD450 was plotted against the antibody concentration and GraphPad Prism software was used to calculate $EC_{50}$ values (see FIG. 10). The affinity matured anti-FGFR1 molecules have similar binding activities, to mAb #A08 in both formats (i.e. IgG1 and SEEDbody), with the exception of mAb #D01 in the IgG1 format that showed higher EC50 value (15 pM compared to 8 pM for mAb #A08) and SEEDbody #A07. The best results were obtained with mAb #A02 and #C01 showing an EC50 improvement in both IgG1 and SEEDbody formats.

The affinities to human FGFR1b-IIIb for the affinity matured clones reformatted as IgG and monovalent SEEDbodies were measured by BIAcore (using a protocol similar to the one described in Example 1.8) and compared to those of mAb #08 (Table 5). Results showed that all clones have lower $K_D$ than mAb #08 $K_D$ within 2- to 4-fold with the exception of clones #G04 and #D02 that have higher $K_D$ and showed also a different KD depending on their format.

TABLE 1

Affinities to different species

|  | huFGFR1b-IIIb | huFGFR1b-IIIc | huFGFR1a-IIIc | muFGFR1a-IIIc | ratFGFR1a-IIIc | rheFGFR1a-IIIc | cyFGFR1a-IIIc |
|---|---|---|---|---|---|---|---|
| mAb #A05 | NB | 0.001 | 0.2 | 1.6 | NB | 0.51 | NB |
| mAb #A08 | 0.01 | 0.017 | 0.7 | 2.3 | 2.2 | 0.46 | NB |

TABLE 2 pFGFR1 inhibition in H520 cells ($IC_{50}$, M)

| Molecule | Selectivity | Non-stimulated | Inhibition of P-FGFR1 FGF1 stimulated | FGF2 stimulated |
|---|---|---|---|---|
| FP-1039 | FGF1, 2, 4, 6, 8b, 9, 16, 17, 18 | inactive | 5E−08 | 3E−08 |
| IMC-H7 | FGFR1-IIIb + c D2 | 1E−07* | 1E−07 * | 2E−09 |
| IMC-A1 | FGFR1-IIIc D3 | inactive | 1E−06 * | 1E−07 |
| mAb #A05 | FGFR1-IIIb + c D3 FGFR2, 4 | inactive | 1E−09 * | 1E−09 |
| mAb #A08 | FGFR1-IIIb + c D2 | ~1E−06 # | 4E−09 | 2E−10 |

TABLE 3

Comparison of IgG1 (bivalent) and SEEDbody (monovalent) formats for pFGFR1 inhibition in NCI-H520 cells ($IC_{50}$ in M)

|  | Non-stimulated | | FGF1 | | FGF2 | |
|---|---|---|---|---|---|---|
|  | IgG1 | SEEDbody | IgG1 | SEEDbody | IgG1 | SEEDbody |
| IMC-H7 | 7E−08 * | 3E−07 | 6E−07 * | >1E−06 | 6E−09 | 1E−07 |
| A05 | >1E−06 | >1E−06 | 8E−09 * | >1E−06 | 3E−09 | 4E−07 |
| A08 | 5E−08 * | 2E−08 | 1E−09 | 7E−08 | 2E−10 | 6E−09 |

TABLE 4

Affinity data with all FGFR1 mutants

| Mutation | $K_D$ (nM) | $\Delta\Delta G_{mut}$ (kcal/mol) | Stability $T_{1/2}$ (° C.) | % monomer |
|---|---|---|---|---|
| FGFR1b | 0.47 ± 0.04 | NC | 44.5 ± 1.8 | 100 |
| FGFR1c | 0.48 ± 0.07 | NC | 49.2 | 96 |
| F3FR1c-D2 | 0.19 ± 0.03 | 0 | 52.5 ± 0.9 | 97.8 |
| F3FR1c-D3 | NBD | NC | NDC | >95 |
| S45A | 0.21 | 0.05 | 53.6 | 97.6 |
| E47A | 0.26 | 0.17 | 53.2 | 98.1 |
| K48A | 0.09 | −0.46 | 51.4 ± 0.8 | 95.6 |
| E50A | 0.2 | 0.02 | 52 | >95 |
| K51A | 0.31 | 0.27 | 49.6 | 98.4 |
| K52A | 0.23 | 0.11 | 51.4 | 92.7 |
| L53A | 0.29 | 0.25 | ND | 98.2 |
| H54A | 0.36 | 0.37 | 48.6 | 96.3 |
| A55G | 0.22 | 0.07 | ND | 98.5 |
| V56A | 0.27 | 0.2 | ND | 95.6 |
| P57A | 0.41 | 0.44 | 52.3 ± 0.1 | 95.5 |
| A58G* | 2.20 ± 0.32 | 1.44 | 50.5 | 94.6 |
| A59G* | 3.91 ± 2.32 | 1.78 | 60.7 | 98.4 |
| K60A** | 13.44 ± 0.29 | 2.51 | 53.8 ± 2.1 | 98.1 |
| T61A** | 5.89 ± 0.07 | 2.02 | 51.0 ± 1.7 | 95.2 |
| K63A** | 13.93 ± 1.40 | 2.53 | 50.6 ± 2.2 | 95.8 |
| K65A | 0.18 ± 0.02 | −0.04 | 55.3 ± 0.6 | 99.3 |
| K86A | 0.18 | −0.06 | 50 | 98.4 |
| P87A | 0.22 | 0.08 | 51.7 | >95 |
| D88A | 0.16 | −0.1 | 54.4 | 93.7 |
| H89A | 0.19 | −0.02 | 52.9 | 98.5 |
| I91A | 0.19 | 0 | 53.1 | 95.7 |
| G92A | 0.28 ± 0.02 | 0.21 | ND | 94.4 |
| G93A | 0.32 ± 0.02 | 0.29 | ND | 97.4 |
| Y94A | 0.99 ± 0.17 | 0.96 | ND | 96.5 |
| K95A** | 5.86 ± 2.51 | 2.02 | 50.6 ± 0.2 | 96.8 |
| V96A | 0.19 | −0.02 | 47.6 | >95 |
| R97A* | 4.25 ± 1.46 | 1.83 | 50.8 ± 1.0 | 96.4 |
| Y98A | 0.18 | −0.04 | 51.3 | 97.5 |
| A99G | 0.18 | −0.05 | 53.0 ± 0.1 | 96.7 |
| T100A | 0.24 | 0.12 | 51.6 ± 1.7 | 97.8 |
| S102A | 0.16 | −0.13 | 52.2 | >95 |
| I104A | 0.93 ± 0.37 | 0.93 | 53.5 | 98.4 |
| D106A* | 4.93 | 1.92 | 53.1 ± 2.0 | 95.2 |
| S107A | 0.24 ± 0.07 | 0.13 | 54.1 | >95 |

TABLE 5

Affinities ($K_D$, nM) of the affinity matured clones as IgG (bivalent) and SEEDbody (monovalent) to human FGFR1b-IIIc

| Names | IgG1 | KD(nM)SEEDbody |
|---|---|---|
| #A08 | 0.06 | 0.08 |
| #B10 | 0.02 | 0.02 |
| #A02 | 0.05 | 0.06 |
| #D01 | 0.03 | 0.05 |
| #C01 | 0.03 | 0.04 |
| #A07 | 0.06 | 0.04 |

REFERENCES

Aviv, H. and P. Leder (1972). "Purification of biologically active globin messenger RNA by chromatography on oligothymidylic acid-cellulose." Proc Natl Acad Sci USA 69: pp. 1408-1412.

Beenken, A., A. V. Eliseenkova, O. A. Ibrahimi, S. K. Olsen and M. Mohammadi (2012). "Plasticity in Interactions of Fibroblast Growth Factor 1 (FGF1) N Terminus with FGF Receptors Underlies Promiscuity of FGF1." J Biol Chem 287: pp. 3067-3078.

Bullock, A. N., J. Henckel, B. S. DeDecker, C. M. Johnson, P. V. Nikolova, M. R. Proctor, D. P. Lane and A. R. Fersht (1997). "Thermodynamic stability of wild-type and mutant p53 core domain." Proc Natl Acad Sci USA 94: pp. 14338-14342.

Chirgwin, J. M., A. E. Przybyla, R. J. MacDonald and W. J. Rutter (1979). "Isolation of biologically active ribonucleic acid from sources enriched in ribonuclease." Biochemistry 18: pp. 5294-5299.

Chothia, C. and A. M. Lesk (1987). "Canonical structures for the hypervariable regions of immunoglobulins." J Mol Biol 196: pp. 901-917.

Davis, J. H., C. Aperlo, Y. Li, E. Kurosawa, Y. Lan, K. M. Lo and J. S. Huston (2010). "SEEDbodies: fusion proteins based on strand-exchange engineered domain (SEED) CH3 heterodimers in an Fc analogue platform for asymmetric binders or immunofusions and bispecific antibodies." Protein Eng Des Sel 23: pp. 195-202.

Eswarakumar, V. P., I. Lax and J. Schlessinger (2005). "Cellular signaling by fibroblast growth factor receptors." Cytokine Growth Factor Rev 16: pp. 139-149.

Fernig, D. G. and J. T. Gallagher (1994). "Fibroblast growth factors and their receptors: an information network controlling tissue growth, morphogenesis and repair." Prog Growth Factor Res 5: pp. 353-377.

Geurts, A. M., G. J. Cost, Y. Freyvert, B. Zeitler, J. C. Miller, V. M. Choi, S. S. Jenkins, A. Wood, X. Cui, X. Meng, A. Vincent, S. Lam, M. Michalkiewicz, R. Schilling, J. Foeckler, S. Kalloway, H. Weiler, S. Menoret, I. Anegon, G. D. Davis, L. Zhang, E. J. Rebar, P. D. Gregory, F. D. Urnov, H. J. Jacob and R. Buelow (2009). "Knockout rats via embryo microinjection of zinc-finger nucleases." Science 325: pp. 433.

Jiao, H., P. Arner, S. L. Dickson, H. Vidal, N. Mejhert, C. Henegar, M. Taube, C. Hansson, A. Hinney, P. Galan, C. Simon, A. Silveira, A. Benrick, J. O. Jansson, A. Bouloumie, D. Langin, M. Laville, C. Debard, T. Axelsson, M. Ryden, J. Kere, K. Dahlman-Wright, A. Hamsten, K. Clement and I. Dahlman (2011). "Genetic association and gene expression analysis identify FGFR1 as a new susceptibility gene for human obesity." J Clin Endocrinol Metab 96: pp. E962-966.

Johnson, D. E. and L. T. Williams (1993). "Structural and functional diversity in the FGF receptor multigene family." Adv Cancer Res 60: pp. 1-41.

Kabat, E. A., T. T. Wu, H. M. Perry, K. S. Gottesman and C. Foeller (1991). Sequences of proteins of immunological interest.

Katoh, M. and H. Nakagama (2014). "FGF receptors: cancer biology and therapeutics." Med Res Rev 34: pp. 280-300.

Kilpatrick, K. E., S. A. Wring, D. H. Walker, M. D. Macklin, J. A. Payne, J. L. Su, B. R. Champion, B. Caterson and G. D. McIntyre (1997). "Rapid development of affinity matured monoclonal antibodies using RIMMS." Hybridoma 16: pp. 381-389.

Lefranc, M.-P. (1997) "Unique database numbering system for immunogenetic analysis". Immunology Today, 18, 509, LIGM:194

Ma, B., M. J. Osborn, S. Avis, L. H. Ouisse, S. Menoret, I. Anegon, R. Buelow and M. Bruggemann (2013). "Human antibody expression in transgenic rats: comparison of chimeric IgH loci with human VH, D and JH but bearing different rat C-gene regions." J Immunol Methods 400-401: pp. 78-86.

Menoret, S., A. L. Iscache, L. Tesson, S. Remy, C. Usal, M. J. Osborn, G. J. Cost, M. Bruggemann, R. Buelow and I. Anegon (2010). "Characterization of immunoglobulin heavy chain knockout rats." Eur J Immunol 40: pp. 2932-2941.

Nimmerjahn, F. and J. V. Ravetch (2011). "FcgammaRs in health and disease." Curr Top Microbiol Immunol 350: pp. 105-125.

Ornitz, D. M., J. Xu, J. S. Colvin, D. G. McEwen, C. A. MacArthur, F. Coulier, G. Gao and M. Goldfarb (1996). "Receptor specificity of the fibroblast growth factor family." J Biol Chem 271: pp. 15292-15297.

Osborn, M. J., B. Ma, S. Avis, A. Binnie, J. Dilley, X. Yang, K. Lindquist, S. Menoret, A. L. Iscache, L. H. Ouisse, A. Rajpal, I. Anegon, M. S. Neuberger, R. Buelow and M. Bruggemann (2013). "High-Affinity IgG Antibodies Develop Naturally in Ig-Knockout Rats Carrying Germline Human IgH/Igkappa/Iglambda Loci Bearing the Rat CH Region." J Immunol.

Rhiel, L., S. Krah, R. Gunther, S. Becker, H. Kolmar, B. Hock (2014). "REAL-Select: full-length antibody display and library screening by surface capture on yeast cells" PLoS One 9:e114887.

Touat, M., E. Ileana, S. Postel-Vinay, F. Andre and J. C. Soria (2015). "Targeting FGFR Signaling in Cancer." Clin Cancer Res 21: pp. 2684-2694.

Wohrle, S., C. Henninger, O. Bonny, A. Thuery, N. Beluch, N. E. Hynes, V. Guagnano, W. R. Sellers, F. Hofmann, M. Kneissel and D. Graus Porta (2013). "Pharmacological inhibition of fibroblast growth factor (FGF) receptor signaling ameliorates FGF23-mediated hypophosphatemic rickets." J Bone Miner Res 28: pp. 899-911.

Wu, A. L., G. Kolumam, S. Stawicki, Y. Chen, J. Li, J. Zavala-Solorio, K. Phamluong, B. Feng, L. Li, S. Marsters, L. Kates, N. van Bruggen, M. Leabman, A. Wong, D. West, H. Stern, E. Luis, H. S. Kim, D. Yansura, A. S. Peterson, E. Filvaroff, Y. Wu and J. Sonoda (2011). "Amelioration of type 2 diabetes by antibody-mediated activation of fibroblast growth factor receptor 1." Sci Transl Med 3: pp. 113ra126.

Yanochko, G. M., A. Vitsky, J. R. Heyen, B. Hirakawa, J. L. Lam, J. May, T. Nichols, F. Sace, D. Trajkovic and E. Blasi (2013). "Pan-FGFR inhibition leads to blockade of FGF23 signaling, soft tissue mineralization, and cardiovascular dysfunction." Toxicol Sci 135: pp. 451-464.

The invention claimed is:

1. A monoclonal antibody or portion thereof that binds to FGFR1, which comprises:
   a) a heavy chain variable domain comprising H-CDR1, H-CDR2 and H-CDR3, wherein:
      i) H-CDR1 comprises SEQ ID NO: 3;
      ii) H-CDR2 comprises SEQ ID NO: 4;
      iii) H-CDR3 comprises SEQ ID NO: 5; and
   b) a light chain variable domain comprising L-CDR1, L-CDR2 and L-CDR3, wherein:
      i) L-CDR1 comprises SEQ ID NO: 18;
      ii) L-CDR2 comprises SEQ ID NO: 19; and
      iii) L-CDR3 comprises SEQ ID NO: 20.

2. The monoclonal antibody according to claim 1, wherein:
   a) the heavy chain variable domain further comprises Framework Regions H-FR1, H-FR2, H-FR3 and H-FR4, wherein:
      i) H-FR1 comprises SEQ ID NO: 30;
      ii) H-FR2 comprises SEQ ID NO: 31;
      iii) H-FR3 comprises SEQ ID NO: 32; and
      iv) H-FR4 comprises SEQ ID NO: 33; and
   b) the light chain variable domain further comprises Framework regions L-FR1, L-FR2, L-FR3 and L-FR4, wherein:
      i) L-FR1 comprises SEQ ID NO: 34;
      ii) L-FR2 comprises SEQ ID NO: 35;
      iii) L-FR3 comprises SEQ ID NO: 36; and
      iv) L-FR4 comprises SEQ ID NO: 37.

3. The monoclonal antibody according to claim 1, wherein:
   a) the heavy chain variable domain comprises SEQ ID NO: 1; and
   b) the light chain variable domain comprises SEQ ID NO: 2 NO: 2.

4. The monoclonal antibody according to claim 1, wherein said monoclonal antibody comprises a heavy chain constant region, said constant region being selected from the type IgG1, IgG2, IgG3 or IgG4.

5. The monoclonal antibody according to claim 1, wherein said monoclonal antibody comprises an IgA/IgG heavy chain constant region.

6. The monoclonal antibody according to claim 5, wherein the IgA/IgG heavy chain constant region is selected from the group consisting of SEQ ID NO: 46, SEQ ID NO: 47 and SEQ ID NOs: 99-106.

7. A polynucleotide encoding the heavy chain of the monoclonal antibody or a portion thereof according to claim 1.

8. A polynucleotide encoding the light chain of the monoclonal antibody or a portion thereof according to claim 1.

9. A polynucleotide encoding both the heavy chain and the light chain of the monoclonal antibody or portion thereof according to claim 1.

10. An expression vector comprising:
    a) a polynucleotide encoding the heavy chain of the monoclonal antibody, or portion thereof according to claim 1;
    b) a polynucleotide encoding the light chain of the monoclonal antibody, or portion thereof according to claim 1; or
    c) polynucleotide encoding both the heavy chain and the light chain of the monoclonal antibody or a portion thereof according to claim 1.

11. A host cell transformed with an expression vector according to claim 10.

12. The host cell according to claim 11, wherein said cell is a mammalian cell.

13. A method for producing a monoclonal antibody comprising the steps of:
    a) culturing a host cell according to claim 12; and
    b) isolating said antibody produced by the host cell.

14. A pharmaceutical composition comprising a monoclonal antibody according to claim 1.

15. The monoclonal antibody according to claim 1, wherein:
    a) the heavy chain variable domain comprises SEQ ID NO: 24; and
    b) the light chain variable domain comprises SEQ ID NO:25.

* * * * *

UNITED STATES PATENT AND TRADEMARK OFFICE
CERTIFICATE OF CORRECTION

| | | |
|---|---|---|
| PATENT NO. | : 11,597,771 B2 | Page 1 of 1 |
| APPLICATION NO. | : 16/462961 | |
| DATED | : March 7, 2023 | |
| INVENTOR(S) | : Christel Iffland et al. | |

It is certified that error appears in the above-identified patent and that said Letters Patent is hereby corrected as shown below:

In the Specification

Column 21,
Line 25 (SEQ ID NO: 30), "TGAVS" should read --TCAVS--.

Column 25,
Line 50 (SEQ ID NO: 49), "TREV" should read --TPEV--.
Line 50 (SEQ ID NO: 49), "VEVFINAKTKPREECNN" should read --VEVHNAKTKPREEQYN--.
Line 51 (SEQ ID NO: 49), "LIVL" should read --LTVL--.
Line 52 (SEQ ID NO: 49), "KGRYP" should read --KGFYP--.

Column 37,
Line 32 (SEQ ID NO: 91), "WWSVVVR" should read --WWSWVR--.

Column 55,
Line 27, "C105S, N114S" should read --C105S, N114S--.

Signed and Sealed this
Fifth Day of September, 2023

Katherine Kelly Vidal
*Director of the United States Patent and Trademark Office*